United States Patent
Ranjan et al.

(10) Patent No.: US 11,524,939 B2
(45) Date of Patent: Dec. 13, 2022

(54) SOLID FORMS OF {[5-(3-CHLOROPHENYL)-3-HYDROXYPYRIDINE-2-CARBONYL]AMINO} ACETIC ACID

(71) Applicant: Akebia Therapeutics, Inc., Cambridge, MA (US)

(72) Inventors: Sudhir Ranjan, Lexington, MA (US); Xiaoyang Wang, Shanghai (CN)

(73) Assignee: Akebia Therapeutics, Inc., Cambridge, MA (US)

( * ) Notice: Subject to any disclaimer, the term of this patent is extended or adjusted under 35 U.S.C. 154(b) by 182 days.

(21) Appl. No.: 17/095,998

(22) Filed: Nov. 12, 2020

(65) Prior Publication Data

US 2021/0206721 A1    Jul. 8, 2021

Related U.S. Application Data

(60) Provisional application No. 62/934,888, filed on Nov. 13, 2019.

(51) Int. Cl.
*C07D 213/81* (2006.01)
*A61K 9/00* (2006.01)

(52) U.S. Cl.
CPC .......... *C07D 213/81* (2013.01); *A61K 9/0053* (2013.01)

(58) Field of Classification Search
CPC .................................................. C07D 213/81
See application file for complete search history.

(56) References Cited

U.S. PATENT DOCUMENTS

| | | | |
|---|---|---|---|
| 3,894,920 A | 7/1975 | Kondo et al. | |
| 4,016,287 A | 4/1977 | Ebhardt et al. | |
| 5,067,954 A | 11/1991 | Ilizarov | |
| 5,397,799 A | 3/1995 | Kress et al. | |
| 5,405,613 A | 4/1995 | Rowland | |
| 5,607,954 A | 3/1997 | Weidmann et al. | |
| 5,610,172 A | 3/1997 | Weidmann et al. | |
| 5,620,995 A | 4/1997 | Weidmann et al. | |
| 5,620,996 A | 4/1997 | Weidmann et al. | |
| 5,658,933 A | 8/1997 | Weidmann et al. | |
| 5,719,164 A | 2/1998 | Weidmann et al. | |
| 5,726,305 A | 3/1998 | Weidmann et al. | |
| 6,020,350 A | 2/2000 | Weidmann et al. | |
| 6,093,730 A | 7/2000 | Weidmann et al. | |
| 6,159,379 A | 12/2000 | Means et al. | |
| 6,420,427 B1 | 7/2002 | Takahashi et al. | |
| 6,566,088 B1 | 5/2003 | McKnight et al. | |
| 6,589,758 B1 | 7/2003 | Zhu | |
| 7,588,924 B2 | 9/2009 | Evdokimov et al. | |
| 7,811,595 B2 | 10/2010 | Kawamoto et al. | |
| 8,050,873 B2 | 11/2011 | Evdokimov et al. | |
| 8,124,582 B2 | 2/2012 | Guenzler-Pukall et al. | |
| 8,323,671 B2 | 12/2012 | Wu et al. | |
| 8,343,952 B2 | 1/2013 | Wu et al. | |
| 8,512,972 B2 | 8/2013 | Evdokimov et al. | |
| 8,530,404 B2 | 9/2013 | Seeley et al. | |
| 8,598,210 B2 | 12/2013 | Kawamoto et al. | |
| 8,722,895 B2 | 5/2014 | Kawamoto et al. | |
| 8,865,748 B2 | 10/2014 | Shalwitz et al. | |
| 8,940,773 B2 | 1/2015 | Kawamoto et al. | |
| 9,145,366 B2 | 9/2015 | Lanthier et al. | |
| 9,598,370 B2 | 3/2017 | Kawamoto et al. | |
| 9,701,636 B2 | 7/2017 | Copp et al. | |
| 9,776,969 B2 | 10/2017 | Lanthier et al. | |
| 9,987,262 B2 | 6/2018 | Copp et al. | |
| 10,149,842 B2 | 12/2018 | Lanthier et al. | |
| 10,246,416 B2 | 4/2019 | Lanthier et al. | |
| RE47,437 E | 6/2019 | Kawamoto et al. | |
| 10,596,158 B2 | 3/2020 | Copp et al. | |
| 10,703,724 B2 | 6/2020 | Chen et al. | |
| 10,729,681 B2 | 8/2020 | Kawamoto et al. | |
| 10,738,010 B2 | 8/2020 | Lanthier et al. | |
| 11,065,237 B2* | 7/2021 | Copp | A61K 31/4418 |
| 2002/0192737 A1 | 12/2002 | Kaelin, Jr. et al. | |
| 2003/0153503 A1 | 8/2003 | Klaus et al. | |

(Continued)

FOREIGN PATENT DOCUMENTS

| | | |
|---|---|---|
| CA | 2098158 A1 | 6/1993 |
| CA | 2253282 A1 | 11/1997 |

(Continued)

OTHER PUBLICATIONS

U.S. Appl. No. 16/908,092, filed Jun. 22, 2020, Kawamoto et al.
U.S. Appl. No. 16/921,273, filed Jul. 6, 2020, Lanthier et al.
"Standards of Medical Care in Diabetes-2006," Diabetes Care, 29:s4-s42 (2006).
Alesso et al., "Improving resins for solid phase synthesis: incorporation of 1-[2-(2-methoxyethoxy)ethoxy]4-vinyl-benzene" Tetrahedron: 59,7163-7169 (2003).
Altschul et al., "Gapped BLAST and PSI-BLAST: A New Generation of Protein Database Search Programs," Nucleic Acids Res., 25(27):3389-3402 (1997).
Anderson et al., "Antileukemic Activity of Derivatives of 1,2-Dimethyl-3,4-bis(hydroxymethyl)-5-phenylpyrrole Bis(N-methylcarbamate)" J. Med. Chem.: vol. 22(8). 977-980 (1979).

(Continued)

*Primary Examiner* — Golam M Shameem
(74) *Attorney, Agent, or Firm* — Proskauer Rose LLP; Fangli Chen

(57) ABSTRACT

Provided herein are solid forms of {[5-(3-chlorophenyl)-3-hydroxypyridine-2-carbonyl]amino}acetic acid (Vadadustat, Code: AKB-6548, Compound 1), compositions comprising such solid forms, and methods of making and using thereof.

Compound 1

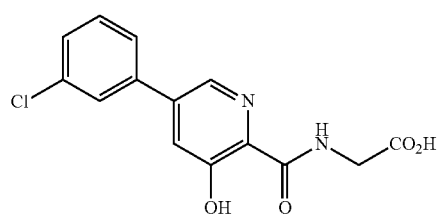

20 Claims, 33 Drawing Sheets

(56) References Cited

U.S. PATENT DOCUMENTS

| | | |
|---|---|---|
| 2003/0176317 A1 | 9/2003 | Guenzler-Pukall et al. |
| 2004/0235082 A1 | 11/2004 | Fourney et al. |
| 2004/0254215 A1 | 12/2004 | Arend et al. |
| 2006/0142389 A1 | 6/2006 | Aurell et al. |
| 2006/0276477 A1 | 12/2006 | Klaus et al. |
| 2007/0105899 A1 | 5/2007 | Suzuki et al. |
| 2007/0154482 A1 | 7/2007 | Sukhatme et al. |
| 2007/0213335 A1 | 9/2007 | Fitch et al. |
| 2007/0299086 A1 | 12/2007 | Kawamoto et al. |
| 2008/0124740 A1 | 5/2008 | Evdokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2010/0331303 A1 | 12/2010 | Kawamoto et al. |
| 2010/0331374 A1 | 12/2010 | Wu et al. |
| 2011/0077400 A1 | 3/2011 | Lobben et al. |
| 2012/0230997 A1 | 9/2012 | Van Lookeren Campagne et al. |
| 2012/0282627 A1 | 11/2012 | Evdokimov et al. |
| 2012/0309977 A1 | 12/2012 | Lanthier et al. |
| 2012/0329836 A1 | 12/2012 | Marsh et al. |
| 2013/0203816 A1 | 8/2013 | Kawamoto et al. |
| 2013/0230997 A1 | 9/2013 | Van Lookeren Campagne et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0141467 A1 | 5/2015 | Copp et al. |
| 2015/0361043 A1 | 12/2015 | Lanthier et al. |
| 2016/0009648 A1 | 1/2016 | Kawamoto et al. |
| 2016/0143891 A1 | 5/2016 | Shalwitz et al. |
| 2016/0214939 A1 | 7/2016 | Hanselmann et al. |
| 2016/0339005 A1 | 11/2016 | Shalwitz et al. |
| 2017/0189387 A1 | 7/2017 | Kawamoto et al. |
| 2017/0258773 A1 | 9/2017 | Copp et al. |
| 2018/0065933 A1 | 3/2018 | Hanselmann |
| 2018/0092892 A1 | 4/2018 | Smith et al. |
| 2020/0345711 A1 | 11/2020 | Copp et al. |
| 2021/0070709 A1 | 3/2021 | Gorin et al. |

FOREIGN PATENT DOCUMENTS

| | | |
|---|---|---|
| EP | 0650960 B1 | 3/1995 |
| EP | 0650961 B1 | 3/1995 |
| JP | H09221476 A | 8/1997 |
| JP | 2001-048786 | 2/2001 |
| JP | 2007-194072 A | 8/2007 |
| WO | WO 1997/041103 A1 | 11/1997 |
| WO | WO 1997/044333 A1 | 11/1997 |
| WO | WO 1999/048870 A1 | 9/1999 |
| WO | WO 2001/051919 A2 | 7/2001 |
| WO | WO 2002/074980 A2 | 9/2002 |
| WO | WO 2002/074981 A2 | 9/2002 |
| WO | WO 2002/083688 A1 | 10/2002 |
| WO | WO 2003/028663 A2 | 4/2003 |
| WO | WO 2003/032972 A1 | 4/2003 |
| WO | WO 2003/049686 A2 | 6/2003 |
| WO | WO 2003/053997 A2 | 7/2003 |
| WO | WO 2006/114213 A1 | 11/2006 |
| WO | WO 2006/127936 | 11/2006 |
| WO | WO 2006/138511 A2 | 12/2006 |
| WO | WO 2007/047194 A2 | 4/2007 |
| WO | WO 2007/070359 A2 | 6/2007 |
| WO | WO 2007/082899 A1 | 7/2007 |
| WO | WO 2007/084667 A2 | 7/2007 |
| WO | WO 2007/088571 A2 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/002576 A2 | 1/2008 |
| WO | WO 2008/089051 A1 | 7/2008 |
| WO | WO 2008/089052 A2 | 7/2008 |
| WO | WO 2008/130508 A1 | 10/2008 |
| WO | WO 2008/130527 A1 | 10/2008 |
| WO | WO 2008/137060 A1 | 11/2008 |
| WO | WO 2008/144266 A1 | 11/2008 |
| WO | WO 2009/019656 A1 | 2/2009 |
| WO | WO 2009/037570 A2 | 3/2009 |
| WO | WO 2009/039321 A1 | 3/2009 |
| WO | WO 2009/039323 A1 | 3/2009 |
| WO | WO 2007/038571 A2 | 4/2009 |
| WO | WO 2009/043093 A1 | 4/2009 |
| WO | WO 2009/049112 A1 | 4/2009 |
| WO | WO 2009/067790 A1 | 6/2009 |
| WO | WO 2009/070644 A1 | 6/2009 |
| WO | WO 2009/073497 A2 | 6/2009 |
| WO | WO 2009/073669 A1 | 6/2009 |
| WO | WO 2009/086044 A1 | 7/2009 |
| WO | WO 2009/086592 A1 | 7/2009 |
| WO | WO 2009/089547 A1 | 7/2009 |
| WO | WO 2012/170377 A1 | 12/2012 |
| WO | WO 2012/170439 A1 | 12/2012 |
| WO | WO 2012/170442 A1 | 12/2012 |
| WO | WO 2013/013609 A1 | 1/2013 |
| WO | WO 2014/200773 A2 | 12/2014 |
| WO | WO 2015/073779 A1 | 5/2015 |
| WO | WO 2015/112831 A1 | 7/2015 |
| WO | WO 2016/118858 A1 | 7/2016 |
| WO | WO 2016/153996 A1 | 9/2016 |
| WO | WO 2016/161094 A1 | 10/2016 |

OTHER PUBLICATIONS

Annex et al., "Growth Factor-Induced Therapeutic Angiogenesis in the Heart: Protein Therapy," Cardiovascular Research, 65(3):649-655 (2005).

Ardelt et al. "Estradiol Regulates Angiopoietin-1 mRNA Expression Through Estrogen Receptor—alpha in a Rodent Experimental Stroke Model," Stroke, 36:33 7-3-11 (2005).

Auerbach et al., "Angiogenesis Assays: A Critical Overview." Clinical Chemistry. 49:32-40 (2003).

Barany et al., "Solid-phase Peptide Synthesis: A Silver Anniversary Report" Int. J. Peptide Protein Res., 30(6):705-739 (1987).

Bartlett et al., "Molecular Recognition in Chemical and Biological Problems," Special Pub., Royal Chem. Soc., 78, 182-196 Caveat: A Program to Facilitate the Structure-derived Design of Biologically Active Molecules (Apr. 1989).

Bauer et al., "Ritonvir: An Extraordinary Example of Conformational Polymorphism", Pharma. Res., 18(6): 859-866 (2001).

Bauer, "Polymorphism—A Critical Consideration in Pharmaceutical Development, Manufacturing, and Stability," Journal of Validation Technology, 15-23 (2008).

Bernstein, "Crystal Structure Prediction and Polymorphism," ACA 18 Transactions 39:14-23 (2004).

Bohm, "The Computer Program LUDI: A New Method for the Novo Design of Enzyme Inhibitors," J. Computer-Aided Molecular Design, 6:61-78 (1992).

Braga et al., "Crystal polymorphism and multiple crystal forms." Molecular networks (2009): 87-95.

Braga and Grepioni, "Making crystals from crystals: a green route to crystal 12 engineering and polymorphism," Chem. Commun.:3635-3645 (2005).

Branden et al., "Introduction to Protein Structure Second Edition," Garland Publishing, Inc., New York, pp. 374-375 (1999).

Brittain et al., "Polymorphism in Pharmaceutical Solids". Drugs and the Pharmaceutical Sciences. vol. 192, p. 334 (2009).

Brittain et al., "Polymorphism in pharmaceutical solids" [Edited by H. G. Brittain, Marcel Dekker, D.J.W. Grant (chapter 1); p. 1-10 and J. K. Guillory (chapter 5); p. 183-226]—Dec. 31, 1999.

Bucar et al., "Disappearing Polymorphs Revisited", Angewandte Rev. Int'l Ed., 54: 6972-6993 (2015).

Burger, Isosterism and biososterism in drug design, Progress in Drug Research, Birkhauser Verlag (1991).

Bussolino, "Molecular Mechanisms of Blood Vessel Formation" Trends Biochem. Sci., 22(7):251-256 (1997).

Byrn et al., "Pharmaceutical Solids: A Strategic Approach to Regularity Considerations", Pharmaceutical Research, 12(7): 945-954 (1995).

Caira et al., "Crystalline Polymorphism of Organic Compounds", Topics in Current Chemistry, vol. 198: 163-208 (1998).

(56) References Cited

OTHER PUBLICATIONS

Catrina et al., "Hyperglycemia Regulates Hypoxia-Inducible Factor-1a Protein Stability and Function," Diabetes 53:3226-3232 (2004).
Censi et al., "Polymorph Impact on the Bioavailability and Stability of Poorly Soluble Drugs", Molecules, 20: 18759-18776 (2015), doi:10.3390/molecules201018759.
Cheeseright, "The Identification of Bioisosteres as Drug Development Candidates", Innovations in Pharmaceutical Technology, issue 28 (2009).
Cruz-Cabeza et al., "Facts and Fictions about Polymorphism", Chem. Soc. Rev., 44:8619-8635 (2015).
Cunliffe et al., "Novel Inhibitors of Prolyl 4-Hydroxylase. 3. Inhibition by the Substrate Analogue N-Oxaloglycine and Its Derivatives." J. Med. Chem. 35:2652-2658 (1992).
Dranoff, "GM-CSF-secreting melanoma vaccines", Oncogene, 22:3188-3192 (2003).
Elson et al., "Induction of Hypervascularity Without Leakage or Inflammation in Transgenic Mice Overexpressing Hypoxia-Indicibie Factor-1α," Genes & Dev., 15:2520-2532 (2001).
European Patent Office, Interlocutory Decision in Opposition Proceedings, mailed May 3, 2013, 76 pages.
European Patent Office, Minutes of the Oral Proceedings Before the Opposition Division, mailed May 3, 2013, 6 pages.
Extended European Search Report dated Mar. 24, 2017 for European Pat. App. No. 14861394.6.
Florence et al., "Physicochemical Principles of Pharmacy", Chapter 1: Solids, Pharmaceutical Press, 6$^{th}$ edition, (Dec. 2015).
Flower, "Modelling G-protein-coupled receptors for drug design," Biochimica et Biophysica Acta, 1422:207-234 (1999).
Folkman et al., "Tumor Angiogenesis," The Molecular Basis of Cancer, Mendelsohn et al., eds., W.B. Saunders. Chapter 10, pp. 206-232 (1995).
Franklin et al., "Approaches to the Design of Anti-Fibrotic Drugs," Biochem. Soc. Trans., 19(4):812-5 (Nov. 1991).
Gaunt, "Rational Design of Benzyl-Type Protecting Groups Allows Sequential Deprotection of Hydroxyl Groups by Catalytic Hydrogenolysis", 63(13): 4172-4173 (1998).
Goodford, "A Computational Procedure for Determining Energetically Favorable Binding Sites on Biologically Important Macromolecules," J. Med. Chem., 28(7):849-857 (1985).
Goodsell et al., "Automated Docking of Substrates to Proteins by Simulated Annealing," Proteins: Structure, Function, and Genetics, 8: 195-202 (1990).
Hardcastle et al., "Discovery of Potent Chromen-4-one Inhibitors of the DNA-Dependent Protein Kinase (DNA-PK) Using a Small-Molecule Library Approach", J. of Medicinal Chem., 48(24): 7829-7846 (2005).
"Hippuric acid sodium salt", Science Lab.com: Chemicals & Laboratory Equipment (*http://web.archive.org/web/20041107121553/http://www.sciencelab.com/page/S/PVAR/10415/SLH2620 accessed Mar. 11, 2010).
Hoesksema et al., "Structure of Rubradirin", J. of American Chem. Society, 104(19): 5173-5181 (1982).
International Search Report dated May 8, 2008 for PCT/US2007/014832.
International Search Report and Written Opinion dated Jan. 29, 2015 for International Application No. PCT/US14/65631.
International Union of Pure and Applied Chemistry; Glossary of Class Names of Organic Compounds and Reactive Intermediates Based on Structure: Pure & D Appl. Chem., vol. 67, Nos. 8/9, pp. 1307-1375, (1995).
Ivan et al., "Biochemical purification and pharmacological inhibition of a mammalian prolyl hydroxylase acting on hypoxia-inducible factor," Proceedings of the National Academy of Science; 99(21) 13459-13464 (2002).
Ivan et al., "HIFa Targeted for VHL-Mediated Destruction by Praline Hydroxylation: Implications for 02 Sensing," Science 292, 464-468 (2001).

Ivanisevic, I. et al., "Uses of X-Ray Powder Diffraction in the Pharmaceutical Industry. Pharmaceutical Formulation & Quality", Aug./Sep. 2011, p. 32.
Jaakkola et al., "Targeting of HIF-α to the von Hippel-Lindau Ubiquitylation Complex by $O_2$-Regulated Prolyl Hydroxylation," Science 292, 468-472 (2001).
Jones et al., "Molecular Recognition of Receptor Sites Using a Genetic Algorithm with a Description of Desolvation," J. Mol. Biol., 245:43-53 (1995).
Jones et al., "Pharmaceutical Cocrystals: An Emerging Approach to Physical 14 Property Enhancement," MRS Bulletin 31:875-879 (2006).
Kaelin, "Proline Hydroxylation and Gene Expression," Annu. Rev. Biochem., 74:115-125 (2005).
Kawaguchi et al., Journal of Human Environmental Engineering, vol. 4, No. 2, pp. 310-317 (2002).
Kawashima et al., Suppressive effect of quinolinic acid and hippuric acid on bone marrow erythroid growth and lymphocyte blast formation in uremia, Advances in Experimental Medicine and Biology, vol. 223, p. 69-72 (1987).
Krantz, "Erythropoietin," Blood, 77:419-434 (1991).
Kuntz et al., A Geometric Approach to Macromolecule-Ligand Interactions, J. Mol. Biol., 161:269-288 (1982).
Langsetmo, "Inhibition of HIF-Prolyl Hydroxylases with FG-4539 is Neuroprotective in a Mouse Model of Permanent Focal Ischemia," International Stroke Conference, Kissimmee Florida, Presentation No. 427 (2006).
Lee et al., "Structure of Human FIH-1 Reveals a Unique Active Site Pocket and Interaction Sites for HIF-1 and von Hippel Lindau," JBC, 278:7558-7563 (2003).
Lerma, "Patentability of polymorphic compounds", Universidad Peruana Cayetano Heredia, pp. 277-293 (2007).
Li et al., "PR39, A Peptide Regulator of Angiogenesis," Nat Med., 6(1):49-55 (2000).
Lima et al., "Bioisosterism: A Useful Strategy for Molecular Modification and Drug Design", Current Medicinal Chemistry, 12:23-49 (2005).
Mancini et al., "Effect of Erythropoietin on Exercise Capacity in Patients with Moderate to Severe Chronic Heart Failure," Circulation, 107:294-299 (2003).
McDonough et al., "Cellular Oxygen Sensing: Crystal Structure of Hypoxia-Inducible Factor Prolyl Hydroxylase (PHD2)," PNAS, 103(26):9814-9819 (2006).
Morissette et al., "High-throughput crystallization: polymorphs, salts, co-crystals and solvates of pharmaceutical solids", Adv. Drug Del. Rev., 56(3): 275-300 (2004).
Miranker et al., "Functionality Maps of Binding Sites: A Multiple Copy Simultaneous Search Method," Proteins: Structure, Function and Genetics, 11:29-34 (1991).
Nguyen et al., "Cellular Interactions in Vascular Growth and Differentiation" Int. Review of Cytology. 204:1-48 (2001).
Nishibata et al., "Automatic Creation of Drug Candidate Structures Based on Receptor Structure. Starting Point for Artificial Lead Generation," Tetrahedron. 47( 43):8985-8990 (1991).
Notification No. 568 of Pharmaceutical Safety and Environmental Health Bureau, Evaluation and Licensing Division, 2001.
Office Action received in Japan Patent Application No. 2016-530958, dated Jun. 30, 2020, 10 pages.
O'Reilly et al., "Angiostatin: A Novel Angiogenesis Inhibitor that Mediates the Suppression of Metastases by a Lewis Lung Carcinoma," Cell, 79:315-328 (1994).
O'Reilly et al., "Endostatin: An Endogenous Inhibitor of Angiogenesis and Tumor Growth," Cell, 88:277-285 (1997).
Peyssonnaux et al., "HIF-1α Expression Regulates the Bactericidal Capacity of Phagocytes," J. Clinical Invest., 115(7): 1806-1815 (2005).
PHARM Stage 2007, vol. 6, No. 10, pp. 20-25 "API form screening and selection in drug discovery stage".
PHARM Stage 2007, vol. 6, No. 10, pp. 48-53 "Crystallization of Polymorphs and Pseudo-polymorphs and Its Control".
Piyamongkol et al., "Amido-3-hydroxypyridin-4-ones as Iron (III) Ligands", Chemistry A European Journal, vol. 16: 6374-6381 (2010).

(56) References Cited

OTHER PUBLICATIONS

Pre-grant Opposition Documents received in India Patent Application No. 20164 7016515, Dated: Dec. 1, 2020, 42 pages.
Price, "The computational prediction of pharmaceutical crystal structures 16 and polymorphism," Advanced Drug Delivery Reviews 56:301-319 (2004).
Qian et al., "A Randomized, Double-Blind, Placebo Controlled Trial of FG-4592 for Correction of Anemia in Subjects with Chronic Kidney Disease in China," Oral Abstract FR-OR0011, J. Am. Soc. Nephrol. 24:38A (2013).
Rahtu-Korpela, "HIF Prolyl 4-Hydroxylase-2 Inhibition Improves Glucose and Lipid Metabolism and Protects Against Obesity and Metabolic Dysfunction," Diabetes 63:3324-:3333 (2014).
Redondo et al., "Vascular endothelial growth factor (VEGF) and melanoma. N-Acetylcysteine downregulates VEGF Production in vitro", Cytokine, 12(4):374-378 (2000).
Santos et al., "Polymorphism: an evaluation of the potential risk to the quality of drug products from the Farmácia Popular Rede Própria", Brazilian J. Pharma. Sci., 50(1): 1-24 (2014).
Schelhass et al., "Protecting Group Strategies in Organic Synthesis". Chem. Int. Ed. Engl., 36:2056-2083 (1996).
Schoneberg et al., "Structural Basis of G Protein-Coupled Receptor Function," Molecular and Cellular Endocrinology, 151:181-193 (1999).
Search Report dated Apr. 28, 2011 for European Pat. App. No. 11000872.9.
Sekhon, "Pharmaceutical co-crystals,—a review," Ars. Pharm., 50(2):99-117 (2009).
Semenza et al., "Transcriptional Regulation of Genes Encoding Glycolytic Enzymes by Hypoxia-Inducible Factor 1," J. Biol. Chem., 269:23757-23763 (1994).
Semenza, "Regulation of Erythropoietin Production: New Insights into Molecular Mechanisms of Oxygen Homeostasis," Hematol. Oncol. Clin. North Am., 8:863-884 (1994).
Semenza, "Signal Transduction to Hypoxia-inducible Factor 1," Biochem. Pharmacol, 64:993-998 (2002).
Sexton, "Recent advances in our understanding of peptide hormone receptors and RAMPS," Current Opinion in Drug Discovery and Development, 2(5):440-448 (1999).
Seymour et al., "Decision T 0777/08 of the Boards of Appeal of the European Patent Office", retrieved from the internet: http://www.epo.org/law-practice/case-law-appeals/pdf/t080777ex1.pdf [retrieved Dec. 19, 2017] (2011).
Sheehan, "3-Hydroxypicolinic Acid and Some of its Derivatives," J. Organic Chemistry 31(1):636-6:38 (1996).
Sutter, "Hypoxia-inducible factor 1 alpha protein expression is controlled by oxygen regulated ubiquitination that is disrupted by deletions and missense mutations", PNAS vol. 97, No. 9, pp. 4748-4753 (2000).
Teicher et al., "Potentiation of Cytotoxic Cancer Therapies by TNP-470 Alone and with Other Anti-Angiogenic Agents," Int. J. Cancer, 57:920-925 (1994).
Thornber, "Isosterism and Molecular Modification in Drug Design", Progress Drug Res., vol. 37: 563-580 (1979).
Tzschucke et al., "Fluorous-Silica-Supported Perfluoro-Tagged Palladium Complexes Catalyze Suzuki Coupling in Water" Helvetica Chimica Acta: vol. 87 2882-2889 (2004).
U.S. Dept. HHS, FDA Center for Drug Evaluation and Research (CDER), Guidance for Industry, ANDAs: Pharmaceutical Solid Polymorphism, Chemistry, Manufacturing, and Controls Information, (Jul. 2007).
Vickerstaffe et al., "Fully Automated Polymer-Assisted Synthesis of 1,5-Biaryl Pyrazoles," J. Comb. Chem., 6, 332-33 (2004).
Vippagunta et al., "Crystalline solids." Adv Drug Deliv Rev. 48(1):3-26 (2001).
Vincent et al., "Angiogenesis is Induced in a Rabbit Model of Hindlimb Ischemia by Naked DNA Encoding an HIF-1a/VP16 Hybrid Transcription Factor," Circulation, 102:2255-2261 (2000).
Warnecke et al., "Activation of the Hypoxia-Inducible Factor Pathway and Stimulation of Angiogenesis by Application of Prolyl Hydroxylase Inhibitors," FASEB Journal, 17: 1186-1188 (2003).
Warshakoon et al., "Design and synthesis of substituted pyridine derivatives as HIF-1alpha prolyl hydroxylase inhibitors," Bioorganic & Medicinal Chemistry Letters, 16, 5616-5620(2006).
Wax et al., "SM-20 is a Novel20-kd Protein Whose Expression in the Arterial Wall is Restricted to Smooth Muscle," Lab. Invest., 74(4):797-808 (1996).
Weidner et al., "Tumor Angiogenesis and Metastasis—Correlation in Invasive Breast Carcinoma," New Eng. J. Med., 324(1):1-8 (1991).
Wright et al., "Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes," J. Bio. Chem., 278(22):20235-20239 (2003).
Yamano, "Approach to Crystal Polymorph in Process Research of New Drug", Journal of Society of Synthetic Organic Chemistry, Japan, vol. 65, pp. 907-913 (2007).

* cited by examiner

SOLID FORMS OF {[5-(3-CHLOROPHENYL)-3-HYDROXY-PYRIDINE-2-CARBONYL]AMINO} ACETIC ACID

CROSS-REFERENCE TO RELATED APPLICATIONS

The present application claims benefit of U.S. Provisional Patent Application No. 62/934,888, filed on Nov. 13, 2019, which is hereby incorporated by reference in its entirety.

BACKGROUND

{[5-(3-chlorophenyl)-3-hydroxypyridine-2-carbonyl]amino}acetic acid (Vadadustat, Code: AKB-6548, Compound 1), having a chemical formula:

Compound 1

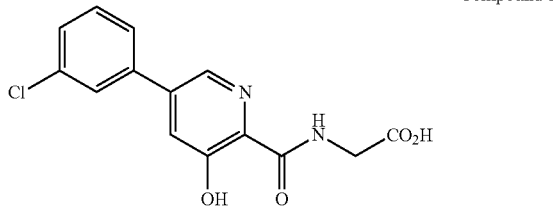

is prolyl hydroxylase inhibitor, which may prevent diseases ameliorated by modulation of hypoxia-inducible factor (HIF) prolyl hydroxylase (e.g., Peripheral Vascular Disease (PVD), Coronary Artery Disease (CAD), heart failure, ischemia, hypoxia, and anemia). In particular, Compound 1 is useful for treating and preventing anemia secondary to or associated with chronic kidney disease (renal anemia).

Active pharmaceutical ingredients (APIs), such as Compound 1, can be prepared in a variety of different solid forms. For example, they may be amorphous, they may exist as different crystalline polymorphs, and/or they may exist in different solvation or hydration states. The desired solid form depends upon the specific application. Changes to the solid form affect the physical and chemical properties of the API, and such changes provide both benefits or drawbacks to, e.g., processing, storage, formulation, stability, and bioavailability, as well as other important pharmaceutical characteristics. Therefore, the identification and selection of a solid form of a pharmaceutical Compound 1 is complex. Accordingly, there exists a need to provide solid forms of Compound 1, which may have desirable pharmaceutical properties, especially for use as solid (e.g. oral) pharmaceutical dosage forms.

SUMMARY OF THE INVENTION

Provided herein are solid forms of Compound 1, compositions comprising such solid forms, and methods of making and using thereof. In certain embodiments, the solid forms of Compound 1 are identifiable on the basis of groups of peaks in an X-ray powder diffraction analysis.

In one aspect, provided herein, is solid Form D of Compound 1:

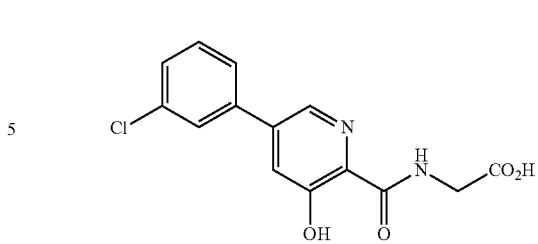

which has an X-ray powder diffraction pattern comprising peaks at 7.9, 14.4, 14.8, 15.9, and 23.9±0.2° 2θ.

In one aspect, provided herein, is solid Form D of Compound 1:

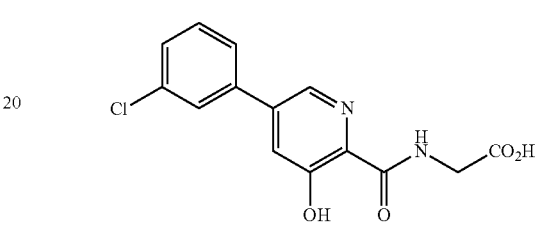

which has an X-ray powder diffraction pattern which comprises at least one of peak from the group consisting of 2.2, 6.6, 7.9, 13.4, 14.4, 14.8, 15.9, 20.1, 24.5, and 26.0±0.2° 2θ. In embodiments, the solid Form D of Compound 1 which comprises one, two, three, four, five, and/or six peaks from the group consisting of 2.2, 6.6, 7.9, 13.4, 14.4, 14.8, 15.9, 20.1, 24.5, and 26.0±0.2° 2θ.

In another aspect, provided herein, is solid Form D of Compound 1:

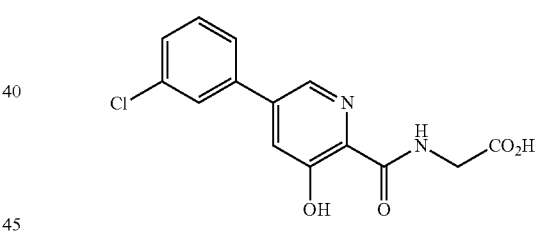

which has an X-ray powder diffraction pattern comprising peaks at 2.2, 6.6, 7.9, 14.8, and 26.0±0.2° 2θ.

In another aspect, provided herein, is solid Form D of Compound 1:

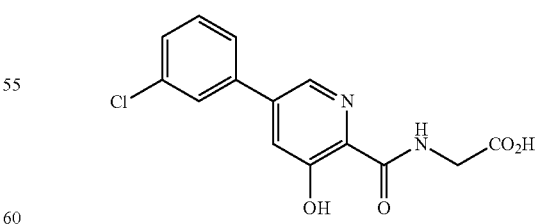

which has an X-ray powder diffraction pattern comprising peaks at 6.6, 7.9, 13.4, 15.9, 20.1 and 24.5±0.2° 2θ.

In embodiments, the solid Form D of Compound 1 is anhydrous and unsolvated.

In embodiments, the solid Form D of Compound 1 has a DSC endotherm peak temperature at about 174.5° C.

In embodiments, the solid Form D of Compound 1 has a DSC endotherm onset temperature at about 70.8, 87.6, and 172.1° C.

In another aspect, provided herein, solid Form D of Compound 1:

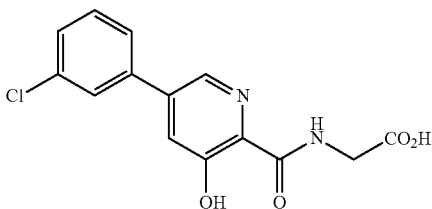 [SMILES: O=C(O)CNC(=O)c1ncc(-c2cccc(Cl)c2)cc1O]

which has an X-ray powder diffraction pattern substantially in accordance with FIG. 1.

In another aspect, provided herein, is solid Form D of Compound 1:

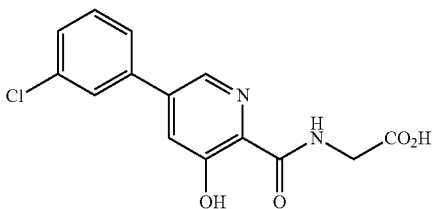 [SMILES: O=C(O)CNC(=O)c1ncc(-c2cccc(Cl)c2)cc1O]

which is prepared from a solution comprising methanol or methanol/water and Compound 1; wherein the solid Form D of Compound 1 has an X-ray powder diffraction pattern comprising peaks at 7.9, 14.4, 14.8, 15.9, and 23.9±0.2° 2θ, at 6.6, 7.9, 13.4, 15.9, 20.1, and 24.5±0.2° 2θ, or at 2.2, 6.6, 7.9, 14.8, and 26.0±0.2° 2θ. In embodiments, the solid Form D of Compound 1 has an X-ray powder diffraction pattern which comprises at least one of peak from the group consisting of 2.2, 6.6, 7.9, 13.4, 14.4, 14.8, 15.9, 20.1, 24.5, and 26.0±0.2° 2θ. In embodiments, solid Form D of Compound 1 which comprises one, two, three, four, five, and/or six peaks from the group consisting of 2.2, 6.6, 7.9, 13.4, 14.4, 14.8, 15.9, 20.1, 24.5, and 26.0±0.2° 2θ.

In embodiments, the preparation method comprises slow cooling 60° C. to 0° C. at 0.1° C./min.

In some embodiments, the preparation comprises fast cooling in the presence of 0, 5, 10, 15, or 20% water in methanol solution.

In another aspect, provided herein is a method of preparing solid Form D of Compound 1:

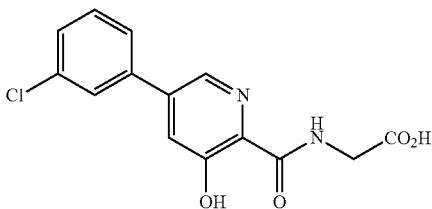 [SMILES: O=C(O)CNC(=O)c1ncc(-c2cccc(Cl)c2)cc1O]

comprising:
a) preparing a solution of Compound 1 in methanol or methanol/water;
b) bringing the solution to super-saturation to cause formation of solid Form D of Compound 1; and
c) isolating solid Form D of Compound 1.

In some embodiments of the method, solid Form D of Compound 1 has an X-ray powder diffraction pattern comprising peaks at 7.9, 14.4, 14.8, 15.9, and 23.9±0.2° 2θ. In other embodiments of the method, solid Form D of Compound 1 has an X-ray powder diffraction pattern comprising peaks at 2.2, 6.6, 7.9, 14.8, and 26.0±0.2° 2θ. In other embodiments of the method, solid Form D of Compound 1 has an X-ray powder diffraction pattern comprising peaks at 6.6, 7.9, 13.4, 15.9, 20.1, and 24.5±0.2° 2θ. In some embodiments of the method, solid Form D of Compound 1 has an X-ray powder diffraction pattern which comprises at least one peak selected from the group consisting of 2.2, 6.6, 7.9, 14.4, 14.8, 15.9, 23.9, and 26.0±0.2° 2θ. In some embodiments of the method, solid Form D of Compound 1 has an X-ray powder diffraction pattern which comprises one, two, three, four, and/or five peaks selected from the group consisting of 2.2, 6.6, 7.9, 14.4, 14.8, 15.9, 23.9, and 26.0±0.2° 2θ.

In some embodiments of the method, the method further comprising slow cooling 60° C. to 0° C. at 0.1° C./min.

In some embodiments of the method, the method further comprising fast cooling in the presence of 0, 5, 10, 15, or 20% water in methanol solution.

In some embodiments of the method, the solid Form D of Compound 1 has a DSC endotherm onset temperature at about 70.8, 87.6, and 172.1° C.

In another aspect, provided herein, is solid Form E of Compound 1:

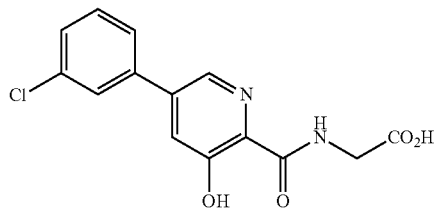 [SMILES: O=C(O)CNC(=O)c1ncc(-c2cccc(Cl)c2)cc1O]

which has an X-ray powder diffraction pattern comprising peaks at 21.3, 22.8, 23.7, 27.0, and 27.7±0.2° 2θ.

In another aspect, provided herein, is solid Form E of Compound 1:

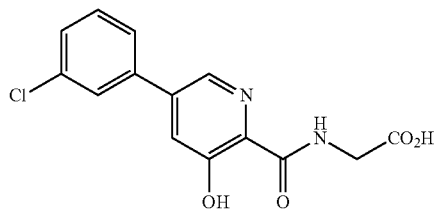 [SMILES: O=C(O)CNC(=O)c1ncc(-c2cccc(Cl)c2)cc1O]

which has an X-ray powder diffraction pattern comprising peaks at 16.4, 22.8, 23.7, 27.0, and 27.7±0.2° 2θ.

In another aspect, provided herein, is solid Form E of Compound 1:

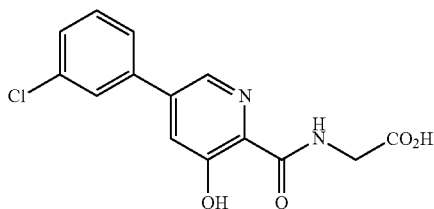 [SMILES: O=C(O)CNC(=O)c1ncc(-c2cccc(Cl)c2)cc1O]

which has an X-ray powder diffraction pattern which comprises at least one peak selected from the group consisting of 16.4, 21.3, 22.8, 23.7, 27.0, and 27.7±0.2° 2θ. In some embodiments, the solid Form E of Compound 1 which comprises one, two, three, four, and/or five peaks selected from the group consisting of 16.4, 21.3, 22.8, 23.7, 27.0, and 27.7±0.2° 2θ.

In embodiments, the solid Form E of Compound 1 is anhydrous and unsolvated.

In embodiments, the solid Form E of Compound 1 has a DSC endotherm peak temperature at about 175.4° C.

In embodiments, the solid Form E of Compound 1 has a DSC endotherm onset temperature at about 174.2° C.

In another aspect, provided herein, is solid Form E of Compound 1:

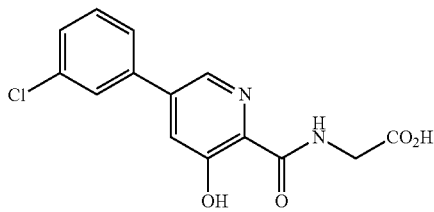 [SMILES: O=C(O)CNC(=O)c1ncc(-c2cccc(Cl)c2)cc1O]

which has an X-ray powder diffraction pattern substantially in accordance with FIG. 4.

In another aspect, provided herein, is solid Form E of Compound 1:

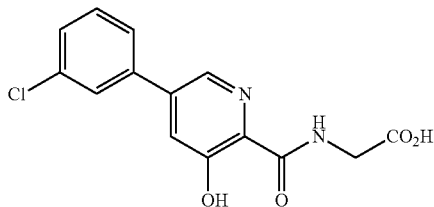 [SMILES: O=C(O)CNC(=O)c1ncc(-c2cccc(Cl)c2)cc1O]

which prepared from a solution comprising tetrahydrofuran or methyl ethyl ketone and Compound 1; wherein the solid Form E of Compound 1 has an X-ray powder diffraction pattern comprising peaks at 21.3, 22.8, 23.7, 27.0, and 27.7±0.2° 2θ or at 16.4, 22.8, 23.6, 27.0, and 27.7±0.2° 2θ.

In another aspect, provided herein, is a method of preparing solid Form E of Compound 1:

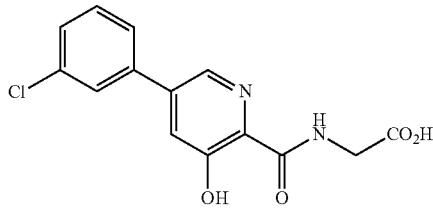 [SMILES: O=C(O)CNC(=O)c1ncc(-c2cccc(Cl)c2)cc1O]

comprising:
a) preparing a solution of Compound 1 in tetrahydrofuran or methyl ethyl ketone;
b) bringing the solution to super-saturation to cause formation of solid Form E of Compound 1; and
c) isolating solid Form E of Compound 1.

In some embodiments of the method, solid Form E of Compound 1 has an X-ray powder diffraction pattern comprising peaks at 21.3, 22.8, 23.7, 27.0, and 27.7±0.2° 2θ.

In some embodiments of the method, solid Form E of Compound 1 has an X-ray powder diffraction pattern comprising peaks at 16.4, 22.8, 23.7, 27.0, and 27.7±0.2° 2θ.

In some embodiments of the method, solid Form E of Compound 1 has an X-ray powder diffraction pattern which comprises at least one peak selected from the group consisting of 16.4, 21.3, 22.8, 23.7, 27.0, and 27.7±0.2° 2θ. In some embodiments of the method, solid Form E of Compound 1 has an X-ray powder diffraction pattern which comprises one, two, three, four, and/or five peaks selected from the group consisting of 16.4, 21.3, 22.8, 23.7, 27.0, and 27.7±0.2° 2θ.

In some embodiments of the method, the solid Form E of Compound 1 has a DSC endotherm onset temperature at about 174.2° C.

In another aspect, provided herein, is solid Form F of Compound 1:

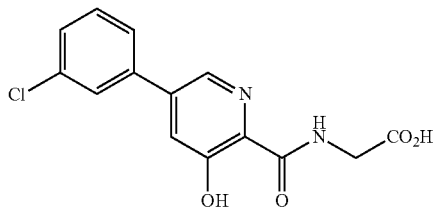 [SMILES: O=C(O)CNC(=O)c1ncc(-c2cccc(Cl)c2)cc1O]

which has an X-ray powder diffraction pattern comprising peaks at 8.5, 15.3, 18.5, 21.2, and 22.5±0.2° 2θ.

In another aspect, provided herein, is solid Form F of Compound 1:

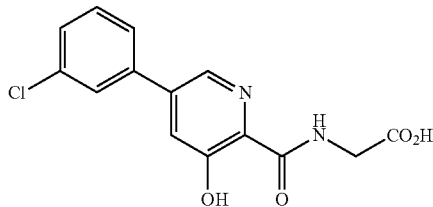 [SMILES: O=C(O)CNC(=O)c1ncc(-c2cccc(Cl)c2)cc1O]

which has an X-ray powder diffraction pattern comprising peaks at 4.2, 12.7, 19.5, 25.9, and 29.9±0.2° 2θ.

In another aspect, provided herein, is solid Form F of Compound 1:

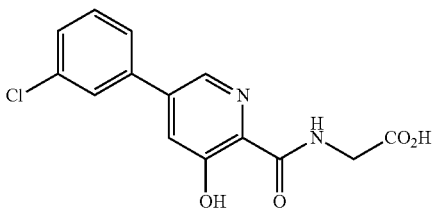 [SMILES: O=C(O)CNC(=O)c1ncc(-c2cccc(Cl)c2)cc1O]

which has an X-ray powder diffraction pattern comprising peaks at 4.2, 8.5, 15.3, 18.5, 21.3, and 22.5±0.2° 2θ.

In another aspect, provided herein, is solid Form F of Compound 1:

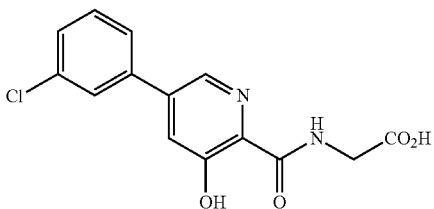 [SMILES: O=C(O)CNC(=O)c1ncc(-c2cccc(Cl)c2)cc1O]

which has an X-ray powder diffraction pattern which comprises at least one peak selected from the group consisting of 4.2, 8.5, 12.7, 15.3, 18.5, 19.5, 21.3, 22.5, 25.9, and 29.9±0.2° 2θ. In some embodiments, the solid Form F of Compound 1 which comprises one, two, three, four, and/or five peaks selected from the group consisting of 4.2, 8.5, 12.7, 15.3, 18.5, 19.5, 21.3, 22.5, 25.9, and 29.9±0.2° 2θ.

In embodiments, the solid Form F of Compound 1 is a crystalline form.

In embodiments, the solid Form F of Compound 1 is anhydrous and unsolvated.

In embodiments, the solid Form F of Compound 1 has a DSC endotherm peak temperature at about 174.2° C.

In embodiments, the solid Form F of Compound 1 has a DSC endotherm onset temperature at about 173.4° C.

In another aspect, provided herein, is solid Form F of Compound 1:

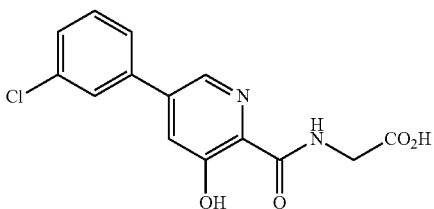 [SMILES: O=C(O)CNC(=O)c1ncc(-c2cccc(Cl)c2)cc1O]

which has an X-ray powder diffraction pattern substantially in accordance with FIG. 7.

In another aspect, provided herein, is solid Form F of Compound 1:

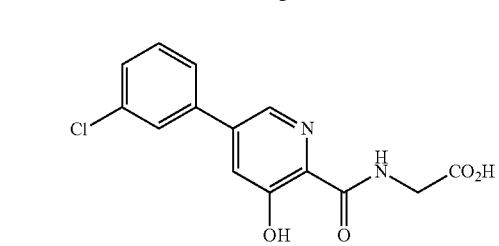

which is prepared by crystallization from a solution comprising ethanol/water and Compound 1; wherein the solid Form F of Compound 1 has an X-ray powder diffraction pattern comprising peaks at 8.5, 15.3, 18.5, 21.2, and 22.5±0.2° 2θ, at 4.2, 8.5, 15.3, 18.5, 21.3, and 22.5±0.2° 2θ, or at at 4.2, 12.7, 19.5, 25.9, and 29.9±0.2° 2θ. In some embodiments, the solid Form F of Compound 1 has an X-ray powder diffraction pattern which comprises at least one peak selected from the group consisting of 4.2, 8.5, 12.7, 15.3, 18.5, 19.5, 21.3, 22.5, 25.9, and 29.9±0.2° 2θ. In some embodiments, the solid Form F of Compound 1 has an X-ray powder diffraction pattern which comprises one, two, three, four, and/or five peaks selected from the group consisting of 4.2, 8.5, 12.7, 15.3, 18.5, 19.5, 21.3, 22.5, 25.9, and 29.9±0.2° 2θ.

In another aspect, provided herein, is a method of preparing solid Form F of Compound 1:

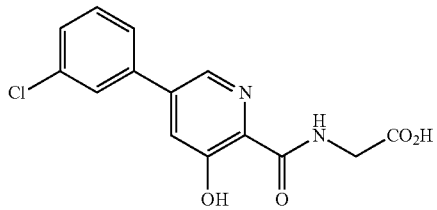 [SMILES: O=C(O)CNC(=O)c1ncc(-c2cccc(Cl)c2)cc1O]

comprising:
a) preparing a solution of Compound 1 in ethanol/water;
b) bringing the solution to super-saturation to cause formation of solid Form F of Compound 1; and
c) isolating solid Form F of Compound 1.

In some embodiments of the method, solid Form F of Compound 1 has an X-ray powder diffraction pattern comprising peaks at 8.5, 15.3, 18.5, 21.2, and 22.5±0.2° 2θ. In other embodiments of the method, solid Form F of Compound 1 has an X-ray powder diffraction pattern comprising peaks at 4.2, 12.7, 19.5, 25.9, and 29.9±0.2° 2θ. In other embodiments of the method, solid Form F of Compound 1 has an X-ray powder diffraction pattern comprising peaks at 4.2, 8.5, 15.3, 18.5, 21.3, and 22.5±0.2° 2θ.

In some embodiments of the method, solid Form F of Compound 1 has an X-ray powder diffraction pattern which comprises at least one peak selected from the group consisting of 4.2, 8.5, 12.7, 15.3, 18.5, 19.5, 21.3, 22.5, 25.9, and 29.9±0.2° 2θ. In some embodiments of the method, solid Form F of Compound 1 has an X-ray powder diffraction pattern which comprises one, two, three, four, five, and/or six peaks selected from the group consisting of 4.2, 8.5, 12.7, 15.3, 18.5, 19.5, 21.3, 22.5, 25.9, and 29.9±0.2° 2θ.

In some embodiments of the method, the solid Form F of Compound 1 has a DSC endotherm onset temperature at about 173.4° C.

In another aspect, provided herein, is solid Form $H_B$ of Compound 1:

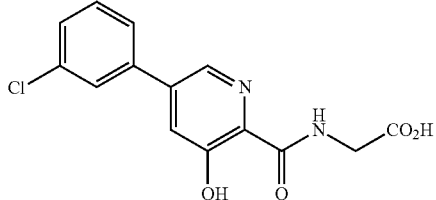 [SMILES: O=C(O)CNC(=O)c1ncc(-c2cccc(Cl)c2)cc1O]

which has an X-ray powder diffraction pattern comprising peaks at 14.6, 15.3, 18.5, 20.4, and 28.1±0.2° 2θ.

In another aspect, provided herein, is solid Form $H_B$ of Compound 1:

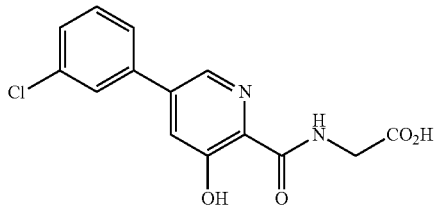 [SMILES: O=C(O)CNC(=O)c1ncc(-c2cccc(Cl)c2)cc1O]

which has an X-ray powder diffraction pattern comprising peaks at 16.0, 20.4, 26.8, 28.1, and 29.6±0.2° 2θ.

In another aspect, provided herein, is solid Form $H_B$ of Compound 1:

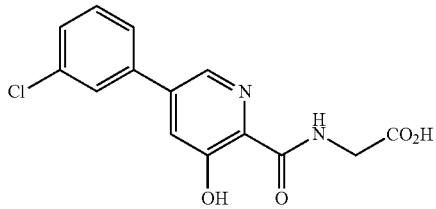 [SMILES: O=C(O)CNC(=O)c1ncc(-c2cccc(Cl)c2)cc1O]

which has an X-ray powder diffraction pattern comprising peaks at 7.9, 14.6, 16.0, 17.6, and 28.1±0.2° 2θ.

In embodiments, the solid Form $H_B$ of Compound 1 is a crystalline form.

In embodiments, the solid Form $H_B$ of Compound 1 is a hydrate.

In embodiments, the solid Form $H_B$ of Compound 1 has DSC endotherm peak temperatures at about 61.0° C., 74.4° C. and 174.8° C.

In embodiments, the solid Form $H_B$ of Compound 1 has DSC endotherm onset temperatures at about 57.3° C., 69.0° C. and 173.7° C.

In another aspect, provided herein, is solid Form $H_B$ of Compound 1:

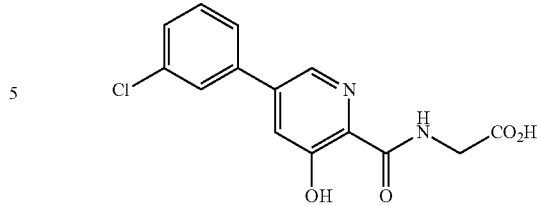

which has an X-ray powder diffraction pattern substantially in accordance with FIG. 13.

In another aspect, provided herein, is solid Form $H_B$ of Compound 1:

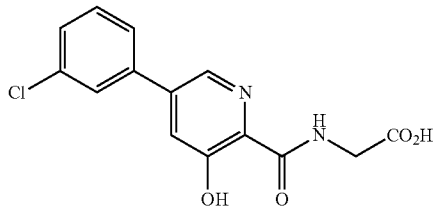 [SMILES: O=C(O)CNC(=O)c1ncc(-c2cccc(Cl)c2)cc1O]

which is prepared by crystallization from a solution comprising methanol and Compound 1; wherein the solid Form $H_B$ of Compound 1 has an X-ray powder diffraction pattern comprising peaks at 14.6, 15.3, 18.5, 20.4, and 28.1±0.2° 2θ, at 7.9, 14.6, 16.0, 17.6, and 28.1±0.2° 2θ, or at 16.0, 20.4, 26.8, 28.1, and 29.6±0.2° 2θ. In some embodiments, the solid Form $H_B$ of Compound 1 has an X-ray powder diffraction pattern which comprises at least one peak selected from the group consisting of 7.9, 14.6, 15.3, 16.0, 17.6, 18.5, 20.4, 26.8, 28.1, and 29.6±0.2° 2θ. In some embodiments, the solid Form $H_B$ of Compound 1 has an X-ray powder diffraction pattern which comprises one, two, three, four, and/or five peaks selected from the group consisting of 7.9, 14.6, 15.3, 16.0, 17.6, 18.5, 20.4, 26.8, 28.1, and 29.6±0.2° 2θ.

In another aspect, provided herein, is a method of preparing solid Form $H_B$ of Compound 1:

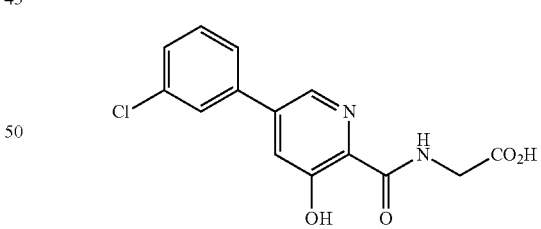

comprising:
a) preparing a solution of Compound 1 in methanol;
b) bringing the solution to super-saturation to cause formation of solid Form $H_B$ of Compound 1; and
c) isolating solid Form $H_B$ of Compound 1.

In some embodiments of the method, solid Form $H_B$ of Compound 1 has an X-ray powder diffraction pattern comprising peaks at 14.6, 15.3, 18.5, 20.4, and 28.1±0.2° 2θ. In other embodiments of the method, solid Form $H_B$ of Compound 1 has an X-ray powder diffraction pattern comprising peaks at 16.0, 20.4, 26.8, 28.1, and 29.6±0.2° 2θ. In other embodiments of the method, solid Form $H_B$ of Compound 1 has an X-ray powder diffraction pattern comprising peaks at 7.9, 14.6, 16.0, 17.6, and 28.1±0.2° 2θ.

In some embodiments of the method, solid Form $H_B$ of Compound 1 has an X-ray powder diffraction pattern which comprises at least one peak selected from the group consisting of 7.9, 14.6, 16.0, 15.3, 17.6, 18.5, 20.4, 26.8, 28.1, and 29.6±0.2° 2θ. In some embodiments of the method, solid Form $H_B$ of Compound 1 has an X-ray powder diffraction pattern comprises one, two, three, four, and/or five peaks selected from the group consisting of 7.9, 14.6, 16.0, 15.3, 17.6, 18.5, 20.4, 26.8, 28.1, and 29.6±0.2° 2θ.

In another aspect, provided herein, is solid Form $S_A$ of Compound 1:

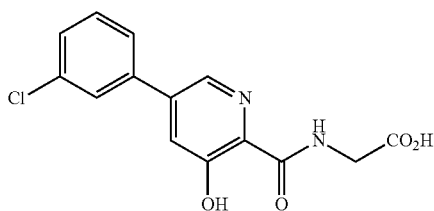 [SMILES: O=C(O)CNC(=O)c1ncc(-c2cccc(Cl)c2)cc1O]

which has an X-ray powder diffraction pattern comprising peaks at 13.1, 17.5, 19.1, 22.7, and 24.6±0.2° 2θ.

In another aspect, provided herein, is solid Form $S_A$ of Compound 1:

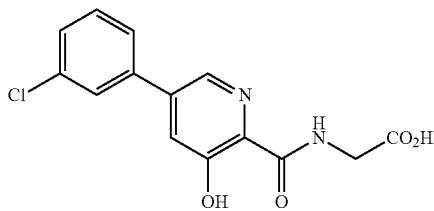 [SMILES: O=C(O)CNC(=O)c1ncc(-c2cccc(Cl)c2)cc1O]

which has an X-ray powder diffraction pattern comprising peaks at 13.1, 17.5, 19.1, 32.0, and 35.3±0.2° 2θ.

In another aspect, provided herein, is solid Form $S_A$ of Compound 1:

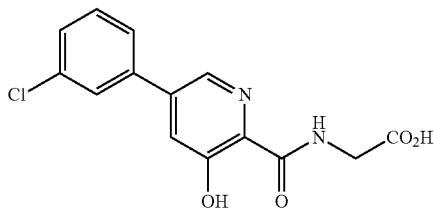 [SMILES: O=C(O)CNC(=O)c1ncc(-c2cccc(Cl)c2)cc1O]

which has an X-ray powder diffraction pattern comprising peaks at 13.1, 17.5, 19.1, 24.6, and 32.0±0.2° 2θ.

In another aspect, provided herein, is solid Form $S_A$ of Compound 1:

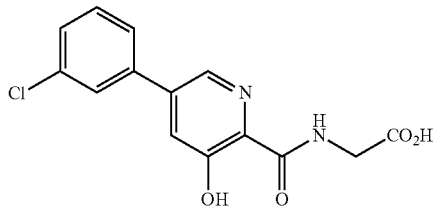 [SMILES: O=C(O)CNC(=O)c1ncc(-c2cccc(Cl)c2)cc1O]

which has an X-ray powder diffraction pattern which comprises at least one peak selected from the group consisting of 13.1, 17.5, 19.1, 22.7, 24.6, 32.0, and 35.3±0.2° 2θ. In some embodiments, the solid Form $S_A$ of Compound 1 which comprises one, two, three, four, and/or five peaks selected from the group consisting of 13.1, 17.5, 19.1, 22.7, 24.6, 32.0, and 35.3±0.2° 2θ.

In embodiments, the solid Form $S_A$ of Compound 1 is a crystalline form.

In embodiments, the solid Form $S_A$ of Compound 1 is a 1,4-dioxane solvate. In some embodiments, the molar ratio of Compound 1 to 1,4-dioxane of about 1:1.2.

In embodiments, the solid Form $S_A$ of Compound 1 has DSC endotherm peak temperature at about 78.1° C. and 174.6° C.

In embodiments, the solid Form $S_A$ of Compound 1 has DSC endotherm onset temperature at about 75.0° C. and 173.9° C.

In embodiments, the solid Form $S_A$ of Compound 1 has a thermogravimetric weight loss of 19.3%.

In another aspect, provided herein, is solid Form $S_A$ of Compound 1:

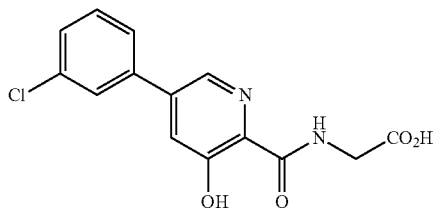 [SMILES: O=C(O)CNC(=O)c1ncc(-c2cccc(Cl)c2)cc1O]

which has an X-ray powder diffraction pattern substantially in accordance with FIG. 16.

In another aspect, provided herein, is solid Form $S_A$ of Compound 1:

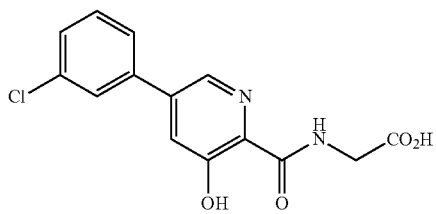 [SMILES: O=C(O)CNC(=O)c1ncc(-c2cccc(Cl)c2)cc1O]

which is prepared by crystallization from a solution comprising 1,4-dioxane and Compound 1; wherein the solid Form $S_A$ of Compound 1 has an X-ray powder diffraction pattern comprising peaks at 13.1, 17.5, 19.1, 22.7, and 24.6±0.2° 2θ, at 13.1, 17.5, 19.1, 32.0, and 35.3±0.2° 2θ, or at 13.1, 17.5, 19.1, 24.6, and 32.0±0.2° 2θ. In some embodiments, the solid Form $S_A$ of Compound 1 has an X-ray powder diffraction pattern which comprises at least one peak selected from the group consisting of 13.1, 17.5, 19.1, 22.7, 24.6, 32.0, and 35.3±0.2° 2θ. In some embodiments, the solid Form $S_A$ of Compound 1 has an X-ray powder diffraction pattern which comprises one, two, three, four, and/or five peaks selected from the group consisting of 13.1, 17.5, 19.1, 22.7, 24.6, 32.0, and 35.3±0.2° 2θ.

A method of preparing solid Form $S_A$ of Compound 1:

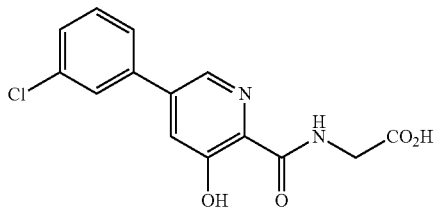 [SMILES: O=C(O)CNC(=O)c1ncc(-c2cccc(Cl)c2)cc1O]

comprising:
a) preparing a solution of Compound 1 in 1,4-dioxane;
b) bringing the solution to super-saturation to cause formation of solid Form $S_A$ of Compound 1; and
c) isolating solid Form $S_A$ of Compound 1.

In embodiments of the method, solid Form $S_A$ of Compound 1 has an X-ray powder diffraction pattern comprising peaks at 13.1, 17.5, 19.1, 22.7, and 24.6±0.2° 2θ. In other embodiments of the method, solid Form $S_A$ of Compound 1 has an X-ray powder diffraction pattern comprising peaks at 13.1, 17.5, 19.1, 32.0, and 35.3±0.2° 2θ. In other embodiments of the method, solid Form $S_A$ of Compound 1 has an X-ray powder diffraction pattern comprising peaks at 13.1, 17.5, 19.1, 24.6, and 32.0±0.2° 2θ. In some embodiments of the method, the solid Form $S_A$ of Compound 1 has an X-ray powder diffraction pattern which comprises at least one peak selected from the group consisting of 13.1, 17.5, 19.1, 22.7, 24.6, 32.0, and 35.3±0.2° 2θ. In some embodiments of the method, the solid Form $S_A$ of Compound 1 has an X-ray powder diffraction pattern which comprises one, two, three, four, and/or five peaks selected from the group consisting of 13.1, 17.5, 19.1, 22.7, 24.6, 32.0, and 35.3±0.2° 2θ.

In embodiments of the method, the solid Form $S_A$ of Compound 1 is a 1,4-dioxane solvate. In some embodiments of the method, the molar ratio of Compound 1 to 1,4-dioxane of about 1:1.2.

In embodiments of the method, the solid Form $S_A$ of Compound 1 has DSC endotherm onset temperature at about 75.0° C. and 173.9° C.

In embodiments of the method, the solid Form $S_A$ of Compound 1 has a thermogravimetric weight loss of 19.3%.

In another aspect, provided herein, is solid Form $S_B$ of Compound 1:

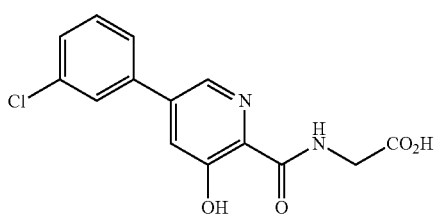 [SMILES: O=C(O)CNC(=O)c1ncc(-c2cccc(Cl)c2)cc1O]

which has an X-ray powder diffraction pattern comprising peaks at 14.0, 19.6, 20.0, 22.0, and 28.5±0.2° 2θ.

In another aspect, provided herein, is solid Form $S_B$ of Compound 1:

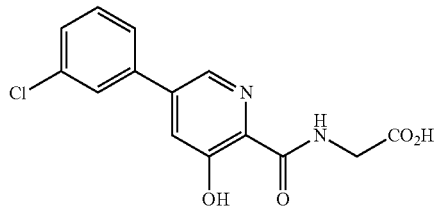 [SMILES: O=C(O)CNC(=O)c1ncc(-c2cccc(Cl)c2)cc1O]

which has an X-ray powder diffraction pattern comprising peaks at 14.0, 19.6, 20.0, 31.5, and 33.6±0.2° 2θ.

In another aspect, provided herein, is solid Form $S_B$ of Compound 1:

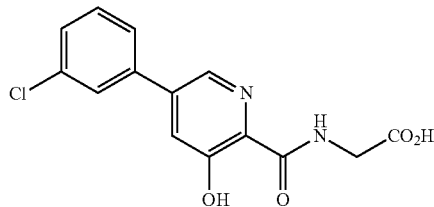 [SMILES: O=C(O)CNC(=O)c1ncc(-c2cccc(Cl)c2)cc1O]

which has an X-ray powder diffraction pattern comprising peaks at 6.8, 14.0, 17.3, 19.6, 20.0, and 28.5±0.2° 2θ.

In another aspect, provided herein, is solid Form $S_B$ of Compound 1:

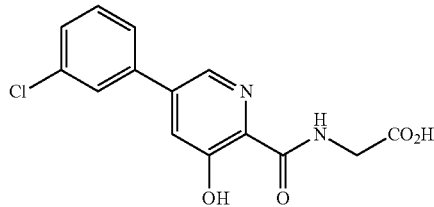 [SMILES: O=C(O)CNC(=O)c1ncc(-c2cccc(Cl)c2)cc1O]

which has an X-ray powder diffraction pattern which comprises at least one peak selected from the group consisting of 6.8, 14.0, 17.3, 19.6, 20.0, 22.0, 28.5, 31.5, and 33.6±0.2° 2θ. In some embodiments, the solid Form $S_B$ of Compound 1 has an X-ray powder diffraction pattern which comprises one, two, three, four, five, and/or six peaks selected from the group consisting of 6.8, 14.0, 17.3, 19.6, 20.0, 22.0, 28.5, 31.5, and 33.6±0.2° 2θ.

In embodiments, the solid Form $S_B$ of Compound 1 is a crystalline form.

In embodiments, the solid Form $S_B$ of Compound 1 is a 1,4-dioxane solvate. In some embodiments, the molar ratio of Compound 1 to 1,4-dioxane of about 1:1.4.

In embodiments, the solid Form $S_B$ of Compound 1 has DSC endotherm peak temperatures at about 80.7° C. and 175.2° C.

In embodiments, the solid Form $S_B$ of Compound 1 has DSC endotherm onset temperatures at about 79.5° C. and 173.9° C.

In embodiments, the solid Form $S_B$ of Compound 1 has a thermogravimetric weight loss of 20.7%.

In another aspect, provided herein, is solid Form $S_B$ of Compound 1:

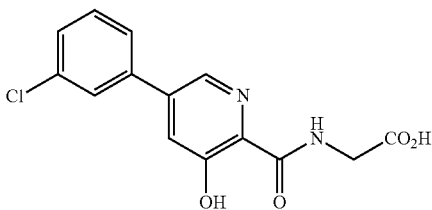 [SMILES: O=C(O)CNC(=O)c1ncc(-c2cccc(Cl)c2)cc1O]

which has an X-ray powder diffraction pattern substantially in accordance with FIG. 19.

In another aspect, provided herein, is solid Form $S_B$ of Compound 1:

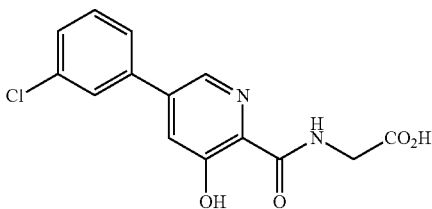 [SMILES: O=C(O)CNC(=O)c1ncc(-c2cccc(Cl)c2)cc1O]

which is prepared by crystallization from a solution comprising 1,4-dioxane and Compound 1; wherein the solid Form $S_B$ of Compound 1 has an X-ray powder diffraction pattern comprising peaks at 14.0, 19.6, 20.0, 22.0, and 28.5±0.2° 2θ or at 14.0, 19.6, 20.0, 31.5, and 33.6±0.2° 2θ. In some embodiments, the solid Form $S_B$ of Compound 1 has an X-ray powder diffraction pattern which comprises at least one peak selected from the group consisting of 14.0, 19.6, 20.0, 22.0, 28.5, 31.5, and 33.6±0.2° 2θ. In some embodiments, the solid Form $S_B$ of Compound 1 has an X-ray powder diffraction pattern which comprises at least one peak selected from the group consisting of 6.8, 14.0, 17.3, 19.6, 20.0, and 28.5±0.2° 2θ. In some embodiments, the solid Form $S_B$ of Compound 1 has an X-ray powder diffraction pattern which comprises one, two, three, four, five, and/or six peaks selected from the group consisting of 6.8, 14.0, 17.3, 19.6, 20.0, 22.0, 28.5, 31.5, and 33.6±0.2° 2θ.

In another aspect, provided herein, is a method of preparing solid Form $S_B$ of Compound 1:

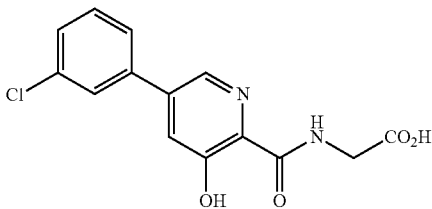 [SMILES: O=C(O)CNC(=O)c1ncc(-c2cccc(Cl)c2)cc1O]

comprising:
a) preparing a solution of Compound 1 in 1,4-dioxane;
b) bringing the solution to super-saturation to cause formation of solid Form $S_B$ of Compound 1; and
c) isolating solid Form $S_B$ of Compound 1.

In some embodiments, the method further comprises adding anti solvent to the solution of Compound 1 and/or fast cooling to about 0° C. In some embodiments, the method further comprises adding about 1-5 folds of anti solvent to the solution of Compound 1 and/or fast cooling to about 0° C. In some embodiments of the method, the anti solvent is heptane.

In some embodiments of the method, solid Form $S_B$ of Compound 1 has an X-ray powder diffraction pattern comprising peaks at 14.0, 19.6, 20.0, 22.0, and 28.5±0.2° 2θ. In other embodiments of the method, solid Form $S_B$ of Compound 1 has an X-ray powder diffraction pattern comprising peaks at 14.0, 19.6, 20.0, 31.5, and 33.6±0.2° 2θ. In other embodiments of the method, solid Form $S_B$ of Compound 1 has an X-ray powder diffraction pattern comprising peaks at 6.8, 14.0, 17.3, 19.6, 20.0, and 28.5±0.2° 2θ. In some embodiments of the method, solid Form $S_B$ of Compound 1 has an X-ray powder diffraction pattern which comprises at least one peak selected from the group consisting of 6.8, 14.0, 17.3, 19.6, 20.0, 22.0, 28.5, 31.5, and 33.6±0.2° 2θ. In some embodiments of the method, solid Form $S_B$ of Compound 1 has an X-ray powder diffraction pattern which comprises one, two, three, four, five, and/or six peaks selected from the group consisting of 6.8, 14.0, 17.3, 19.6, 20.0, 22.0, 28.5, 31.5, and 33.6±0.2° 2θ.

In embodiments of the method, the solid Form $S_B$ of Compound 1 is a 1,4-dioxane solvate. In some embodiments of the method, the molar ratio of Compound 1 to 1,4-dioxane of about 1:1.4.

In embodiments of the method, the solid Form $S_B$ of Compound 1 has DSC endotherm onset temperatures at about 79.5° C. and 173.9° C.

In embodiments of the method, the solid Form $S_B$ of Compound 1 has a thermogravimetric weight loss of 20.7%.

In another aspect, provided herein, is solid Form $S_C$ of Compound 1:

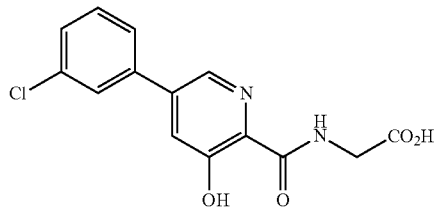 [SMILES: O=C(O)CNC(=O)c1ncc(-c2cccc(Cl)c2)cc1O]

which has an X-ray powder diffraction pattern comprising peaks at 11.1, 15.1, 18.6, 22.1, and 26.4±0.2° 2θ.

In another aspect, provided herein, is solid Form $S_C$ of Compound 1:

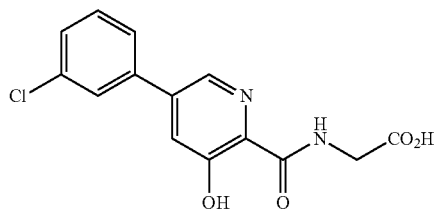 [SMILES: O=C(O)CNC(=O)c1ncc(-c2cccc(Cl)c2)cc1O]

which has an X-ray powder diffraction pattern comprising peaks at 4.8, 9.5, 11.1, 21.8, and 34.8±0.2° 2θ.

In another aspect, provided herein, is solid Form $S_C$ of Compound 1:

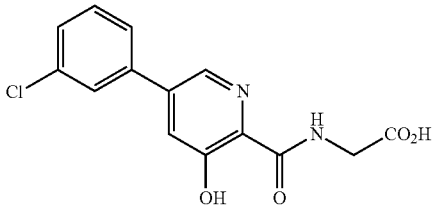 [SMILES: O=C(O)CNC(=O)c1ncc(-c2cccc(Cl)c2)cc1O]

which has an X-ray powder diffraction pattern comprising peaks at 4.8, 7.9, 14.3, 18.6, 21.1, and 22.1±0.2° 2θ

In another aspect, provided herein, is solid Form $S_C$ of Compound 1:

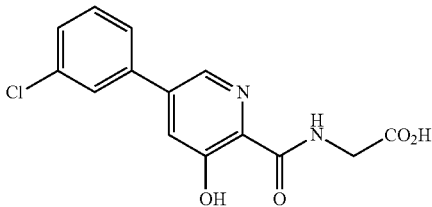 [SMILES: O=C(O)CNC(=O)c1ncc(-c2cccc(Cl)c2)cc1O]

which has an X-ray powder diffraction pattern which comprises at least one peak selected from the group consisting of 4.8, 7.9, 9.5, 11.1, 14.3, 15.1, 18.6, 21.1, 21.8, 22.1, 26.4, and 34.8±0.2° 2θ. In some embodiments, the solid Form $S_C$ of Compound 1 has an X-ray powder diffraction pattern which comprises one, two, three, four, five, and/or six peaks selected from the group consisting of 4.8, 7.9, 9.5, 11.1, 14.3, 15.1, 18.6, 21.1, 21.8, 22.1, 26.4, and 34.8±0.2° 2θ.

In embodiments, the solid Form $S_C$ of Compound 1 is a crystalline form.

In embodiments, the solid Form $S_C$ of Compound 1 is a 1,4-dioxane solvate. In some embodiments, the molar ratio of Compound 1 to 1,4-dioxane of about 1:0.6.

In embodiments, the solid Form $S_C$ of Compound 1 has DSC endotherm peak temperatures at about 66.7° C. and 173.2° C.

In embodiments, the solid Form $S_C$ of Compound 1 has DSC endotherm onset temperatures at about 65.0° C. and 171.0° C.

In embodiments, the solid Form $S_C$ of Compound 1 has a thermogravimetric weight loss of 16.4%.

In another aspect, provided herein, is solid Form $S_C$ of Compound 1:

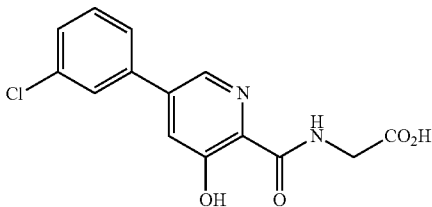 [SMILES: O=C(O)CNC(=O)c1ncc(-c2cccc(Cl)c2)cc1O]

which has an X-ray powder diffraction pattern substantially in accordance with FIG. 22.

In another aspect, provided herein, is solid Form $S_C$ of Compound 1:

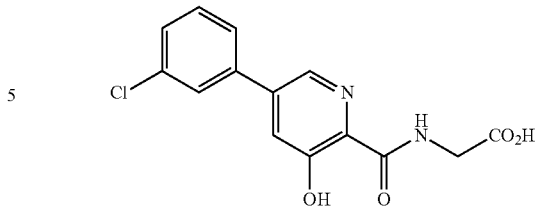

which is prepared by crystallization from a solution comprising 1,4-dioxane and Compound 1; wherein the solid Form $S_C$ of Compound 1 has an X-ray powder diffraction pattern comprising peaks at 11.1, 15.1, 18.6, 22.1, and 26.4±0.2° 2θ or at 4.8, 9.5, 11.1, 21.8, and 34.8±0.2° 2θ. In some embodiments, the solid Form $S_C$ of Compound 1 has an X-ray powder diffraction pattern comprising peaks at 4.8, 7.9, 14.3, 18.6, 21.1, and 22.1±0.2° 2θ. In some embodiments, the solid Form $S_C$ of Compound 1 has an X-ray powder diffraction pattern which comprises at least one peak selected from the group consisting of 4.8, 7.9, 9.5, 11.1, 14.3, 15.1, 18.6, 21.1, 21.8, 22.1, 26.4, and 34.8±0.2° 2θ. In some embodiments, the solid Form $S_C$ of Compound 1 has an X-ray powder diffraction pattern which comprises one, two, three, four, five, and/or six peaks selected from the group consisting of 4.8, 7.9, 9.5, 11.1, 14.3, 15.1, 18.6, 21.1, 21.8, 22.1, 26.4, and 34.8±0.2° 2θ.

In another aspect, provided herein, is a method of preparing solid Form $S_C$ of Compound 1:

comprising:
a) preparing a solution of Compound 1 in 1,4-dioxane;
b) bringing the solution to super-saturation to cause formation of solid Form $S_C$ of Compound 1; and
c) isolating solid Form $S_C$ of Compound 1.

In embodiments, the method further comprises slow cooling the solution to about 0° C.

In some embodiments of the method, solid Form $S_C$ of Compound 1 has an X-ray powder diffraction pattern comprising peaks at 11.1, 15.1, 18.6, 22.1, and 26.4±0.2° 2θ. In other embodiments of the method, solid Form $S_C$ of Compound 1 has an X-ray powder diffraction pattern comprising peaks at 4.8, 9.5, 11.1, 21.8, and 34.8±0.2° 2θ. In other embodiments of the method, solid Form $S_C$ of Compound 1 has an X-ray powder diffraction pattern comprising peaks at 4.8, 7.9, 14.3, 18.6, 21.1, and 22.1±0.2° 2θ. In some embodiments of the method, solid Form $S_C$ of Compound 1 has an X-ray powder diffraction pattern which comprises at least one peak selected from the group consisting of 4.8, 7.9, 9.5, 11.1, 14.3, 15.1, 18.6, 21.1, 21.8, 22.1, 26.4, and 34.8±0.2° 2θ. In some embodiments of the method, solid Form $S_C$ of Compound 1 has an X-ray powder diffraction pattern which comprises one, two, three, four, five, and/or six peaks selected from the group consisting of 4.8, 7.9, 9.5, 11.1, 14.3, 15.1, 18.6, 21.1, 21.8, 22.1, 26.4, and 34.8±0.2° 2θ.

In embodiments of the method, the solid Form $S_C$ of Compound 1 is a 1,4-dioxane solvate. In some embodiments of the method, the molar ratio of Compound 1 to 1,4-dioxane of about 1:0.6

In embodiments of the method, the solid Form $S_C$ of Compound 1 has DSC endotherm onset temperatures at about 65.0° C. and 171.0° C.

In embodiments of the method, the solid Form $S_C$ of Compound 1 has a thermogravimetric weight loss of 16.4%.

In another aspect, provided herein, is solid Form $S_D$ of Compound 1:

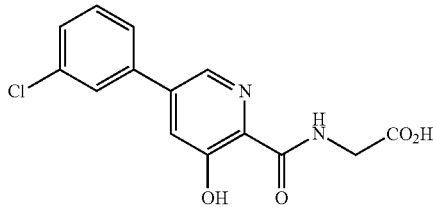 [SMILES: O=C(O)CNC(=O)c1ncc(-c2cccc(Cl)c2)cc1O]

which has an X-ray powder diffraction pattern comprising peaks at 17.0, 24.0, 25.5, 26.2 and 28.4±0.2° 2θ.

In another aspect, provided herein, is solid Form $S_D$ of Compound 1:

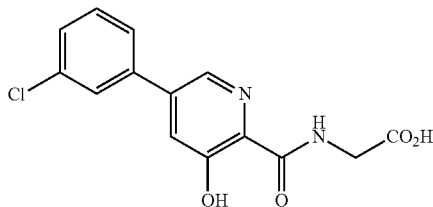 [SMILES: O=C(O)CNC(=O)c1ncc(-c2cccc(Cl)c2)cc1O]

which has an X-ray powder diffraction pattern comprising peaks at 12.1, 14.5, 25.5, 29.2, and 36.2±0.2° 2θ.

In another aspect, provided herein, is solid Form $S_D$ of Compound 1:

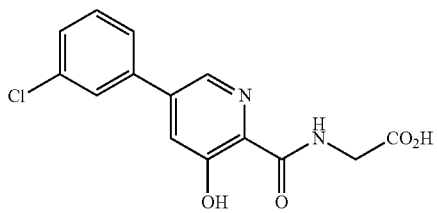 [SMILES: O=C(O)CNC(=O)c1ncc(-c2cccc(Cl)c2)cc1O]

which has an X-ray powder diffraction pattern comprising peaks at 12.1, 17.0, 24.0, 25.5, and 26.2±0.2° 2θ.

In another aspect, provided herein, is solid Form $S_D$ of Compound 1:

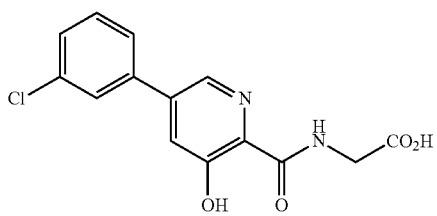 [SMILES: O=C(O)CNC(=O)c1ncc(-c2cccc(Cl)c2)cc1O]

which has an X-ray powder diffraction pattern which comprises at least one peak selected from the group consisting of 12.1, 14.5, 17.0, 24.0, 25.5, 26.2, 29.2, and 36.2±0.2° 2θ. In some embodiments, the solid Form $S_D$ of Compound 1 has an X-ray powder diffraction pattern which comprises one, two, three, four, and/or five peaks selected from the group consisting of 12.1, 14.5, 17.0, 24.0, 25.5, 26.2, 29.2, and 36.2±0.2° 2θ.

In embodiments, the solid Form $S_D$ of Compound 1 is a crystalline form.

In embodiments, the solid Form $S_D$ of Compound 1 is an anisole solvate. In some embodiments, the molar ratio of Compound 1 to anisole of about 1:0.7.

In embodiments, the solid Form $S_D$ of Compound 1 has DSC endotherm peak temperatures at about 105.2° C. and 175.3° C.

In embodiments, the solid Form $S_D$ of Compound 1 has DSC endotherm onset temperatures at about 96.2° C. and 174.3° C.

In embodiments, the solid Form $S_D$ of Compound 1 has a thermogravimetric weight loss of 14.0%.

In another aspect, provided herein, is solid Form $S_D$ of Compound 1:

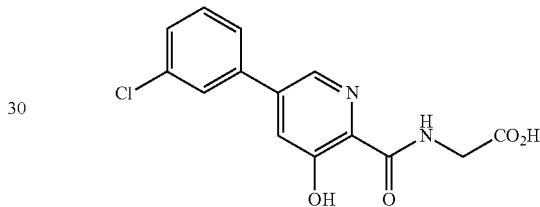

which has an X-ray powder diffraction pattern substantially in accordance with FIG. 25.

In another aspect, provided herein, is solid Form $S_D$ of Compound 1:

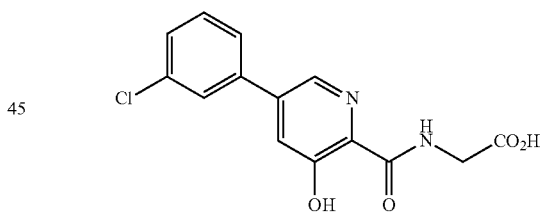

which is prepared by crystallization from a solution comprising anisole and Compound 1; wherein the solid Form $S_D$ of Compound 1 has an X-ray powder diffraction pattern comprising peaks at 17.0, 24.0, 25.5, 26.2 and 28.4±0.2° 2θ or at 12.1, 14.5, 25.5, 29.2, and 36.2±0.2° 2θ. In some embodiments, the solid Form $S_D$ of Compound 1 has an X-ray powder diffraction pattern comprising peaks at 12.1, 17.0, 24.0, 25.5, and 26.2±0.2° 2θ. In some embodiments, the solid Form $S_D$ of Compound 1 has an X-ray powder diffraction pattern which comprises at least one peak selected from the group consisting of 12.1, 14.5, 17.0, 24.0, 25.5, 26.2, 28.4, 29.2, and 36.2±0.2° 2θ. In some embodiments, the solid Form $S_D$ of Compound 1 has an X-ray powder diffraction pattern which comprises one, two, three, four, and/or five peaks selected from the group consisting of 12.1, 14.5, 17.0, 24.0, 25.5, 26.2, 28.4, 29.2, and 36.2±0.2° 2θ.

In another aspect, provided herein, is a method of preparing solid Form $S_D$ of Compound 1:

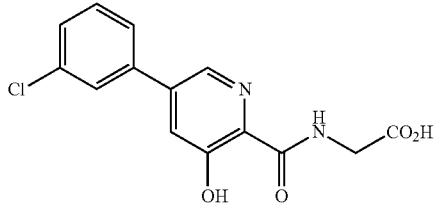 [SMILES: O=C(O)CNC(=O)c1ncc(-c2cccc(Cl)c2)cc1O]

comprising:
a) preparing a solution of Compound 1 in anisole;
b) bringing the solution to super-saturation to cause formation of solid Form $S_D$ of Compound 1; and
c) isolating solid Form $S_D$ of Compound 1.

In embodiments, the method further comprises equilibrating the solution at room temperature or at about 5° C.

In some embodiments of the method, solid Form $S_D$ of Compound 1 has an X-ray powder diffraction pattern comprising peaks at 17.0, 24.0, 25.5, 26.2, and 28.4±0.2° 2θ. In other embodiments of the method, solid Form $S_D$ of Compound 1 has an X-ray powder diffraction pattern comprising peaks at 12.1, 14.5, 25.5, 29.2, and 36.2±0.2° 2θ. In other embodiments of the method, solid Form $S_D$ of Compound 1 has an X-ray powder diffraction pattern comprising peaks at 12.1, 17.0, 24.0, 25.5, and 26.2±0.2° 2θ. In some embodiments of the method, solid Form $S_D$ of Compound 1 has an X-ray powder diffraction pattern which comprises at least one peak selected from the group consisting of 12.1, 14.5, 17.0, 24.0, 25.5, 26.2, 29.2, 28.4, 29.2, and 36.2±0.2° 2θ. In some embodiments of the method, solid Form $S_D$ of Compound 1 has an X-ray powder diffraction pattern which comprises one, two, three, four, and/or five peaks selected from the group consisting of 12.1, 14.5, 17.0, 24.0, 25.5, 26.2, 29.2, 28.4, 29.2, and 36.2±0.2° 2θ.

In embodiments of the method, the solid Form $S_D$ of Compound 1 is an anisole solvate. In some embodiments of the method, the molar ratio of Compound 1 to anisole of about 1:0.7.

In embodiments of the method, the solid Form $S_D$ of Compound 1 has DSC endotherm onset temperatures at about 96.2° C. and 174.3° C.

In embodiments of the method, the solid Form $S_D$ of Compound 1 has a thermogravimetric weight loss of 14.0%.

In another aspect, provided herein, is solid Form $S_E$ of Compound 1:

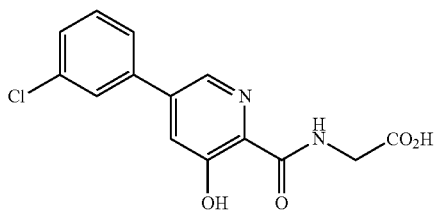 [SMILES: O=C(O)CNC(=O)c1ncc(-c2cccc(Cl)c2)cc1O]

which has an X-ray powder diffraction pattern comprising peaks at 15.8, 17.0, 24.6, 26.5, and 27.2±0.2° 2θ.

In another aspect, provided herein, is solid Form $S_E$ of Compound 1:

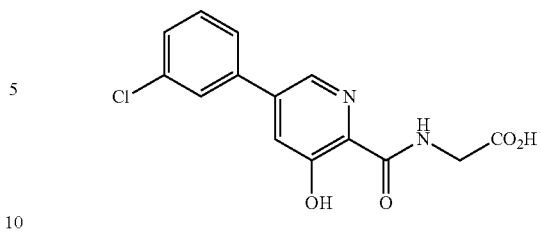

which has an X-ray powder diffraction pattern comprising peaks at 14.5, 17.0, 25.1, 26.5, and 27.2±0.2° 2θ.

In another aspect, provided herein, is solid Form $S_E$ of Compound 1:

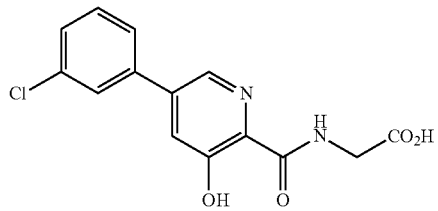 [SMILES: O=C(O)CNC(=O)c1ncc(-c2cccc(Cl)c2)cc1O]

which has an X-ray powder diffraction pattern comprising peaks at 14.5, 15.8, 22.4, 24.6, 26.5, and 27.2±0.2° 2θ.

In another aspect, provided herein, is solid Form $S_E$ of Compound 1:

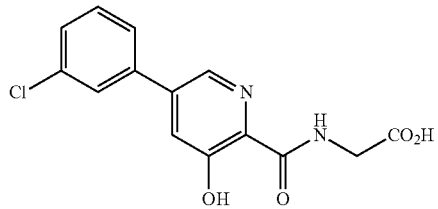 [SMILES: O=C(O)CNC(=O)c1ncc(-c2cccc(Cl)c2)cc1O]

which has an X-ray powder diffraction pattern which comprises at least one peak selected from the group consisting of 14.5, 15.8, 17.0, 22.4, 24.6, 25.1, 26.5, and 27.2±0.2° 2θ. In some embodiments, the solid Form $S_E$ of Compound 1 which has an X-ray powder diffraction pattern which comprises one, two, three, four, five, and/or six peaks selected from the group consisting of 14.5, 15.8, 17.0, 22.4, 24.6, 25.1, 26.5, and 27.2±0.2° 2θ.

In embodiments, the solid Form $S_E$ of Compound 1 is a crystalline form.

In embodiments, the solid Form $S_E$ of Compound 1 is a dimethylacetamide solvate. In some embodiments, the molar ratio of Compound 1 to dimethylacetamide of about 1:1.5.

In embodiments, the solid Form $S_E$ of Compound 1 has DSC endotherm peak temperature at about 80.0° C.

In embodiments, the solid Form $S_E$ of Compound 1 has DSC endotherm onset temperature at about 79.2° C.

In another aspect, provided herein, is solid Form $S_E$ of Compound 1:

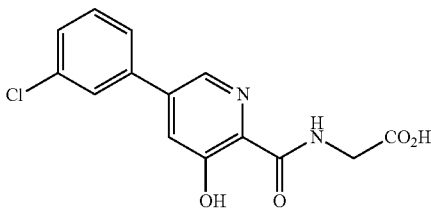 [SMILES: O=C(O)CNC(=O)c1ncc(-c2cccc(Cl)c2)cc1O]

which has an X-ray powder diffraction pattern substantially in accordance with FIG. 28.

In another aspect, provided herein, is solid Form $S_E$ of Compound 1:

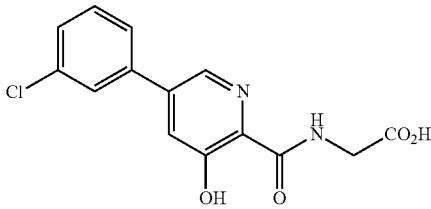 [SMILES: O=C(O)CNC(=O)c1ncc(-c2cccc(Cl)c2)cc1O]

which is prepared by crystallization from a solution comprising dimethylacetamide and Compound 1; wherein the solid Form $S_E$ of Compound 1 has an X-ray powder diffraction pattern comprising peaks at 15.8, 17.0, 24.6, 26.5, and 27.2±0.2° 2θ or at 14.5, 17.0, 25.1, 26.5, and 27.2±0.2° 2θ. In some embodiments, the solid Form $S_E$ of Compound 1 has an X-ray powder diffraction pattern comprising peaks at 14.5, 15.8, 22.4, 24.6, 26.5, and 27.2±0.2° 2θ. In some embodiments, the solid Form $S_E$ of Compound 1 has an X-ray powder diffraction pattern which comprises at least one peak selected from the group consisting of 14.5, 15.8, 17.0, 22.4, 24.6, 25.1, 26.5, and 27.2±0.2° 2θ. In some embodiments, the solid Form $S_E$ of Compound 1 has an X-ray powder diffraction pattern which comprises one, two, three, four, and/or five peaks selected from the group consisting of 14.5, 15.8, 17.0, 22.4, 24.6, 25.1, 26.5, and 27.2±0.2° 2θ.

In another aspect, provided herein, is a method of preparing solid Form $S_E$ of Compound 1:

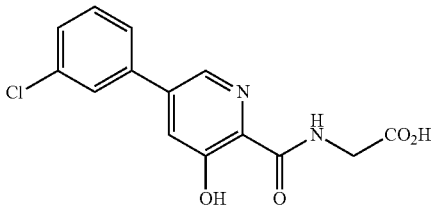 [SMILES: O=C(O)CNC(=O)c1ncc(-c2cccc(Cl)c2)cc1O]

comprising:
a) preparing a solution of Compound 1 in dimethylacetamide;
b) bringing the solution to super-saturation to cause formation of solid Form $S_E$ of Compound 1; and
c) isolating solid Form $S_E$ of Compound 1.

In embodiments, the method further comprises equilibrating the solution at about 25° C.

In some embodiments of the method, solid Form $S_E$ of Compound 1 has an X-ray powder diffraction pattern comprising peaks at 15.8, 17.0, 24.6, 26.5, and 27.2±0.2° 2θ. In other embodiments of the method, solid Form $S_E$ of Compound 1 has an X-ray powder diffraction pattern comprising peaks at 14.5, 17.0, 25.1, 26.5, and 27.2±0.2° 2θ. In other embodiments of the method, solid Form $S_E$ of Compound 1 has an X-ray powder diffraction pattern comprising peaks at 14.5, 15.8, 22.4, 24.6, 26.5, and 27.2±0.2° 2θ. In some embodiments of the method, solid Form $S_E$ of Compound 1 has an X-ray powder diffraction pattern which comprises at least one peak selected from the group consisting of 14.5, 15.8, 17.0, 22.4, 24.6, 25.1, 26.5, and 27.2±0.2° 2θ. In some embodiments of the method, solid Form $S_E$ of Compound 1 has an X-ray powder diffraction pattern which comprises one, two, three, four, five, and/or six peaks selected from the group consisting of 14.5, 15.8, 17.0, 22.4, 24.6, 25.1, 26.5, and 27.2±0.2° 2θ.

In embodiments of the method, the solid Form $S_E$ of Compound 1 is a dimethylacetamide solvate. In some embodiments of the method, the molar ratio of Compound 1 to dimethylacetamide of about 1:1.5.

In embodiments of the method, the solid Form $S_E$ of Compound 1 has DSC endotherm onset temperature at about 79.2° C.

In another aspect, provided herein, is solid Form $S_F$ of Compound 1:

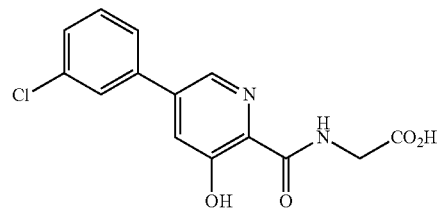 [SMILES: O=C(O)CNC(=O)c1ncc(-c2cccc(Cl)c2)cc1O]

which has an X-ray powder diffraction pattern comprising peaks at 5.9, 11.8, 24.1, 24.3, and 26.2±0.2° 2θ.

In another aspect, provided herein, is solid Form $S_F$ of Compound 1:

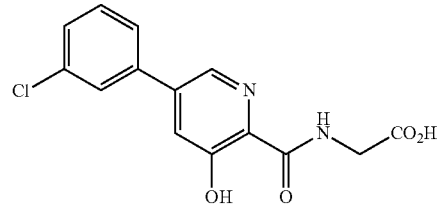 [SMILES: O=C(O)CNC(=O)c1ncc(-c2cccc(Cl)c2)cc1O]

which has an X-ray powder diffraction pattern comprising peaks at 5.9, 11.8, 16.8, 24.1, and 26.9±0.2° 2θ.

In another aspect, provided herein, is solid Form $S_F$ of Compound 1:

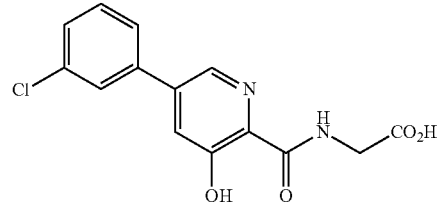 [SMILES: O=C(O)CNC(=O)c1ncc(-c2cccc(Cl)c2)cc1O]

which has an X-ray powder diffraction pattern comprising peaks at 5.9, 11.8, 16.8, 24.3, 26.2, and 26.9±0.2° 2θ.

In another aspect, provided herein, is solid Form $S_F$ of Compound 1:

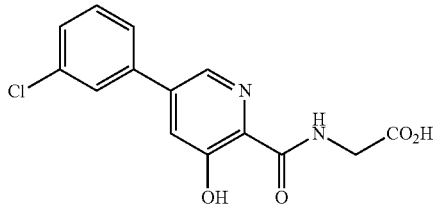 [SMILES: O=C(O)CNC(=O)c1ncc(-c2cccc(Cl)c2)cc1O]

which has an X-ray powder diffraction pattern which comprises at least one peak selected from the group consisting of 5.9, 11.8, 16.8, 24.1, 24.3, 26.2, and 26.9±0.2° 2θ. In some embodiments, the solid Form $S_F$ of Compound 1 has an X-ray powder diffraction pattern which comprises one, two, three, four, five, and/or six peaks selected from the group consisting of 5.9, 11.8, 16.8, 24.1, 24.3, 26.2, and 26.9±0.2° 2θ.

In embodiments, the solid Form $S_F$ of Compound 1 is a crystalline form.

In embodiments, the solid Form $S_F$ of Compound 1 is a dimethylacetamide solvate. In some embodiments, the molar ratio of Compound 1 to dimethylacetamide of about 1:2.5.

In embodiments, the solid Form $S_F$ of Compound 1 has DSC endotherm peak temperatures at about 80.9° C. and 174.1° C.

In embodiments, the solid Form $S_F$ of Compound 1 has DSC endotherm onset temperatures at about 78.2° C. and 173.4° C.

In another aspect, provided herein, is solid Form $S_F$ of Compound 1:

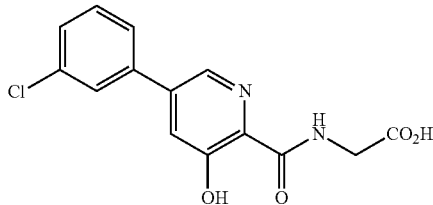 [SMILES: O=C(O)CNC(=O)c1ncc(-c2cccc(Cl)c2)cc1O]

which has an X-ray powder diffraction pattern substantially in accordance with FIG. 31.

In another aspect, provided herein, is solid Form $S_F$ of Compound 1:

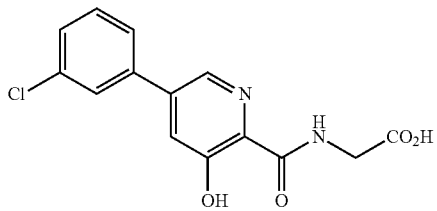 [SMILES: O=C(O)CNC(=O)c1ncc(-c2cccc(Cl)c2)cc1O]

which is prepared by crystallization from a solution comprising dimethylacetamide and Compound 1; wherein the solid Form $S_F$ of Compound 1 has an X-ray diffraction pattern comprising peaks at 5.9, 11.8, 24.1, 24.3, and 26.2±0.2° 2θ or at 5.9, 11.8, 16.8, 24.1, and 26.9±0.2° 2θ. In some embodiments, the solid Form $S_F$ of Compound 1 has an X-ray powder diffraction pattern comprising peaks at 5.9, 11.8, 16.8, 24.3, 26.2, and 26.9±0.2° 2θ. In some embodiments, the solid Form $S_F$ of Compound 1 has an X-ray powder diffraction pattern comprising at least one peak selected from the group consisting of 5.9, 11.8, 16.8, 24.1, 24.3, 26.2, and 26.9±0.2° 2θ.

In another aspect, provided herein, is a method of preparing solid Form $S_F$ of Compound 1:

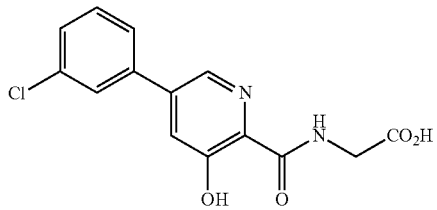 [SMILES: O=C(O)CNC(=O)c1ncc(-c2cccc(Cl)c2)cc1O]

comprising:
a) preparing a solution of Compound 1 in dimethylacetamide;
b) bringing the solution to super-saturation to cause formation of solid Form $S_F$ of Compound 1; and
c) isolating solid Form $S_F$ of Compound 1.

In embodiments, the method further comprises equilibrating the solution at 25° C.

In some embodiments of the method, solid Form $S_F$ of Compound 1 has an X-ray powder diffraction pattern comprising peaks at 5.9, 11.8, 24.1, 24.3, and 26.2±0.2° 2θ. In other embodiments of the method, solid Form $S_F$ of Compound 1 has an X-ray powder diffraction pattern comprising peaks at 5.9, 11.8, 16.8, 24.1, and 26.9±0.2° 2θ. In other embodiments of the method, solid Form $S_F$ of Compound 1 has an X-ray powder diffraction pattern comprising peaks at 5.9, 11.8, 16.8, 24.3, 26.2, and 26.9±0.2° 2θ. In some embodiments, solid Form $S_F$ of Compound 1 has an X-ray powder diffraction pattern which comprises at least one peak selected from the group consisting of 5.9, 11.8, 16.8, 24.1, 24.3, 26.2, and 26.9±0.2° 2θ. In some embodiments, solid Form $S_F$ of Compound 1 has an X-ray powder diffraction pattern which comprises one, two, three, four, five, and/or six peaks selected from the group consisting of 5.9, 11.8, 16.8, 24.1, 24.3, 26.2, and 26.9±0.2° 2θ.

In embodiments of the method, the solid Form $S_F$ of Compound 1 is a dimethylacetamide solvate. In some embodiments of the method, the molar ratio of Compound 1 to dimethylacetamide of about 1:2.5.

In embodiments, the solid Form $S_F$ of Compound 1 has DSC endotherm onset temperatures at about 78.2° C. and 173.4° C.

Also provided herein are pharmaceutical composition comprising any one of the solid forms of Compound 1 disclosed herein (i.e., any one of Form D, Form E, Form F, Form $H_B$, Form $S_A$, Form $S_B$, Form $S_C$, Form $S_D$, Form $S_E$, or Form $S_F$).

Also provided herein are oral dosage form comprising any one of the solid forms of Compound 1 disclosed herein (i.e., any one of Form D, Form E, Form F, Form $H_B$, Form $S_A$, Form $S_B$, Form $S_C$, Form $S_D$, Form $S_E$, or Form $S_F$).

DETAILED DESCRIPTION

Figure 1:
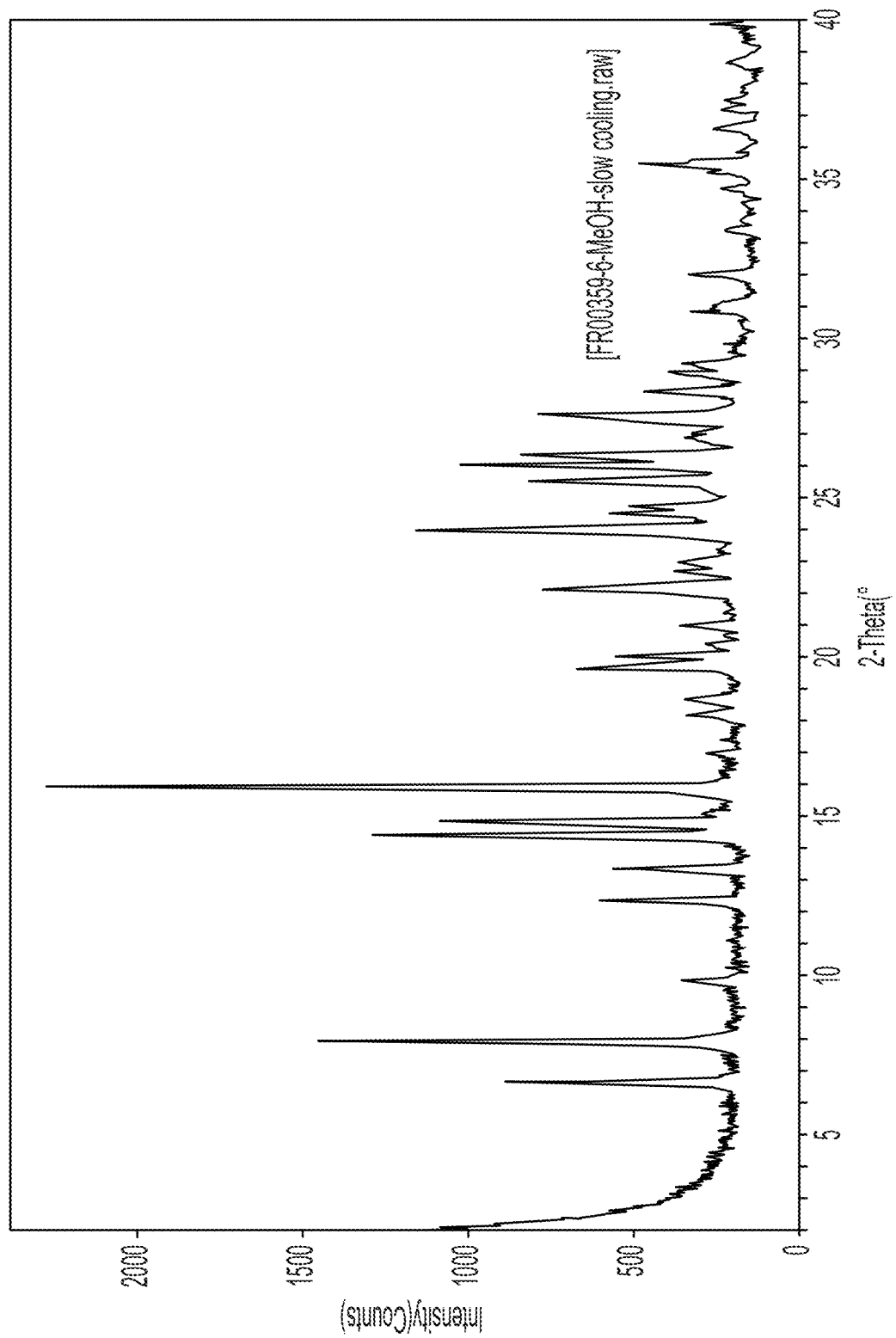
FIG. 1 shows an X-ray powder diffraction (XRPD) analysis of Compound 1, Form D prepared by slow cooling method.

Vadadustat ({[5-(3-chlorophenyl)-3-hydroxypyridine-2-carbonyl]amino}acetic acid; (Compound 1)) is a Hypoxia Inducible Factor Prolyl Hydroxylase inhibitor (HIF-PH inhibitor).

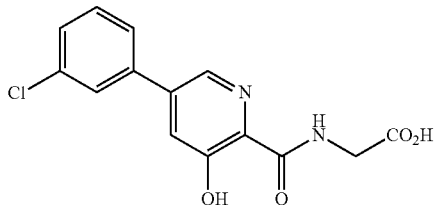 [SMILES: O=C(O)CNC(=O)c1ncc(-c2cccc(Cl)c2)cc1O]

Compound 1

Compound 1 has emerged as a new drug that is highly useful for treating or preventing anemia secondary to or associated with chronic kidney disease (renal anemia). Accordingly, there exists a need to provide solid forms of Compound 1, which may have desirable pharmaceutical properties, especially for formulation into solid (e.g. oral) pharmaceutical dosage forms.

Disclosed herein are solid forms of Compound 1 and methods of making the same. The solid forms of Compound 1 disclosed herein are useful in the treatment and/or prevention of anemia (e.g., anemia secondary to or associated with chronic kidney disease). Accordingly, also provided herein are methods for the treating anemia (e.g., anemia secondary to or associated with chronic kidney disease), comprising administering to a subject having anemia an effective amount of the solid form of Compound 1.

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

Solid Form(s): The term "solid form(s)," refers to a physical form comprising Compound 1 which is not predominantly in a liquid or a gaseous state. Crystal forms and amorphous forms are examples of solid forms. In embodiments, the solid form is Form D. In embodiments, the solid form is Form E. In embodiments, the solid form is Form F. In embodiments, the solid form is Form F. In embodiments, the solid form is Form $H_A$. In embodiments, the solid form is Form $H_B$. In embodiments, the solid form is Form $S_A$. In embodiments, the solid form is Form $S_B$. In embodiments, the solid form is Form $S_C$. In embodiments, the solid form is Form $S_E$. In embodiments, the solid form is Form $S_F$.

Crystalline: The term "crystalline," when used to describe a substance, component, product, or form, means that the substance, component or product is substantially crystalline as determined by X-ray powder diffraction. See, e.g., Remington's Pharmaceutical Sciences, 22nd ed., Pharmaceutical Press, (2012); *The United States Pharmacopoeia*, 30*th* ed., (2011).

Crystal Form or Crystalline Form: The terms "crystal form" and "crystalline form" refer to a crystalline solid form comprising a chemical compound, and may refer to a particular single-component or multiple-component crystal form, including, but not limited to, a polymorph, a solvate, a hydrate or other molecular complex, a salt, a solvate of a salt, a hydrate of a salt, or other molecular complex of a salt, or a polymorph thereof.

Polymorph: The terms "polymorphs" and "polymorphic forms" refer to two or more crystal forms that comprise the same molecule, molecules or ions. Different polymorphs may have different physical properties such as, for example, melting temperatures, heats of fusion, solubilities, dissolution rates and/or vibrational spectra as a result of the arrangement or conformation of the molecules or ions in the crystal lattice. The differences in physical properties exhibited by polymorphs affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

Techniques for characterizing crystal forms and amorphous forms include, but are not limited to, thermal gravimetric analysis (TGA), melting point, differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy (e.g., polarized light microscopy), hot stage optical microscopy, scanning electron microscopy (SEM), electron crystallography, dynamic vapor sorption (DVS), and quantitative analysis, particle size analysis (PSA), surface area analysis, solubility studies and dissolution studies.

Amorphous: The term "amorphous" and "amorphous form" mean that the substance, component or product in question is not substantially crystalline as determined by X-ray diffraction. In certain embodiments, a sample comprising an amorphous form of a substance may be substantially free of other amorphous forms and/or crystal forms.

Animal: As used herein, the term "animal" refers to any member of the animal kingdom. In some embodiments, "animal" refers to humans, at any stage of development. In some embodiments, "animal" refers to non-human animals, at any stage of development. In embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dose(s): As used herein, the term "dose(s)" means a quantity of the compound or a pharmaceutically acceptable salt, solvate, or hydrate thereof to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet).

Daily dose: As used herein, the term "daily dose" means a quantity of the compound, or a pharmaceutically acceptable salt, solvate, or hydrate thereof that is administered in a 24-hour period. Accordingly, a daily dose may be administered all at once (i.e., once daily dosing) or alternatively the daily dosing may be divided such that administration of the compound is twice daily, three times daily, or even four times daily.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{-alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate, and aryl sulfonate. Further pharmaceutically acceptable salts include salts formed from the quarternization of an amine using an appropriate electrophile, e.g., an alkyl halide, to form a quarternized alkylated amino salt.

Preventing: The term "prevent," "preventing," or "prevention," as used herein refers to an effect that mitigates an undesired effect, e.g., an undesirable drug-drug interaction or the formation of a drug-iron chelate. Prevention does not require the 100% elimination of the possibility of an event. Rather, it denotes that the likelihood of the occurrence of the event has been reduced by the compound or method.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one-unit dose.

Treating: As used herein, the term "treat," "treatment," or "treating" refers to any method used to partially or completely alleviate, ameliorate, relieve, inhibit, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD". In this regard, there are three different PHD isoforms, PHD1, PHD2, and PHD3, also referred to as EGLN2, EGLN1, and EGLN3, or HPH3, HPH2, and HPH1, respectively.

As used herein, the term "unit dosage form(s)" includes tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose nor does a single unit dosage form necessarily constitute an entire dose.

Further abbreviations and acronyms are provided below.
ACTH adrenocorticotropic hormone
AE adverse event
ALT alanine aminotransferase (SGPT)
ANOVA analysis of variance
AST aspartate aminotransferase (SGOT)
BUN blood urea nitrogen
C Celsius
CBC complete blood count
CHF congestive heart failure
CKD chronic kidney disease
CKD-EPI Chronic Kidney Disease Epidemiology Collaboration
CMH Cochran-Mantel-Haenszel
CPK creatine phosphokinase
CRF case report form
CRO contract research organization
CS clinically significant
CV cardiovascular
CVD cardiovascular disease
dL deciliter
DVT deep venous thrombosis
EAC Endpoint Adjudication Committee
ECG electrocardiogram
EDC electronic data capture
eGFR estimated glomerular filtration rate
EOT end of treatment
EPO erythropoietin
ESA erythropoiesis-stimulating agent
ESRD end-stage renal disease
EU European Union
F Fahrenheit
FDA Food and Drug Administration g gram
GCP Good Clinical Practice
GFR glomerular filtration rate
GMP Good Manufacturing Practice
HA health authority
HDL high-density lipoprotein
Hgb hemoglobin
HIF hypoxia-inducible factor
HIFPH hypoxia-inducible factor prolyl-hydroxylase
HIF-PHI hypoxia-inducible factor prolyl-hydroxylase inhibitor
$IC_{50}$ 50% inhibitory concentration
ICH International Conference on Harmonization
IDMC Independent Data Monitoring Committee
IDMS isotope dilution mass spectrometry
IEC independent ethics committee
INR international normalized ratio
IRB institutional review board
IV intravenous(ly)
IWR interactive web response
JSDT Japanese Society for Dialysis Therapy
JSN Japanese Society of Nephrology
KDIGO Kidney Disease: Improving Global Outcomes
kg kilogram
LDH lactate dehydrogenase
LDL low-density lipoprotein
LLN lower limit of normal
MACE major adverse cardiovascular events
MCH mean corpuscular (cell) hemoglobin
MCHC mean corpuscular (cell) hemoglobin concentration
MCV mean corpuscular (cell) volume
MedDRA Medical Dictionary for Regulatory Activities
µM micromolar
mg milligram
mL milliliter
mRNA messenger ribonucleic acid
MTD maximum tolerated dose
NDD-CKD non-dialysis dependent chronic kidney disease
ng nanogram
PD pharmacodynamics(s)
PE pulmonary embolism
PHD prolyl 4-hydroxylase domain
PK pharmacokinetic(s)
PP per protocol
PT prothrombin time
PTT partial thromboplastin time
QA quality assurance
QC quality control
RBC red blood cell
RDW red cell distribution width
ROW rest of world
SAE serious adverse event
SAP Statistical Analysis Plan
$S_C$ subcutaneous(ly)
SGOT serum glutamic oxaloacetic transaminase (AST)
SGPT serum glutamic pyruvic transaminase (ALT)
SmPC summary of product characteristics
SV Screening visit
TIBC total iron binding capacity
TREAT Trial to Reduce Cardiovascular Events with Aranesp Therapy
TSAT transferrin saturation
uACR urine albumin-to-creatinine ratio
ULN upper limit of normal
US United States
VEGF vascular endothelial growth factor
WBC white blood cell
WHO World Health Organization Solid Forms Certain embodiments herein provide single-component and multiple-component (e.g., salts, solvates, hydrates) solid forms comprising Compound 1, having the chemical structure:

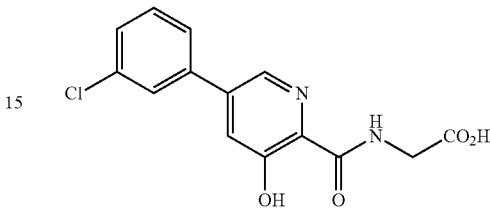

Compound 1

In embodiments, the solid form is Form D. In embodiments, the solid form is Form E. In embodiments, the solid form is Form F. In embodiments, the solid form is Form $H_A$. In embodiments, the solid form is Form $H_B$. In embodiments, the solid form is Form $S_A$. In embodiments, the solid form is Form $S_B$. In embodiments, the solid form is Form $S_C$. In embodiments, the solid form is Form $S_E$.

In embodiments, the solid form is Form $S_F$. In some embodiments the solid Form of Compound 1 (e.g., Form D, Form E, Form F, Form $H_A$, Form $H_B$, Form $S_A$, Form $S_B$, Form $S_C$, Form $S_E$, Form $S_F$) is crystalline. In some such embodiments, the disclosed solid forms (e.g., Form D, Form E, Form F, Form $H_A$, Form $H_B$, Form $S_A$, Form $S_B$, Form $S_C$, Form $S_E$, Form $S_F$) of Compound 1 exhibits high crystallinity and/or favorable solubility characteristics.

In certain embodiments, Forms D, E, F, $H_A$, $H_B$, $S_A$, $S_B$, $S_C$, $S_D$, $S_E$, and/or $S_F$ of Compound 1 have an advantageous stability profile, which is an important characteristic for processing and manufacturing.

In certain embodiments, Forms D, E, F, $H_A$, $H_B$, $S_A$, $S_B$, $S_C$, $S_D$, $S_E$, and/or $S_F$ of Compound 1 are highly pure forms of Compound 1, which are substantially free of impurities (such as other solid forms of Compound 1 and by-products from the manufacturing process). In some embodiments, purity may be determined, e.g., by HPLC.

In embodiments, each of solid Form D, E, F, $H_A$, $H_B$, $S_A$, $S_B$, $S_C$, $S_D$, $S_E$, and $S_F$ of Compound 1 is characterized by a distinctive X-ray powder diffraction pattern (XRPD).

Other solid forms of Compound 1 have been disclosed in International Publication No. WO 2015/073779, which is incorporated by reference herein. Such solid forms include Form A, Form B, and Form C.

Polymorphism

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance can possess different energies of the crystal lattice and, thus, in solid state they can show different physical properties such as form, density, melting point, color, stability, solubility, dissolution rate, etc., which can, in turn, affect the stability, dissolution rate, and/or bioavailability of a given polymorph and its suitability for use as a pharmaceutical and in pharmaceutical compositions. Different polymorphs of a compound (e.g., Compound (I)) can incorporate different impurities, or chemical residues, upon crystallization. Certain polymorphs incorporate very little, or no, chemical residues. Accordingly, the formation of certain polymorph forms of a compound may result in purification of the compound.

Characterization of Solid Forms and Polymorphs of Compound 1

In certain embodiments, the solid forms of Compound 1 are identifiable on the basis of peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials.

In some embodiments, the solid forms of Compound 1 may also be defined by their differential scanning calorimetry (DSC) thermograms. The DSC thermogram is used observe crystallization events, and, in particular, measure the crystallization temperature (Tc) of a sample via a characteristic endotherm.

In some embodiments, the solid forms of Compound 1 may also be defined by thermal gravimetric analysis (TGA), which is a method of thermal analysis in which the mass of a sample is measured over time. This measurement provides information about physical phenomena, such as phase transitions, absorption, adsorption and desorption; as well as chemical phenomena including chemisorptions, thermal decomposition, and solid-gas reactions (e.g., oxidation or reduction).

Form D

In embodiments, the solid Form D of Compound 1 is characterized by an X-ray powder diffraction pattern substantially in accordance with FIG. 1.

In embodiments, the solid Form D of Compound 1 is characterized by an X-ray powder diffraction pattern comprising peaks at 7.9, 14.4, 14.8, 15.9, and 23.9±0.2° 2θ.

In embodiments, the solid Form D of Compound 1 is characterized by an X-ray powder diffraction pattern comprising peaks at 2.2, 6.6, 7.9, 14.8, and 26.0±0.2° 2θ.

In embodiments, the solid Form D of Compound 1 is characterized by an X-ray powder diffraction pattern comprising peaks at 6.6, 7.9, 13.4, 15.9, 20.1, and 24.5±0.2° 2θ.

In embodiments, the solid Form D of Compound 1 is characterized by an X-ray powder diffraction pattern which comprises at least one peak selected from the group consisting of 2.2, 6.6, 7.9, 13.4, 14.4, 14.8, 15.9, 20.1, 23.9, 24.5, and 26.0±0.2° 2θ.

In embodiments, the solid Form D of Compound 1 is characterized by an X-ray powder diffraction pattern which comprises one, two, three, four, five, and/or six peaks selected from the group consisting of 2.2, 6.6, 7.9, 13.4, 14.4, 14.8, 15.9, 20.1, 23.9, 24.5, and 26.0±0.2° 2θ.

In embodiments, the solid Form D of Compound 1 is characterized by an X-ray powder diffraction pattern comprising one or more peaks expressed in degrees 2θ (±0.2) as listed in Table 1.

TABLE 1

| XRPD Data of Solid Form D of Compound 1 (prepared by MeOH Slow Cooling) ||
| --- | --- |
| Angle 2θ (±0.2) | Relative Intensity (%) |
| 2.195 | 27.9 |
| 6.633 | 33.2 |
| 7.883 | 61 |
| 9.829 | 7.9 |
| 12.351 | 20.6 |
| 13.361 | 18.8 |
| 14.407 | 53.7 |
| 14.782 | 42.8 |
| 15.053 | 4.4 |
| 15.884 | 100 |
| 18.158 | 7.3 |
| 18.666 | 7.5 |
| 19.656 | 22.8 |
| 20.069 | 16.3 |
| 20.956 | 7.1 |
| 22.118 | 27.2 |
| 22.654 | 7.4 |
| 22.986 | 6.5 |
| 23.95 | 44.7 |
| 24.508 | 16.4 |
| 24.743 | 12.2 |
| 25.508 | 27.2 |
| 26.003 | 37.8 |
| 26.301 | 28.1 |
| 26.867 | 5.3 |
| 27.067 | 4.6 |
| 27.427 | 14.1 |
| 27.582 | 27.1 |
| 28.311 | 12.7 |
| 28.885 | 8.3 |
| 29.196 | 7.9 |
| 30.823 | 8.2 |
| 31.091 | 5.1 |
| 32.001 | 9.2 |
| 33.34 | 3.8 |
| 34.703 | 4.2 |
| 35.214 | 6.7 |
| 35.468 | 16.4 |
| 36.554 | 5.8 |
| 37.169 | 4.7 |
| 37.506 | 3.7 |
| 38.644 | 3.7 |

In embodiments, the solid Form D of Compound 1 is characterized by an X-ray powder diffraction pattern comprising, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, and/or forty-two peaks expressed in degrees 2θ (±0.2) as listed in Table 1.

In embodiments, the solid Form D of Compound 1 is characterized by an X-ray powder diffraction pattern comprising five peaks expressed in degrees 2θ (±0.2) as listed in Table 1.

In embodiments, the solid Form D of Compound 1 is characterized by an X-ray powder diffraction pattern comprising ten peaks expressed in degrees 2θ (±0.2) as listed in Table 1.

In embodiments, the solid Form D of Compound 1 is characterized by an X-ray powder diffraction pattern comprising fifteen peaks expressed in degrees 2θ (±0.2) as listed in Table 1.

In embodiments, the solid Form D of Compound 1 is characterized by an X-ray powder diffraction pattern comprising twenty peaks expressed in degrees 2θ (±0.2) as listed in Table 1.

In embodiments, the solid Form D of Compound 1 is characterized by an X-ray powder diffraction pattern comprising twenty-five peaks expressed in degrees 2θ (±0.2) as listed in Table 1.

In embodiments, the solid Form D of Compound 1 is characterized by an X-ray powder diffraction pattern comprising thirty peaks expressed in degrees 2θ (±0.2) as listed in Table 1.

In embodiments, the solid Form D of Compound 1 is characterized by an X-ray powder diffraction pattern comprising thirty-five peaks expressed in degrees 2θ (±0.2) as listed in Table 1.

In embodiments, the solid Form D of Compound 1 is characterized by an X-ray powder diffraction pattern comprising forty peaks expressed in degrees 2θ (±0.2) as listed in Table 1.

In embodiments, the solid Form D of Compound 1 is characterized by an X-ray powder diffraction pattern comprising forty-two peaks expressed in degrees 2θ (±0.2) as listed in Table 1.

Figure 2:
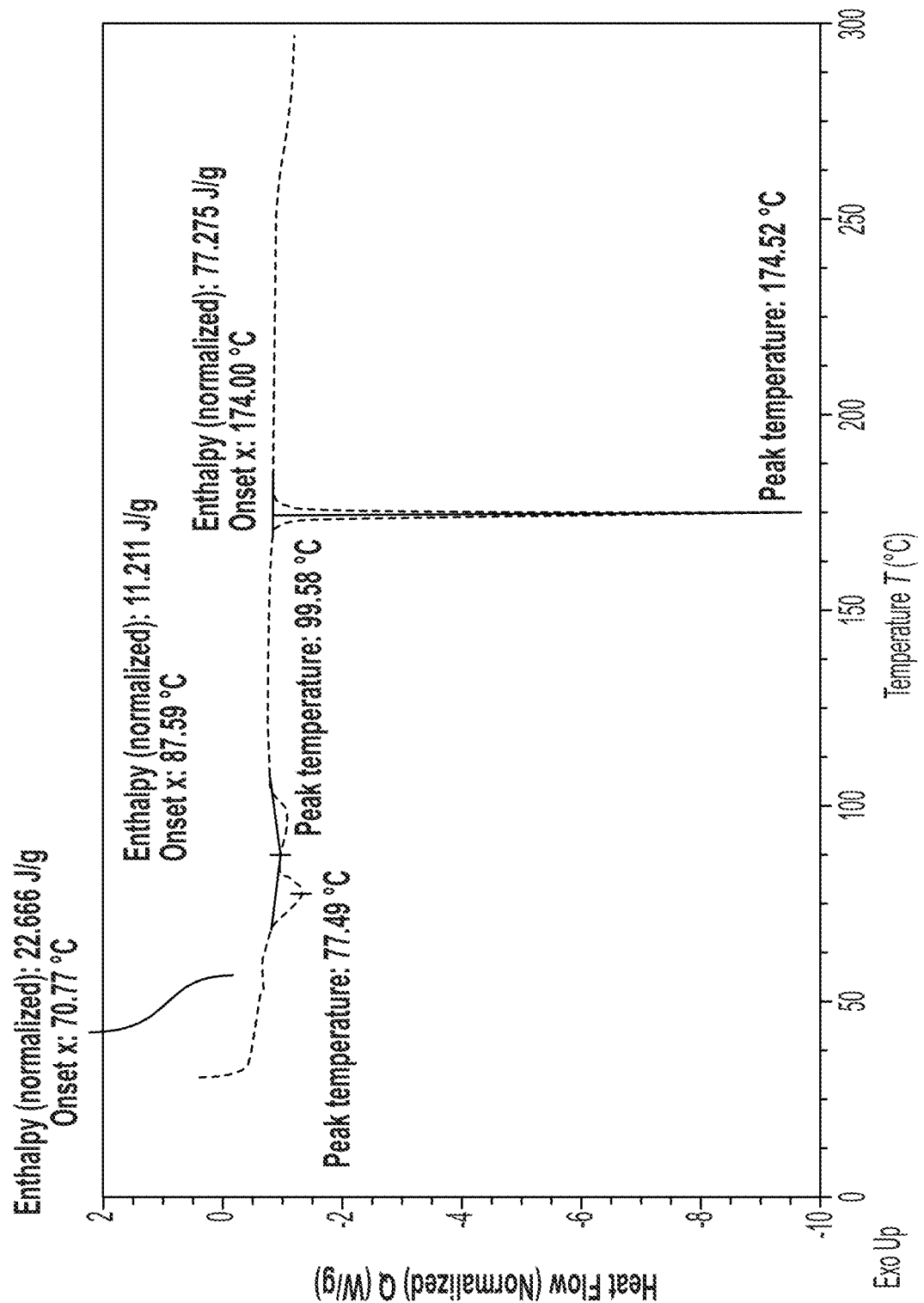
FIG. 2 shows a differential scanning calorimetry (DSC) thermogram of Compound 1, Form D prepared by slow cooling method.

In embodiments, the solid Form D of Compound 1 is characterized by a differential scanning calorimetry thermogram having a characteristic endotherm peak at 174.52° C. (FIG. 2).

Figure 3:
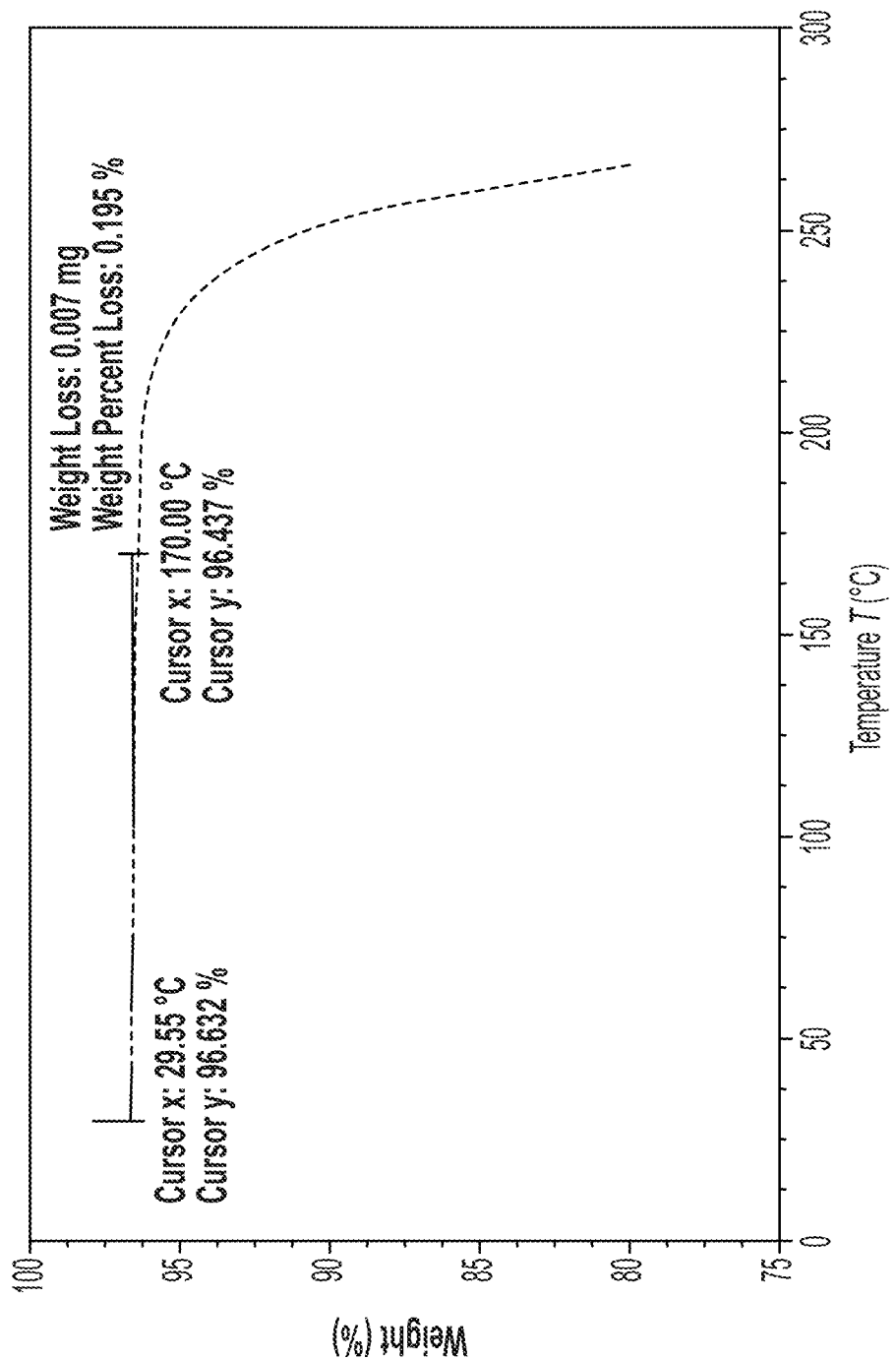
FIG. 3 shows a thermal gravimetric analysis (TGA) thermogram of Compound 1, Form D.

In embodiments, a representative TGA thermogram of the solid Form D of Compound 1 is shown in FIG. 3. In some embodiments, the solid Form D of Compound 1 exhibits 0.2% weight loss up to 170° C.

In embodiments, the solid Form D of Compound 1 is substantially pure of impurities (e.g., other chemical compounds (i.e., not Compound 1)). In certain embodiments the solid Form D of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form D of Compound 1 is substantially free of any other solid form of Compound 1. For example, in embodiments, the solid Form D of Compound 1 is substantially free of Form A, Form B, Form C, Form E, Form F, Form $H_A$, Form $H_B$, Form $S_A$, Form $S_B$, Form $S_C$, Form $S_D$, Form $S_E$, and Form $S_F$. In certain embodiments, the solid Form D of Compound 1 comprises less than 15%, less than 10%, or less than 5% by weight of each of Form A, Form B, Form C, Form E, Form F, Form $H_A$, Form $H_B$, Form $S_A$, Form $S_B$, Form $S_C$, Form $S_D$, Form $S_E$, and Form $S_F$.

Form E

In certain embodiments, the invention provides a solid Form E of Compound 1. In embodiments, the solid Form E of Compound 1 is unsolvated. In embodiments, the solid Form E of Compound 1 is anhydrous. In embodiments, the solid Form E of Compound 1 is unsolvated and anhydrous.

Figure 4:
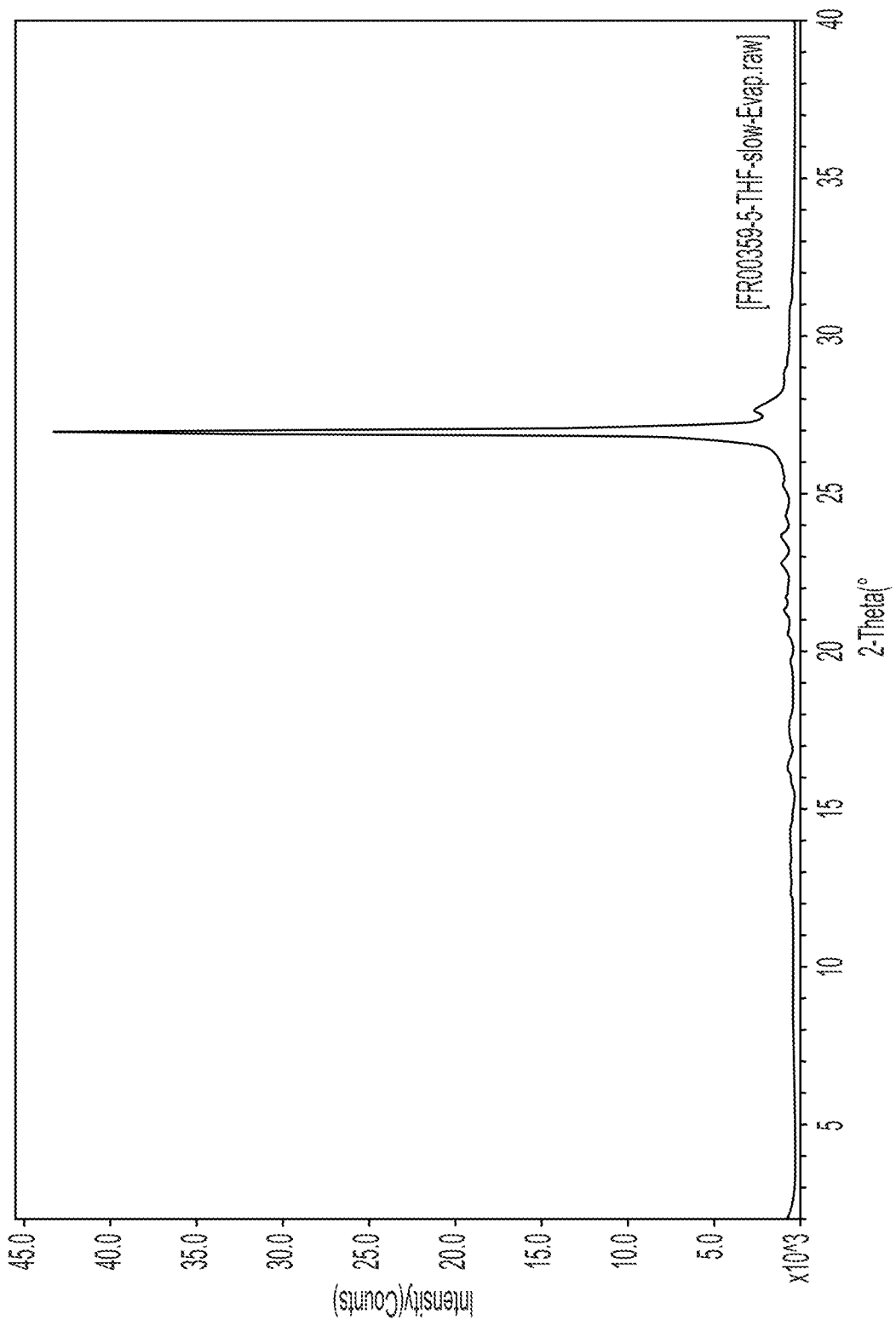
FIG. 4 shows an X-ray powder diffraction (XRPD) analysis of Compound 1, Form E.

In embodiments, the solid Form E of Compound 1 is characterized by an X-ray powder diffraction pattern substantially in accordance with FIG. 4.

In embodiments, the solid Form E of Compound 1 is characterized by an X-ray powder diffraction pattern comprising peaks at 21.3, 22.8, 23.7, 27.0, and 27.7±0.2° 2θ.

In embodiments, the solid Form E of Compound 1 is characterized by an X-ray powder diffraction pattern comprising peaks at 16.4, 22.8, 23.7, 27.0, and 27.7±0.2° 2θ.

In embodiments, the solid Form E of Compound 1 is characterized by an X-ray powder diffraction pattern which comprises at least one peak selected from the group consisting of 16.4, 21.3, 22.8, 23.7, 27.0, and 27.7±0.2° 2θ.

In embodiments, the solid Form E of Compound 1 is characterized by an X-ray powder diffraction pattern which comprises one, two, three, four, and/or five peaks selected from the group consisting of 16.4, 21.3, 22.8, 23.7, 27.0, and 27.7±0.2° 2θ.

In embodiments, the solid Form E of Compound 1 is characterized by an X-ray powder diffraction pattern comprising one or more peaks expressed in degrees 2θ (±0.2) as listed in Table 2.

TABLE 2

XRPD Data of Solid Form E of Compound 1

| Angle 2θ (±0.2) | Relative Intensity (%) |
|---|---|
| 13.335 | 0.3 |
| 14.127 | 0.3 |
| 14.347 | 0.5 |
| 14.621 | 0.3 |
| 15.847 | 0.4 |
| 16.104 | 0.4 |
| 16.417 | 0.7 |
| 16.594 | 0.4 |
| 17.208 | 0.4 |
| 17.522 | 0.5 |
| 17.816 | 0.5 |
| 17.914 | 0.4 |
| 19.523 | 0.3 |
| 20.543 | 0.3 |
| 21.309 | 0.9 |
| 21.705 | 0.7 |
| 22.059 | 0.3 |
| 22.827 | 1 |
| 23.461 | 0.5 |
| 23.677 | 1 |
| 24.348 | 0.5 |
| 25.309 | 0.5 |
| 26.97 | 100 |
| 27.661 | 4 |

In embodiments, the solid Form E of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, and/or twenty-four peaks expressed in degrees 2θ (±0.2) as listed in Table 2.

In embodiments, the solid Form E of Compound 1 is characterized by an X-ray powder diffraction pattern comprising five peaks expressed in degrees 2θ (±0.2) as listed in Table 2.

In embodiments, the solid Form E of Compound 1 is characterized by an X-ray powder diffraction pattern comprising ten peaks expressed in degrees 2θ (±0.2) as listed in Table 2.

In embodiments, the solid Form E of Compound 1 is characterized by an X-ray powder diffraction pattern comprising fifteen peaks expressed in degrees 2θ (±0.2) as listed in Table 2.

In embodiments, the solid Form E of Compound 1 is characterized by an X-ray powder diffraction pattern comprising twenty peaks expressed in degrees 2θ (±0.2) as listed in Table 2.

In embodiments, the solid Form E of Compound 1 is characterized by an X-ray powder diffraction pattern comprising twenty-four peaks expressed in degrees 2θ (±0.2) as listed in Table 2.

Figure 5:
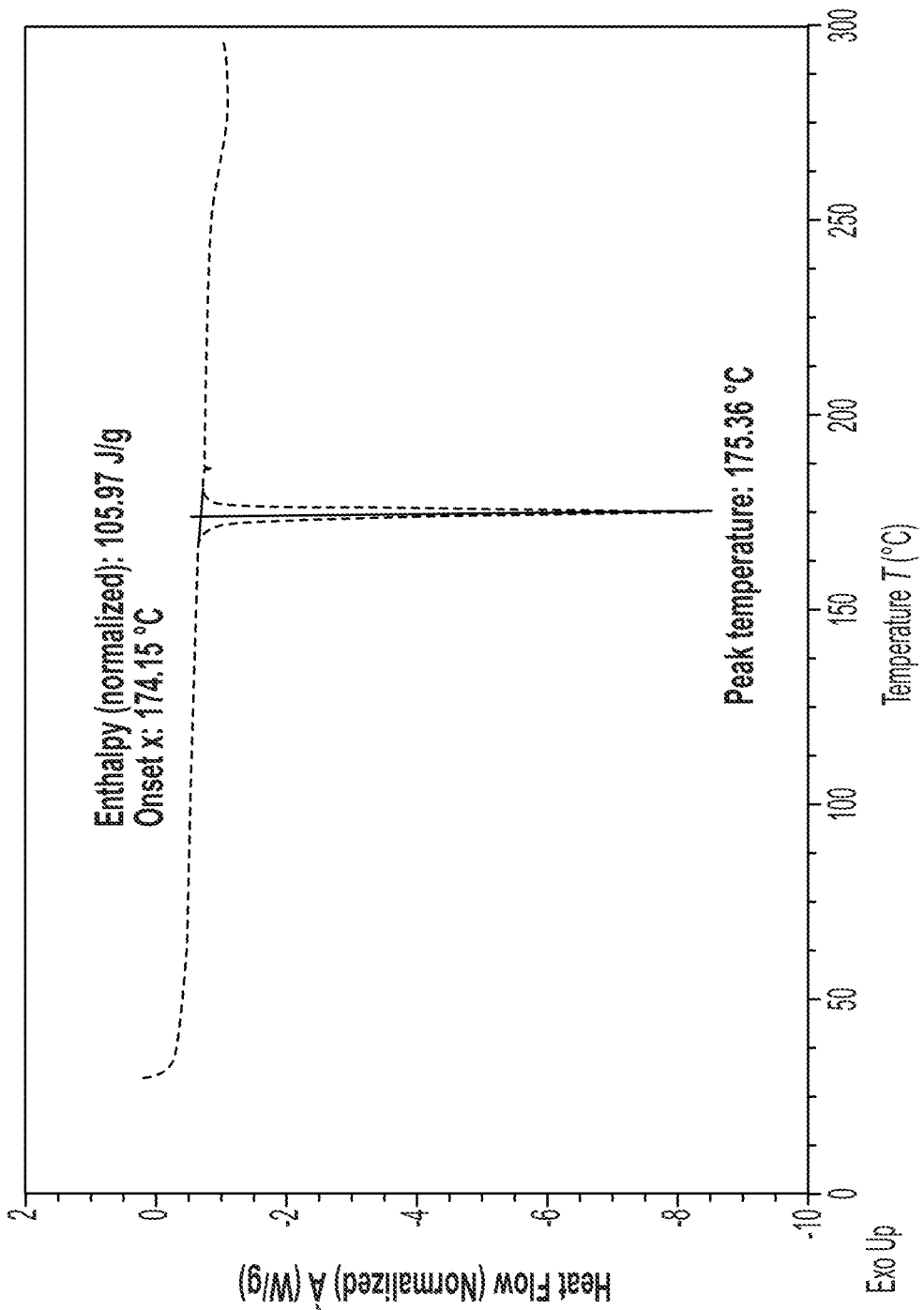
FIG. 5 shows a differential scanning calorimetry (DSC) thermogram of Compound 1, Form E.

In embodiments, the solid Form E of Compound 1 is characterized by a differential scanning calorimetry thermogram having a characteristic endotherm peak at 175.4° C. (FIG. 5).

In embodiments, the solid Form E of Compound 1 is characterized by a differential scanning calorimetry thermogram having a characteristic endotherm onset temperature at 174.2° C. (FIG. 5).

Figure 6:
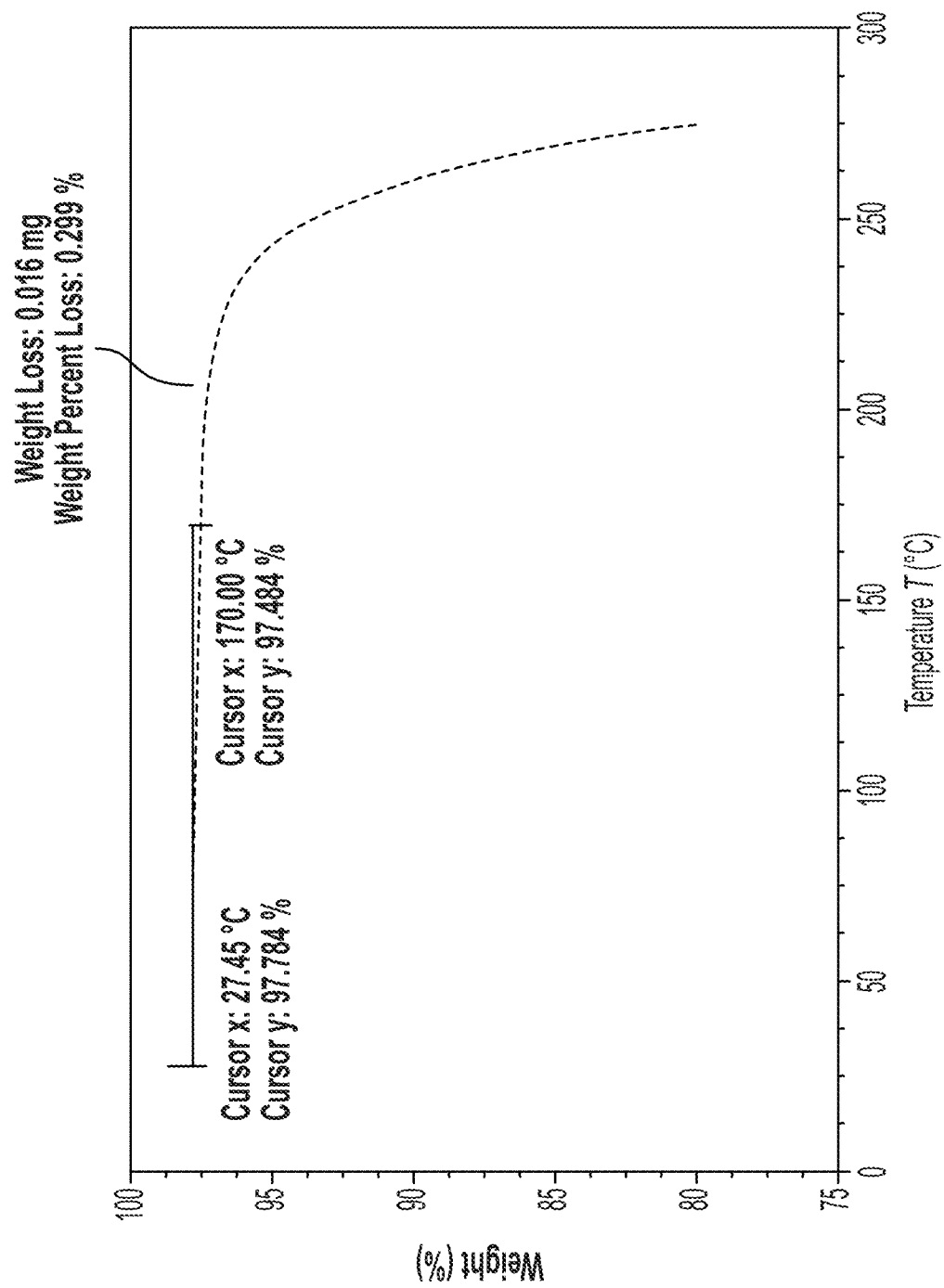
FIG. 6 shows a thermal gravimetric analysis (TGA) thermogram of Compound 1, Form E.

In embodiments, a representative TGA thermogram of the solid Form E of Compound 1 is shown in FIG. 6. In some embodiments, the solid Form E of Compound 1 exhibits 0.3% weight loss up to 170° C.

In embodiments, the solid Form E of Compound 1 is substantially pure of impurities (e.g., other chemical compounds (i.e., not Compound 1)). In certain embodiments the solid Form E of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form E of Compound 1 is substantially free of any other solid form of Compound 1. For example, in embodiments, the solid Form E of Compound 1 is substantially free of Form A, Form B, Form C, Form D, Form F, Form $H_A$, Form $H_B$, Form $S_A$, Form $S_B$, Form $S_C$, Form $S_D$, Form $S_E$, and Form $S_F$. In certain embodiments, the solid Form E of Compound 1 comprises less than 15%, less than 10%, or less than 5% by weight of each of Form A, Form B, Form C, Form D, Form F, Form $H_A$, Form $H_B$, Form $S_A$, Form $S_B$, Form $S_C$, Form $S_D$, Form $S_E$, and Form $S_F$.

Form F

In embodiments, the invention provides a solid Form F of Compound 1. In embodiments, the solid Form F of Compound 1 is unsolvated. In embodiments, the solid Form F of Compound 1 is anhydrous. In embodiments, the solid Form F of Compound 1 is unsolvated and anhydrous.

In embodiments, the solid Form F of Compound 1 is characterized by high crystallinity.

Figure 7:
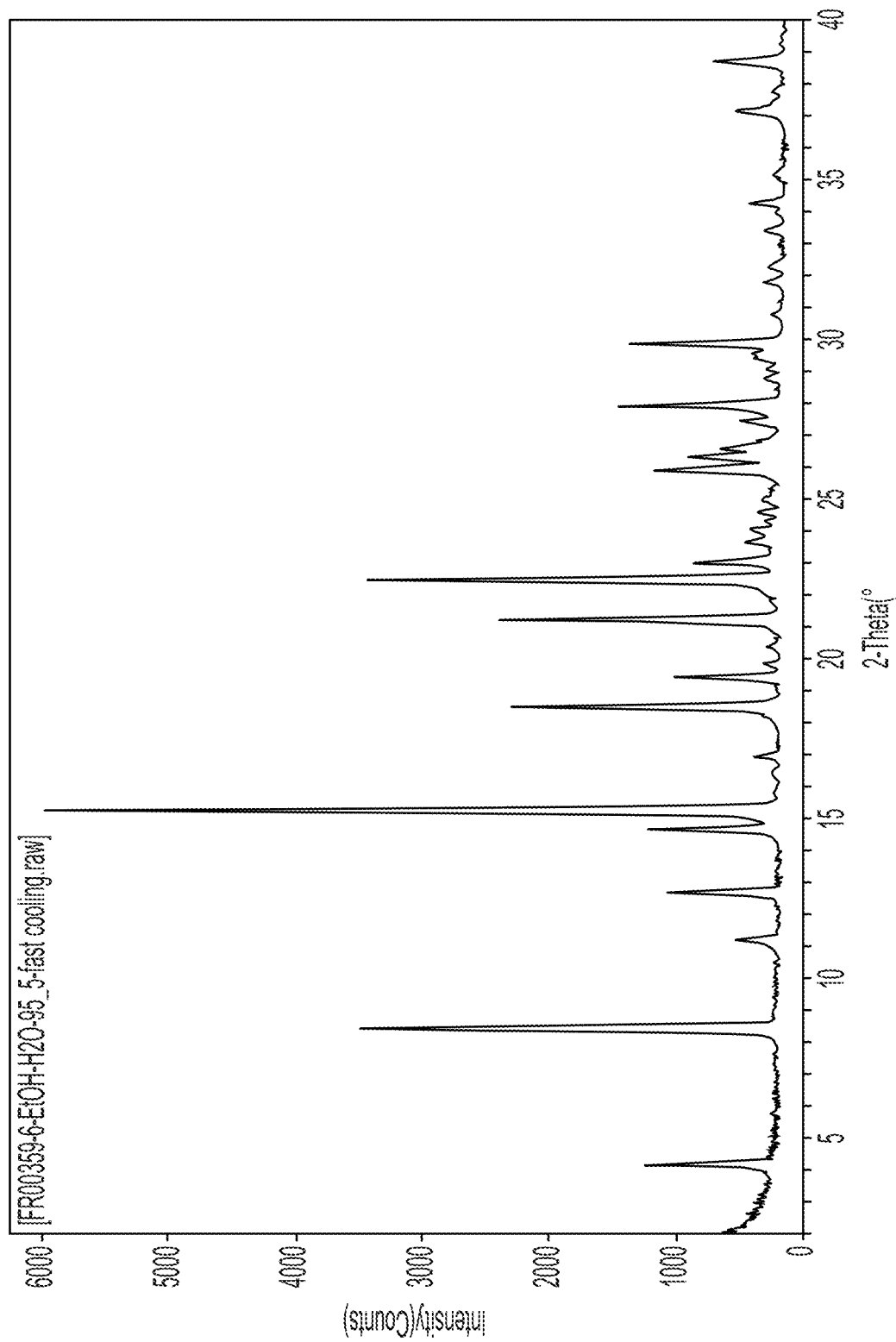
FIG. 7 shows an X-ray powder diffraction (XRPD) analysis of Compound 1, Form F.

In embodiments, the solid Form F of Compound 1 is characterized by an X-ray powder diffraction pattern substantially in accordance with FIG. 7.

In embodiments, the solid Form F of Compound 1 is characterized by an X-ray powder diffraction pattern comprising peaks at 8.5, 15.3, 18.5, 21.3, and 22.5±0.2° 2θ.

In embodiments, the solid Form F of Compound 1 is characterized by an X-ray powder diffraction pattern comprising peaks at 4.2, 12.7, 19.5, 25.9, and 29.9±0.2° 2θ.

In embodiments, the solid Form F of Compound 1 is characterized by an X-ray powder diffraction pattern comprising peaks at 4.2, 8.5, 15.3, 18.5, 21.3, and 22.5±0.2° 2θ.

In embodiments, the solid Form F of Compound 1 is characterized by an X-ray powder diffraction pattern which comprises at least one peak selected from the group consisting of 4.2, 8.5, 12.7, 15.3, 18.5, 19.5, 21.3, 22.5, 25.9, and 29.9±0.2° 2θ.

In embodiments, the solid Form F of Compound 1 is characterized by an X-ray powder diffraction pattern which comprises one, two, three, four, five, and/or six peaks selected from the group consisting of 4.2, 8.5, 12.7, 15.3, 18.5, 19.5, 21.3, 22.5, 25.9, and 29.9±0.2° 2θ.

In embodiments, the solid Form F of Compound 1 is characterized by an X-ray powder diffraction pattern comprising one or more peaks expressed in degrees 2θ (±0.2) as listed in Table 3.

TABLE 3

XRPD Data of Solid Form F of Compound 1

| Angle 2θ (±0.2) | Relative Intensity (%) |
| --- | --- |
| 4.229 | 17.3 |
| 8.47 | 57.2 |
| 11.214 | 5.8 |
| 12.73 | 15.1 |
| 14.7 | 17.4 |
| 15.294 | 100 |
| 16.497 | 0.8 |
| 16.956 | 3.3 |
| 18.507 | 36.8 |
| 19.456 | 13.8 |
| 19.864 | 1.8 |
| 20.388 | 1.8 |
| 21.25 | 37.6 |
| 22.493 | 55.1 |
| 23.028 | 10.2 |
| 23.677 | 3.6 |
| 24.068 | 2.8 |
| 24.603 | 1.9 |
| 24.993 | 1.6 |
| 25.904 | 16.3 |
| 26.338 | 11.8 |
| 26.559 | 7.3 |
| 27.443 | 5 |
| 27.955 | 21.6 |
| 29.093 | 1.6 |
| 29.398 | 3.5 |
| 29.87 | 20 |
| 30.816 | 1.5 |
| 31.807 | 2.8 |
| 32.316 | 2.1 |
| 33.419 | 2.4 |
| 33.934 | 1 |
| 34.247 | 4.3 |
| 35.14 | 1.4 |
| 37.168 | 6.1 |
| 37.778 | 1.3 |
| 38.685 | 9.3 |

In embodiments, the solid Form F of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, and/or thirty-seven peaks expressed in degrees 2θ (±0.2) as listed in Table 8.

In embodiments, the solid Form F of Compound 1 is characterized by an X-ray powder diffraction pattern comprising five peaks expressed in degrees 2θ (±0.2) as listed in Table 3.

In embodiments, the solid Form F of Compound 1 is characterized by an X-ray powder diffraction pattern comprising ten peaks expressed in degrees 2θ (±0.2) as listed in Table 3.

In embodiments, the solid Form F of Compound 1 is characterized by an X-ray powder diffraction pattern comprising fifteen peaks expressed in degrees 2θ (±0.2) as listed in Table 3.

In embodiments, the solid Form F of Compound 1 is characterized by an X-ray powder diffraction pattern comprising twenty peaks expressed in degrees 2θ (±0.2) as listed in Table 3.

In embodiments, the solid Form F of Compound 1 is characterized by an X-ray powder diffraction pattern comprising twenty-five peaks expressed in degrees 2θ (±0.2) as listed in Table 3.

In embodiments, the solid Form F of Compound 1 is characterized by an X-ray powder diffraction pattern comprising thirty peaks expressed in degrees 2θ (±0.2) as listed in Table 3.

In embodiments, the solid Form F of Compound 1 is characterized by an X-ray powder diffraction pattern comprising thirty-five peaks expressed in degrees 2θ (±0.2) as listed in Table 3.

In embodiments, the solid Form F of Compound 1 is characterized by an X-ray powder diffraction pattern comprising thirty-seven peaks expressed in degrees 2θ (±0.2) as listed in Table 3.

Figure 8:
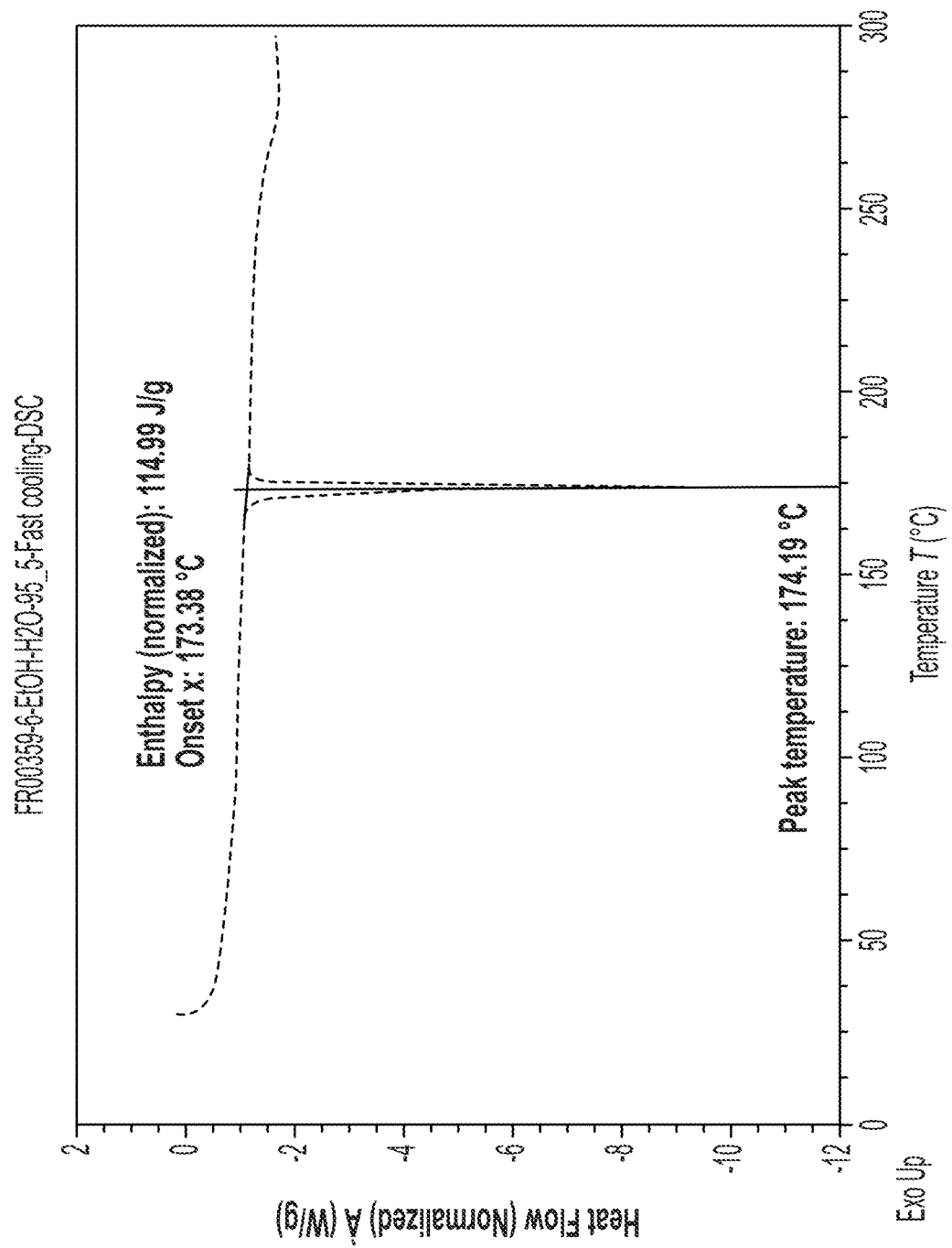
FIG. 8 shows a differential scanning calorimetry (DSC) thermogram of Compound 1, Form F.

In embodiments, the solid Form F of Compound 1 is characterized by a differential scanning calorimetry thermogram having a characteristic endotherm peak at 174.2° C. (FIG. 8).

In embodiments, the solid Form F of Compound 1 is characterized by a differential scanning calorimetry thermogram having a characteristic endotherm onset temperature at 173.4° C. (FIG. 8).

Figure 9:
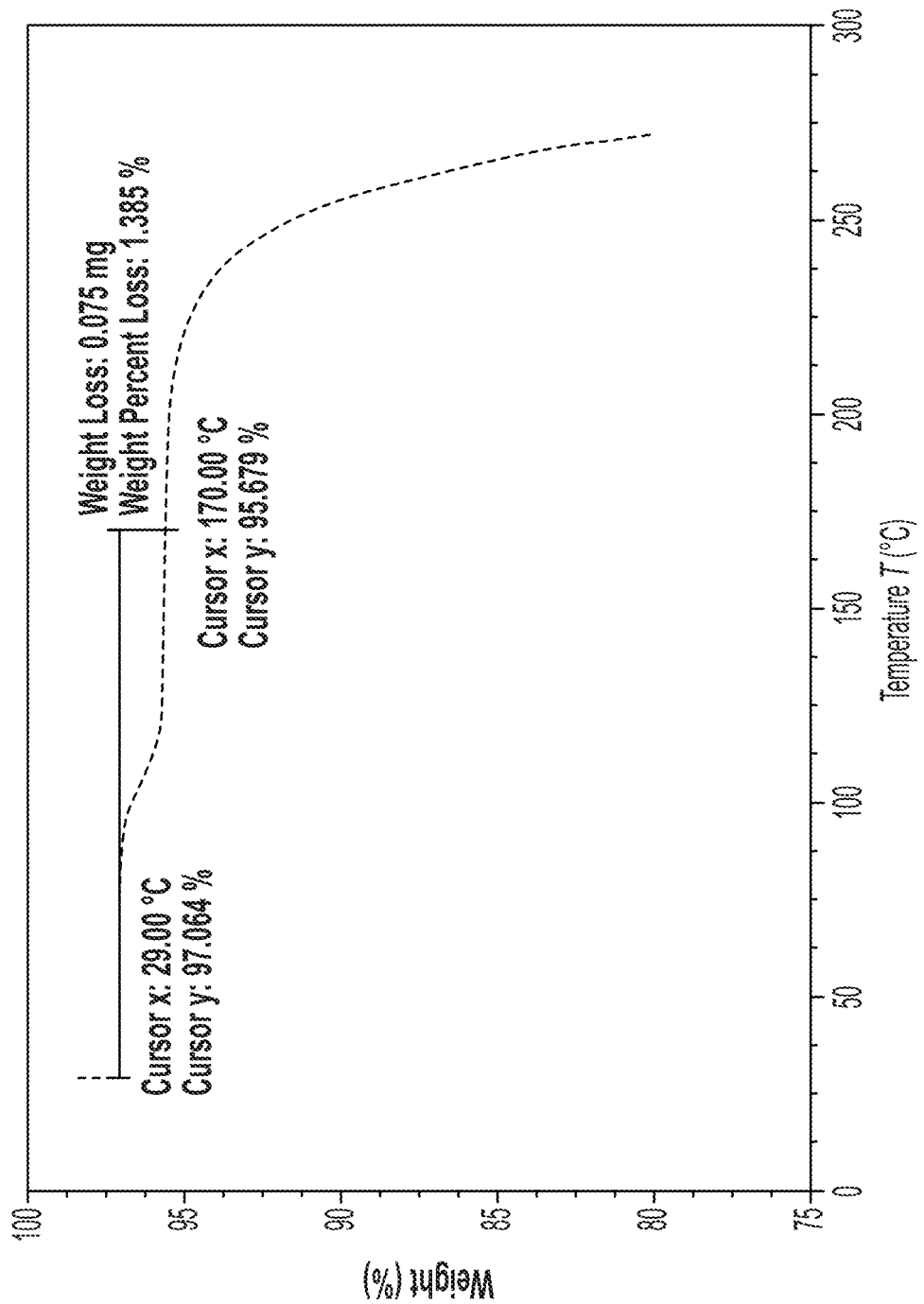
FIG. 9 shows a thermal gravimetric analysis (TGA) thermogram of Compound 1, Form F.

In embodiments, a representative TGA thermogram of the solid Form F of Compound 1 is shown in FIG. 9. In some embodiments, the solid Form F of Compound 1 exhibits 1.4% weight loss up to 170° C.

In embodiments, the solid Form F of Compound 1 is substantially pure of impurities (e.g., other chemical compounds (i.e., not Compound 1)). In certain embodiments the solid Form F of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form F of Compound 1 is substantially free of any other solid form of Compound 1. For example, in embodiments, the solid Form F of Compound 1 is substantially free of Form A, Form B, Form C, Form D, Form E, Form $H_A$, Form $H_B$, Form $S_A$, Form $S_B$, Form $S_C$, Form $S_D$, Form $S_E$, and Form $S_F$. In certain embodiments, the solid Form F of Compound 1 comprises less than 15%, less than 10%, or less than 5% by weight of each of Form A, Form B, Form C, Form D, Form E, Form $H_A$, Form $H_B$, Form $S_A$, Form $S_B$, Form $S_C$, Form $S_D$, Form $S_E$, and Form $S_F$.

Form $H_A$

In certain embodiments, the invention provides a solid Form $H_A$ of Compound 1. In embodiments, the solid Form $H_A$ of Compound 1 is a monohydrate.

In embodiments, the solid Form $H_A$ of Compound 1 is characterized by high crystallinity.

Figure 10:
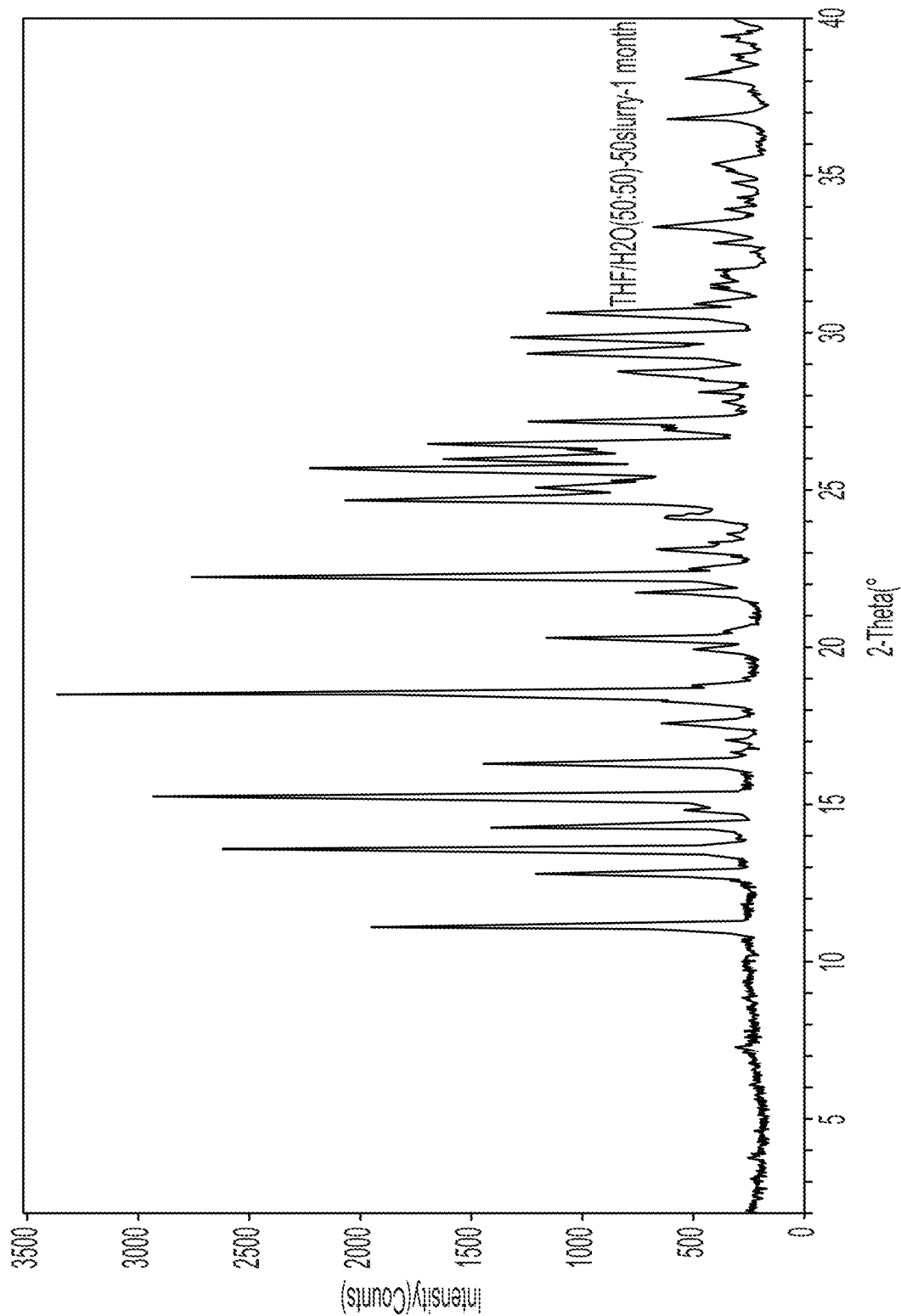
FIG. 10 shows an X-ray powder diffraction (XRPD) analysis of Compound 1, Form $H_A$.

In embodiments, the solid Form $H_A$ of Compound 1 is characterized by an X-ray powder diffraction pattern substantially in accordance with FIG. 10.

In embodiments, the solid Form $H_A$ of Compound 1 is characterized by an X-ray powder diffraction pattern comprising peaks at 13.6, 15.3, 18.5, 22.2, and 24.7±0.2° 2θ.

In embodiments, the solid Form $H_A$ of Compound 1 is characterized by an X-ray powder diffraction pattern comprising peaks at 13.6, 22.2, 25.1, 28.7, and 30.6±0.2° 2θ.

In embodiments, the solid Form $H_A$ of Compound 1 is characterized by an X-ray powder diffraction pattern comprising peaks at 12.8, 14.3, 16.3, 22.2, 24.7, and 25.7±0.2° 2θ.

In embodiments, the solid Form $H_A$ of Compound 1 is characterized by an X-ray powder diffraction pattern which comprises at least one peak selected from the group consisting of 12.8, 13.6, 14.3, 15.3, 16.3, 18.5, 22.2, 24.7, 25.1, 25.7, 28.8, and 30.6±0.2° 2θ.

In embodiments, the solid Form $H_A$ of Compound 1 is characterized by an X-ray powder diffraction pattern which comprises one, two, three, four, five, and/or six peaks selected from the group consisting of 12.8, 13.6, 14.3, 15.3, 16.3, 18.5, 22.2, 24.7, 25.1, 25.7, 28.8, and 30.6±0.2° 2θ.

In embodiments, the solid Form $H_A$ of Compound 1 is characterized by an X-ray powder diffraction pattern comprising one or more peaks expressed in degrees 2θ (±0.2) as listed in Table 4.

TABLE A

XRPD Data of Solid Form $H_A$ of Compound 1

| Angle 2θ (±0.2) | Relative Intensity (%) |
|---|---|
| 7.288 | 2.9 |
| 11.135 | 54.6 |
| 12.794 | 29.9 |
| 13.597 | 75 |
| 14.326 | 36.2 |
| 14.823 | 9.1 |
| 15.255 | 85.9 |
| 16.305 | 38.5 |
| 17.066 | 3.7 |
| 17.597 | 12.5 |
| 18.276 | 13 |
| 18.528 | 100 |
| 18.766 | 8.9 |
| 19.928 | 9.1 |
| 20.283 | 30.5 |
| 20.5 | 5 |
| 21.743 | 17 |
| 22.238 | 80.4 |
| 22.495 | 8.2 |
| 23.123 | 12.6 |
| 23.317 | 5.3 |
| 24.13 | 8.1 |
| 24.683 | 58.3 |
| 25.078 | 19.2 |
| 25.277 | 6.8 |
| 25.651 | 50.4 |
| 25.984 | 34.7 |
| 26.439 | 45.5 |
| 26.951 | 9.4 |
| 27.205 | 29.7 |
| 28.116 | 6 |
| 28.513 | 5.6 |
| 28.728 | 17.1 |
| 29.356 | 31.1 |
| 29.832 | 33.2 |
| 30.563 | 29.3 |
| 30.914 | 7.9 |
| 31.47 | 6.3 |
| 31.746 | 5.1 |
| 31.937 | 6.1 |
| 32.831 | 6.6 |
| 33.321 | 15.3 |
| 33.911 | 3.9 |
| 34.725 | 4.1 |
| 35.038 | 3.7 |
| 35.332 | 7.3 |
| 36.81 | 14 |
| 38.076 | 11 |
| 38.308 | 5.5 |
| 39.378 | 4.9 |

In embodiments, the solid Form $H_A$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thiry-five, thirty-six, thirty-seven, thirty-eight, thirty-nine, forty, forty-one, forty-two, forty-three, forty-four, forty-five, forty-six, forty-seven, forty-eight, forty-nine, and/or fifty peaks expressed in degrees 2θ (±0.2) as listed in Table 4.

In embodiments, the solid Form $H_A$ of Compound 1 is characterized by an X-ray powder diffraction pattern comprising five peaks expressed in degrees 2θ (±0.2) as listed in Table 4.

In embodiments, the solid Form $H_A$ of Compound 1 is characterized by an X-ray powder diffraction pattern comprising ten peaks expressed in degrees 2θ (±0.2) as listed in Table 4.

In embodiments, the solid Form $H_A$ of Compound 1 is characterized by an X-ray powder diffraction pattern comprising fifteen peaks expressed in degrees 2θ (±0.2) as listed in Table 4.

In embodiments, the solid Form $H_A$ of Compound 1 is characterized by an X-ray powder diffraction pattern comprising twenty peaks expressed in degrees 2θ (±0.2) as listed in Table 4.

In embodiments, the solid Form $H_A$ of Compound 1 is characterized by an X-ray powder diffraction pattern comprising twenty-five peaks expressed in degrees 2θ (±0.2) as listed in Table 4.

In embodiments, the solid Form $H_A$ of Compound 1 is characterized by an X-ray powder diffraction pattern comprising thirty peaks expressed in degrees 2θ (±0.2) as listed in Table 4.

In embodiments, the solid Form $H_A$ of Compound 1 is characterized by an X-ray powder diffraction pattern comprising thirty-five peaks expressed in degrees 2θ (±0.2) as listed in Table 4.

In embodiments, the solid Form $H_A$ of Compound 1 is characterized by an X-ray powder diffraction pattern comprising forty peaks expressed in degrees 2θ (±0.2) as listed in Table 4.

In embodiments, the solid Form $H_A$ of Compound 1 is characterized by an X-ray powder diffraction pattern comprising forty-five peaks expressed in degrees 2θ (±0.2) as listed in Table 4.

In embodiments, the solid Form $H_A$ of Compound 1 is characterized by an X-ray powder diffraction pattern comprising fifty peaks expressed in degrees 2θ (±0.2) as listed in Table 4.

Figure 11:
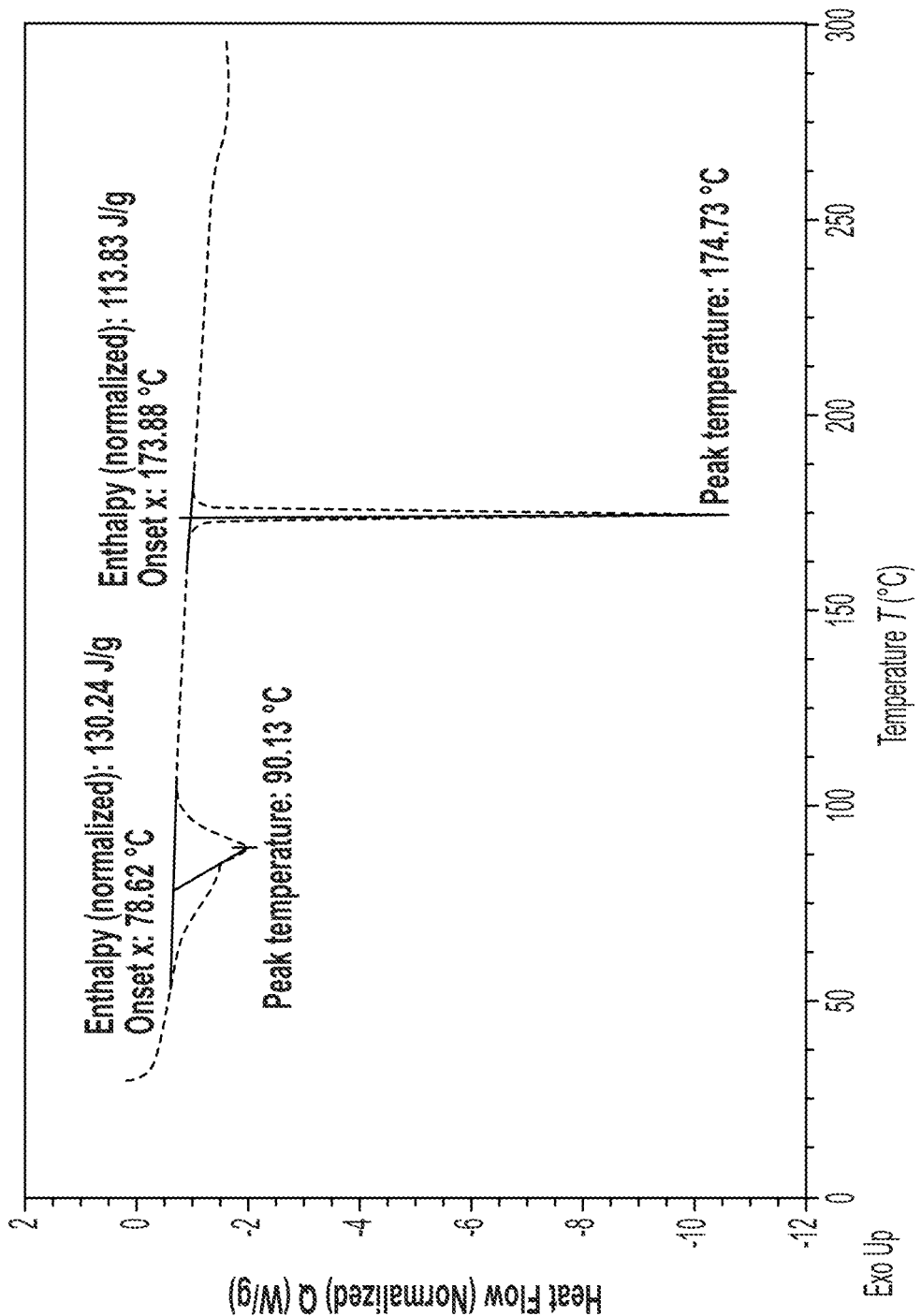
FIG. 11 shows a differential scanning calorimetry (DSC) thermogram of Compound 1, Form $H_A$.

In embodiments, the solid Form $H_A$ of Compound 1 is characterized by a differential scanning calorimetry thermogram having characteristic endotherm peaks at 90.1° C. and 174.7° C. (FIG. 11).

In embodiments, the solid Form $H_A$ of Compound 1 is characterized by a differential scanning calorimetry thermogram having characteristic endotherm onset temperatures at 78.6° C. and 173.9° C. (FIG. 11).

Figure 12:
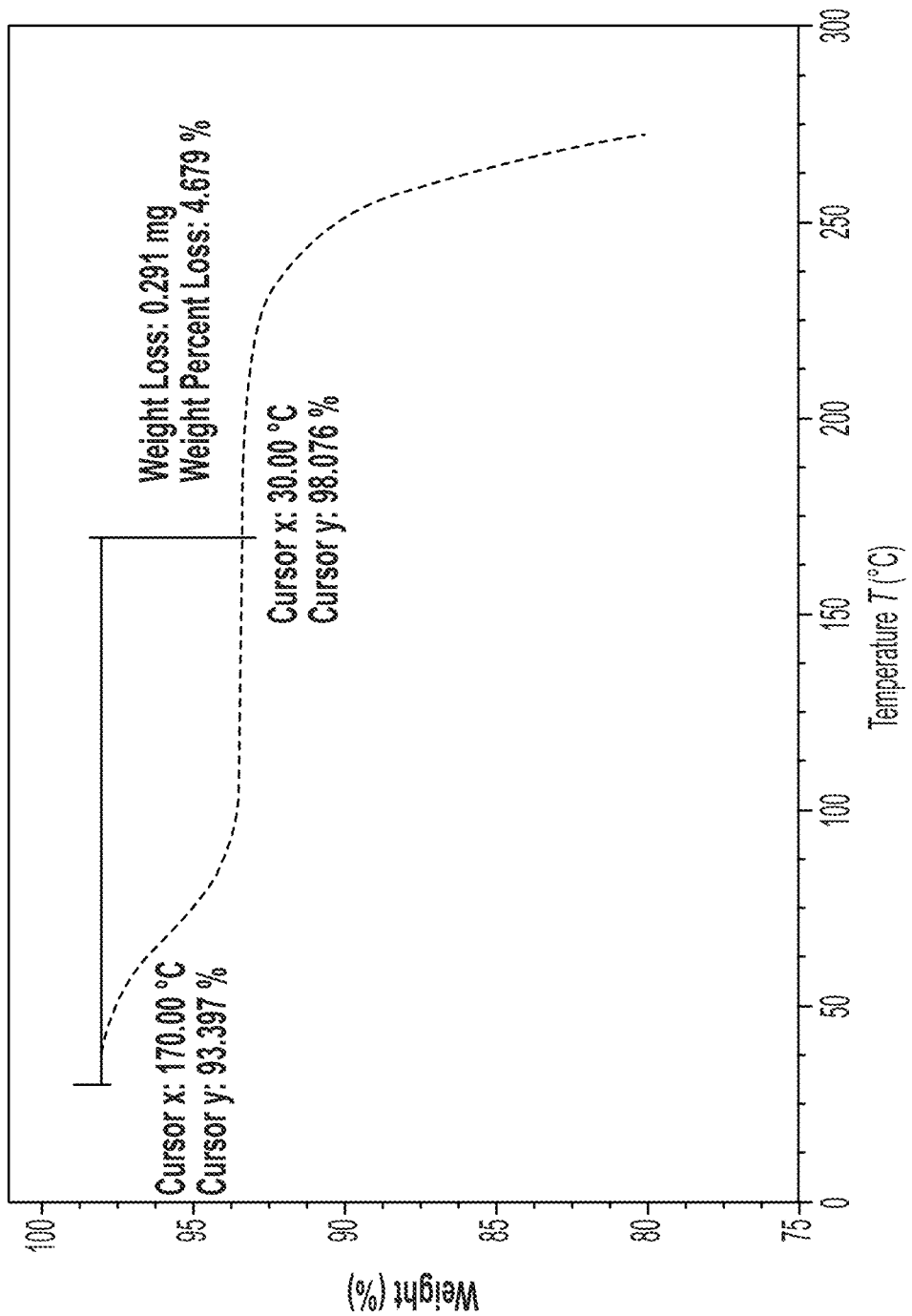
FIG. 12 shows a thermal gravimetric analysis (TGA) thermogram of Compound 1, Form $H_A$.

In embodiments, a representative TGA thermogram of the solid Form $H_A$ of Compound 1 is shown in FIG. 12. In some embodiments, the solid Form $H_A$ of Compound 1 exhibits 4.7% weight loss up to 170° C.

In embodiments, the solid Form $H_A$ of Compound 1 is substantially pure of impurities (e.g., other chemical compounds (i.e., not Compound 1)). In certain embodiments the solid Form $H_A$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $H_A$ of Compound 1 is substantially free of any other solid form of Compound 1. For example, in embodiments, the solid Form $H_A$ of Compound 1 is substantially free of Form A, Form B, Form C, Form D, Form E, Form F, Form $H_B$, Form $S_A$, Form $S_B$, Form $S_C$, Form $S_D$, Form $S_E$, and Form $S_F$. In certain embodiments, the solid Form $H_A$ of Compound 1 comprises less than 15%, less than 10%, or less than 5% by weight of each of Form A, Form B, Form C, Form D, Form E, Form F, Form $H_B$, Form $S_A$, Form $S_B$, Form $S_C$, Form $S_D$, Form $S_E$, and Form $S_F$.

Form $H_B$

In certain embodiments, the invention provides a solid Form $H_B$ of Compound 1. In embodiments, the solid Form $H_B$ of Compound 1 is a monohydrate.

In embodiments, the solid Form $H_B$ of Compound 1 is characterized by high crystallinity.

Figure 13:
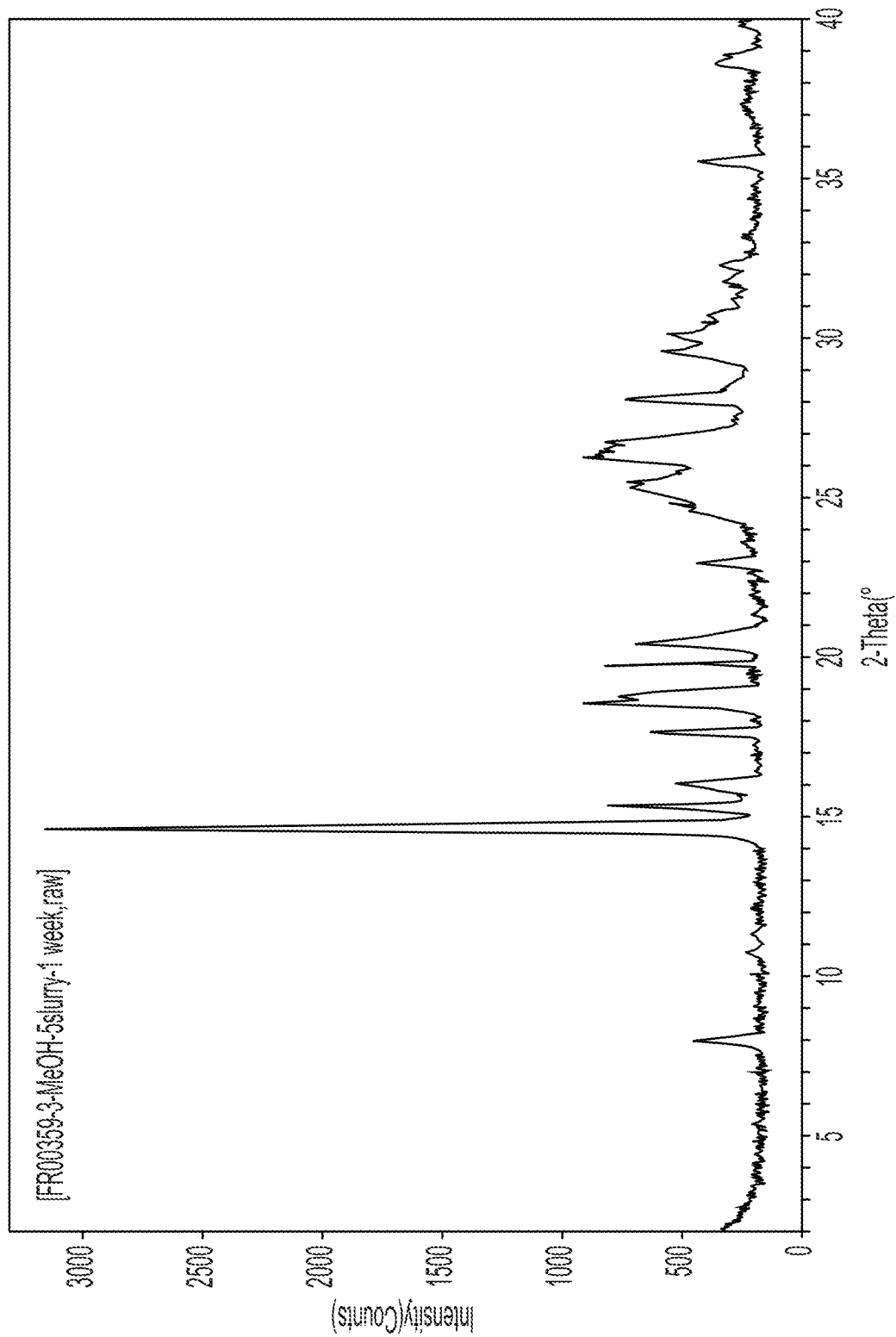
FIG. 13 shows an X-ray powder diffraction (XRPD) analysis of Compound 1, Form $H_B$.

In embodiments, the solid Form $H_B$ of Compound 1 is characterized by an X-ray powder diffraction pattern substantially in accordance with FIG. 13.

In embodiments, the solid Form $H_B$ of Compound 1 is characterized by an X-ray powder diffraction pattern comprising peaks at 14.6, 15.3, 18.5, 20.4, and 28.1±0.2° 2θ.

In embodiments, the solid Form $H_B$ of Compound 1 is characterized by an X-ray powder diffraction pattern comprising peaks at 16.0, 20.4, 26.8, 28.1, and 29.6±0.2° 2θ.

In embodiments, the solid Form $H_B$ of Compound 1 is characterized by an X-ray powder diffraction pattern comprising peaks at 7.9, 14.6, 16.0, 17.6, and 28.1±0.2° 2θ.

In embodiments, the solid Form $H_B$ of Compound 1 is characterized by an X-ray powder diffraction pattern which comprises at least one peak selected from the group consisting of 7.9, 14.6, 15.3, 16.0, 17.6, 18.5, 20.4, 26.8, 28.1, and 29.6±0.2° 2θ.

In embodiments, the solid Form $H_B$ of Compound 1 is characterized by an X-ray powder diffraction pattern which comprises one, two, three, four, and/or five peaks selected from the group consisting of 7.9, 14.6, 15.3, 16.0, 17.6, 18.5, 20.4, 26.8, 28.1, and 29.6±0.2° 2θ.

In embodiments, the solid Form $H_B$ of Compound 1 is characterized by an X-ray powder diffraction pattern comprising one or more peaks expressed in degrees 2θ (±0.2) as listed in Table 5.

TABLE 5

XRPD Data of Solid Form $H_B$ of Compound 1

| Angle 2θ (±0.2) | Relative Intensity (%) |
| --- | --- |
| 5.304 | 1.6 |
| 7.94 | 9.7 |
| 10.739 | 2.5 |
| 11.348 | 1.6 |
| 14.624 | 100 |
| 15.312 | 19.8 |
| 16.043 | 10.7 |
| 17.622 | 14.9 |
| 18.529 | 24.3 |
| 20.387 | 17.6 |
| 22.968 | 8.4 |
| 24.565 | 9.2 |
| 25.334 | 10.2 |
| 26.28 | 16.3 |
| 26.791 | 14.2 |
| 28.115 | 16.5 |
| 28.466 | 2.3 |
| 29.613 | 10.4 |
| 30.108 | 9.9 |
| 31.764 | 3.2 |
| 32.278 | 3.6 |
| 33.294 | 1.7 |
| 35.566 | 8.6 |
| 37.487 | 2.1 |
| 38.609 | 5.5 |

In embodiments, the solid Form $H_B$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, and/or twenty-five peaks expressed in degrees 2θ (±0.2) as listed in Table 5.

In embodiments, the solid Form $H_B$ of Compound 1 is characterized by an X-ray powder diffraction pattern comprising five peaks expressed in degrees 2θ (±0.2) as listed in Table 5.

In embodiments, the solid Form $H_B$ of Compound 1 is characterized by an X-ray powder diffraction pattern comprising ten peaks expressed in degrees 2θ (±0.2) as listed in Table 5.

In embodiments, the solid Form $H_B$ of Compound 1 is characterized by an X-ray powder diffraction pattern comprising fifteen peaks expressed in degrees 2θ (±0.2) as listed in Table 5.

In embodiments, the solid Form $H_B$ of Compound 1 is characterized by an X-ray powder diffraction pattern comprising twenty peaks expressed in degrees 2θ (±0.2) as listed in Table 5.

In embodiments, the solid Form $H_B$ of Compound 1 is characterized by an X-ray powder diffraction pattern comprising twenty-five peaks expressed in degrees 2θ (±0.2) as listed in Table 5.

Figure 14:
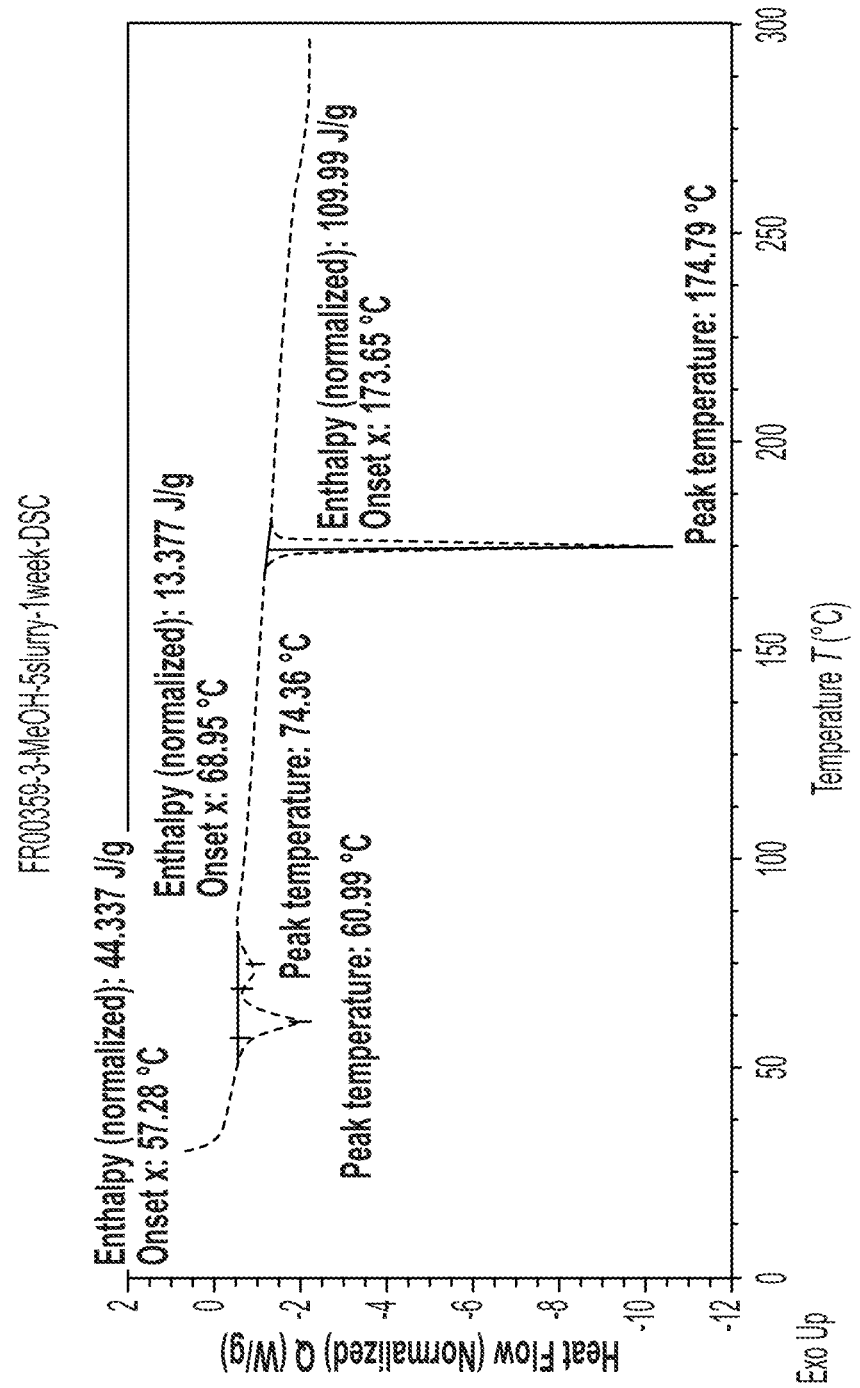
FIG. 14 shows a differential scanning calorimetry (DSC) thermogram of Compound 1, Form $H_B$.

In embodiments, the solid Form $H_B$ of Compound 1 is characterized by a differential scanning calorimetry thermogram having characteristic endotherm peaks at 70.0° C., 74.4° C., and 174.8° C. (FIG. 14).

In embodiments, the solid Form $H_B$ of Compound 1 is characterized by a differential scanning calorimetry thermogram having characteristic endotherm onset temperatures at 57.3° C., 69.0° C., and 173.7° C. (FIG. 14).

Figure 15:
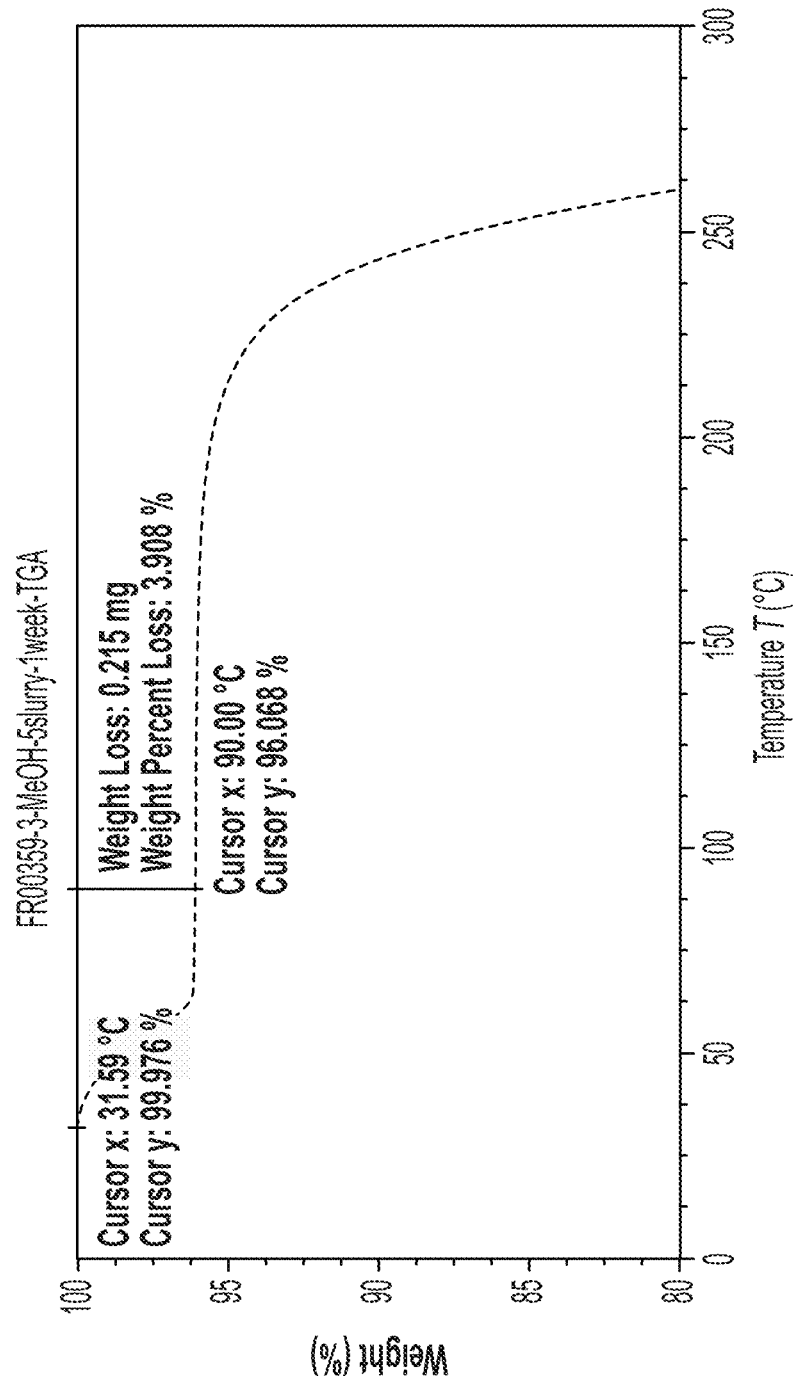
FIG. 15 shows a thermal gravimetric analysis (TGA) thermogram of Compound 1, Form $H_B$.

In embodiments, a representative TGA thermogram of the solid Form $H_B$ of Compound 1 is shown in FIG. 15. In some embodiments, the solid Form $H_B$ of Compound 1 exhibits 3.9% weight loss up to 170° C.

In embodiments, the solid Form $H_B$ of Compound 1 is substantially pure of impurities (e.g., other chemical compounds (i.e., not Compound 1)). In certain embodiments the solid Form $H_B$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $H_B$ of Compound 1 is substantially free of any other solid form of Compound 1. For example, in embodiments, the solid Form $H_B$ of Compound 1 is substantially free of Form A, Form B, Form C, Form D, Form E, Form F, Form $H_A$, Form $S_A$, Form $S_B$, Form $S_C$, Form $S_D$, Form $S_E$, and Form $S_F$. In certain embodiments, the solid Form $H_B$ of Compound 1 comprises less than 15%, less than 10%, or less than 5% by weight of each of Form A, Form B, Form C, Form D, Form E, Form F, Form $H_A$, Form $S_A$, Form $S_B$, Form $S_C$, Form $S_D$, Form $S_E$, and Form $S_F$.

Form $S_A$

In certain embodiments, the invention provides a solid Form $S_A$ of Compound 1. In embodiments, the solid Form $S_A$ of Compound 1 is a non-stoichiometric 1,4-dioxane solvate, with a molar ratio of Compound 1 to 1,4-dioxane of about 1:1.2.

In embodiments, the solid Form $S_A$ of Compound 1 is characterized by high crystallinity.

Figure 16:
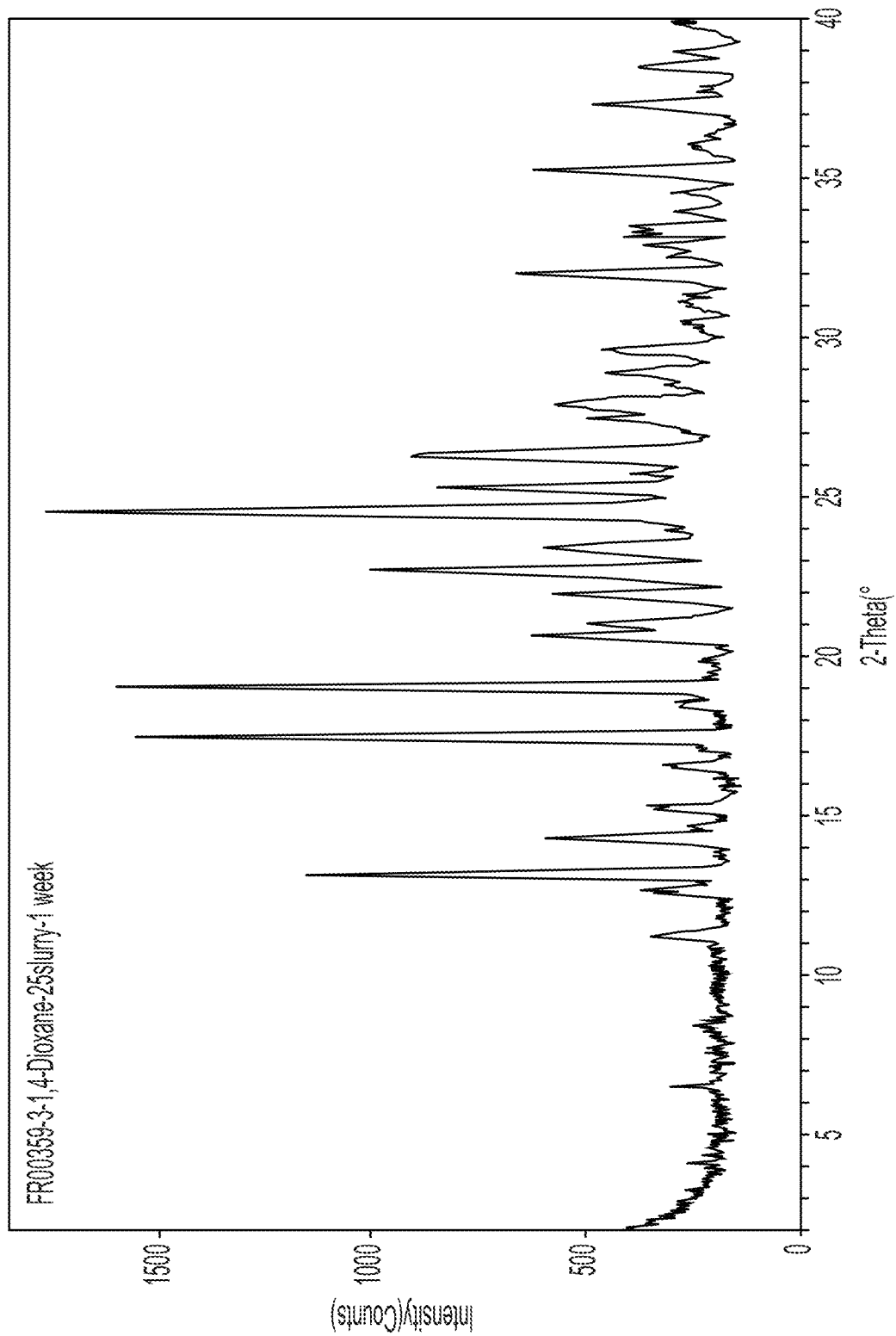
FIG. 16 shows an X-ray powder diffraction (XRPD) analysis of Compound 1, Form $S_A$.

In embodiments, the solid Form $S_A$ of Compound 1 is characterized by an X-ray powder diffraction pattern substantially in accordance with FIG. 16.

In embodiments, the solid Form $S_A$ of Compound 1 is characterized by an X-ray powder diffraction pattern comprising peaks at 13.1, 17.5, 19.1, 22.7, and 24.6±0.2° 2θ.

In embodiments, the solid Form $S_A$ of Compound 1 is characterized by an X-ray powder diffraction pattern comprising peaks at 13.1, 17.5, 19.1, 24.6, and 32.0±0.2° 2θ.

In embodiments, the solid Form $S_A$ of Compound 1 is characterized by an X-ray powder diffraction pattern comprising peaks at 13.1, 17.5, 19.1, 32.0, and 35.3±0.2° 2θ.

In embodiments, the solid Form $S_A$ of Compound 1 is characterized by an X-ray powder diffraction pattern which comprises at least one peak selected from the group consisting of 13.1, 17.5, 19.1, 22.7, 24.6, 32.0, and 35.3±0.2° 2θ.

In embodiments, the solid Form $S_A$ of Compound 1 is characterized by an X-ray powder diffraction pattern which comprises one, two, three, four, and/or five peaks selected from the group consisting of 13.1, 17.5, 19.1, 22.7, 24.6, 32.0, and 35.3±0.2° 2θ.

In embodiments, the solid Form $S_A$ of Compound 1 is characterized by an X-ray powder diffraction pattern comprising one or more peaks expressed in degrees 2θ (±0.2) as listed in Table 6.

TABLE 6

XRPD Data of Solid Form $S_A$ of Compound 1

| Angle 2θ (±0.2) | Relative Intensity (%) |
| --- | --- |
| 4.144 | 4.6 |
| 6.539 | 8.5 |
| 8.432 | 5.2 |
| 11.248 | 11.7 |
| 12.672 | 13.5 |
| 13.134 | 66.5 |
| 14.307 | 28.4 |
| 14.736 | 6 |
| 15.293 | 12.6 |
| 16.615 | 9.4 |
| 17.483 | 92.6 |
| 18.433 | 6 |
| 19.062 | 95.9 |
| 20.661 | 30.6 |
| 21.015 | 22 |
| 21.98 | 24.4 |
| 22.749 | 51.6 |
| 23.402 | 23.6 |
| 24.622 | 100 |
| 25.294 | 35.4 |
| 25.731 | 6 |
| 26.359 | 43.8 |
| 27.463 | 17.9 |
| 27.897 | 22.2 |
| 28.529 | 4.5 |
| 28.865 | 14.4 |
| 29.593 | 17.9 |
| 30.48 | 6.4 |
| 31.353 | 5.3 |
| 32.001 | 31.5 |
| 32.572 | 7.7 |
| 32.927 | 11.5 |
| 33.497 | 12.8 |
| 33.972 | 6.9 |
| 34.547 | 8.2 |
| 35.272 | 30.9 |
| 36.026 | 7.5 |
| 36.362 | 4.5 |
| 37.345 | 22 |
| 37.861 | 4.7 |
| 38.49 | 15 |
| 38.963 | 9.4 |

In embodiments, the solid Form $S_A$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, and/or forty-two peaks expressed in degrees 2θ (±0.2) as listed in Table 6.

In embodiments, the solid Form $S_A$ of Compound 1 is characterized by an X-ray powder diffraction pattern comprising five peaks expressed in degrees 2θ (±0.2) as listed in Table 6.

In embodiments, the solid Form $S_A$ of Compound 1 is characterized by an X-ray powder diffraction pattern comprising ten peaks expressed in degrees 2θ (±0.2) as listed in Table 6.

In embodiments, the solid Form $S_A$ of Compound 1 is characterized by an X-ray powder diffraction pattern comprising fifteen peaks expressed in degrees 2θ (±0.2) as listed in Table 6.

In embodiments, the solid Form $S_A$ of Compound 1 is characterized by an X-ray powder diffraction pattern comprising twenty peaks expressed in degrees 2θ (±0.2) as listed in Table 6.

In embodiments, the solid Form $S_A$ of Compound 1 is characterized by an X-ray powder diffraction pattern comprising twenty-five peaks expressed in degrees 2θ (±0.2) as listed in Table 6.

In embodiments, the solid Form $S_A$ of Compound 1 is characterized by an X-ray powder diffraction pattern comprising thirty peaks expressed in degrees 2θ (±0.2) as listed in Table 6.

In embodiments, the solid Form $S_A$ of Compound 1 is characterized by an X-ray powder diffraction pattern comprising thirty-five peaks expressed in degrees 2θ (±0.2) as listed in Table 6.

In embodiments, the solid Form $S_A$ of Compound 1 is characterized by an X-ray powder diffraction pattern comprising forty peaks expressed in degrees 2θ (±0.2) as listed in Table 6.

In embodiments, the solid Form $S_A$ of Compound 1 is characterized by an X-ray powder diffraction pattern comprising forty-two peaks expressed in degrees 2θ (±0.2) as listed in Table 6.

Figure 17:
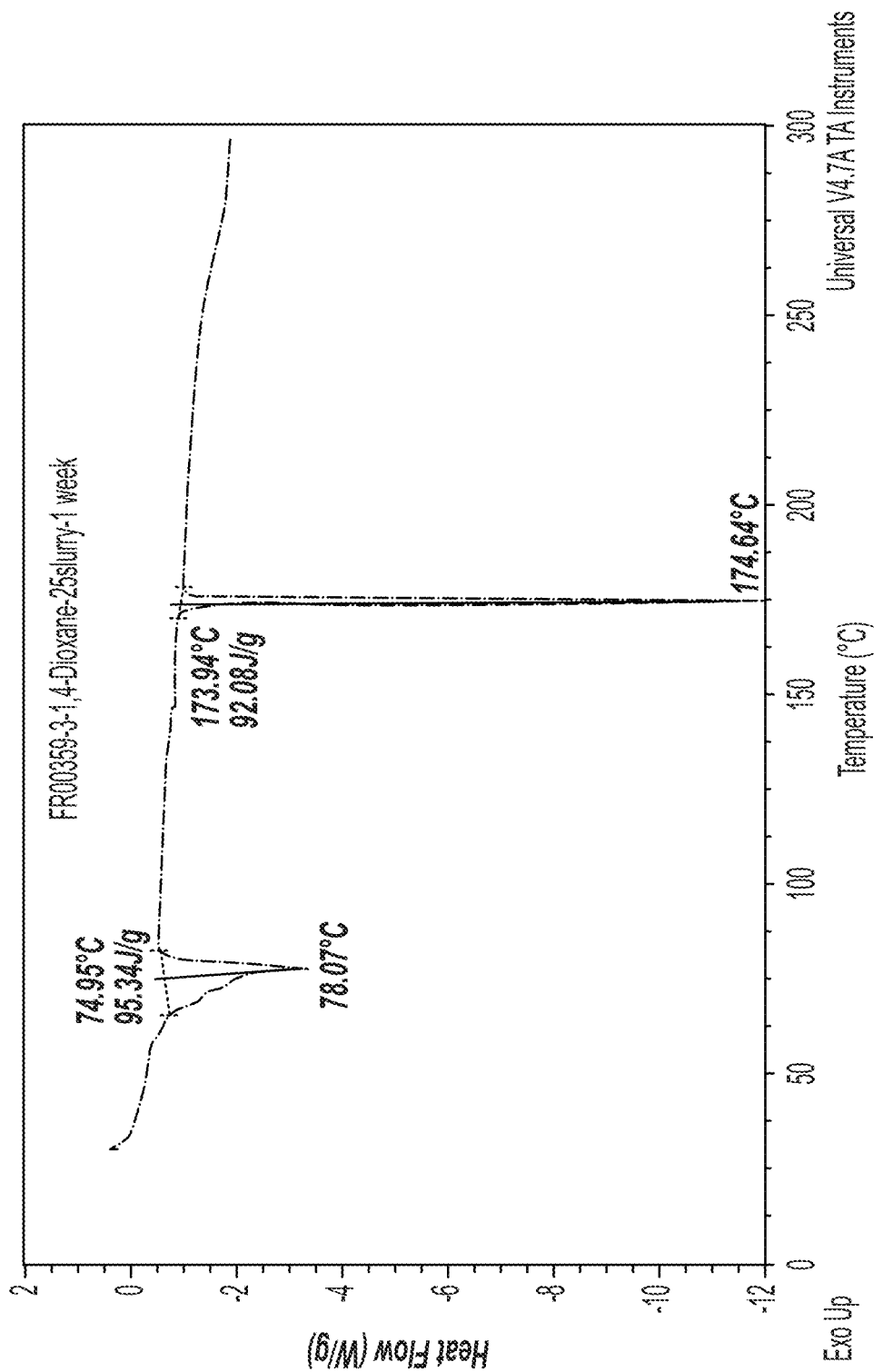
FIG. 17 shows a differential scanning calorimetry (DSC) thermogram of Compound 1, Form $S_A$.

In embodiments, the solid Form $S_A$ of Compound 1 is characterized by a differential scanning calorimetry thermogram having characteristic endotherm peaks at 78.1° C. and 174.6° C. (FIG. 17).

In embodiments, the solid Form $S_A$ of Compound 1 is characterized by a differential scanning calorimetry thermogram having characteristic endotherm onset temperatures at 75.0° C. and 173.9° C. (FIG. 17).

Figure 18:
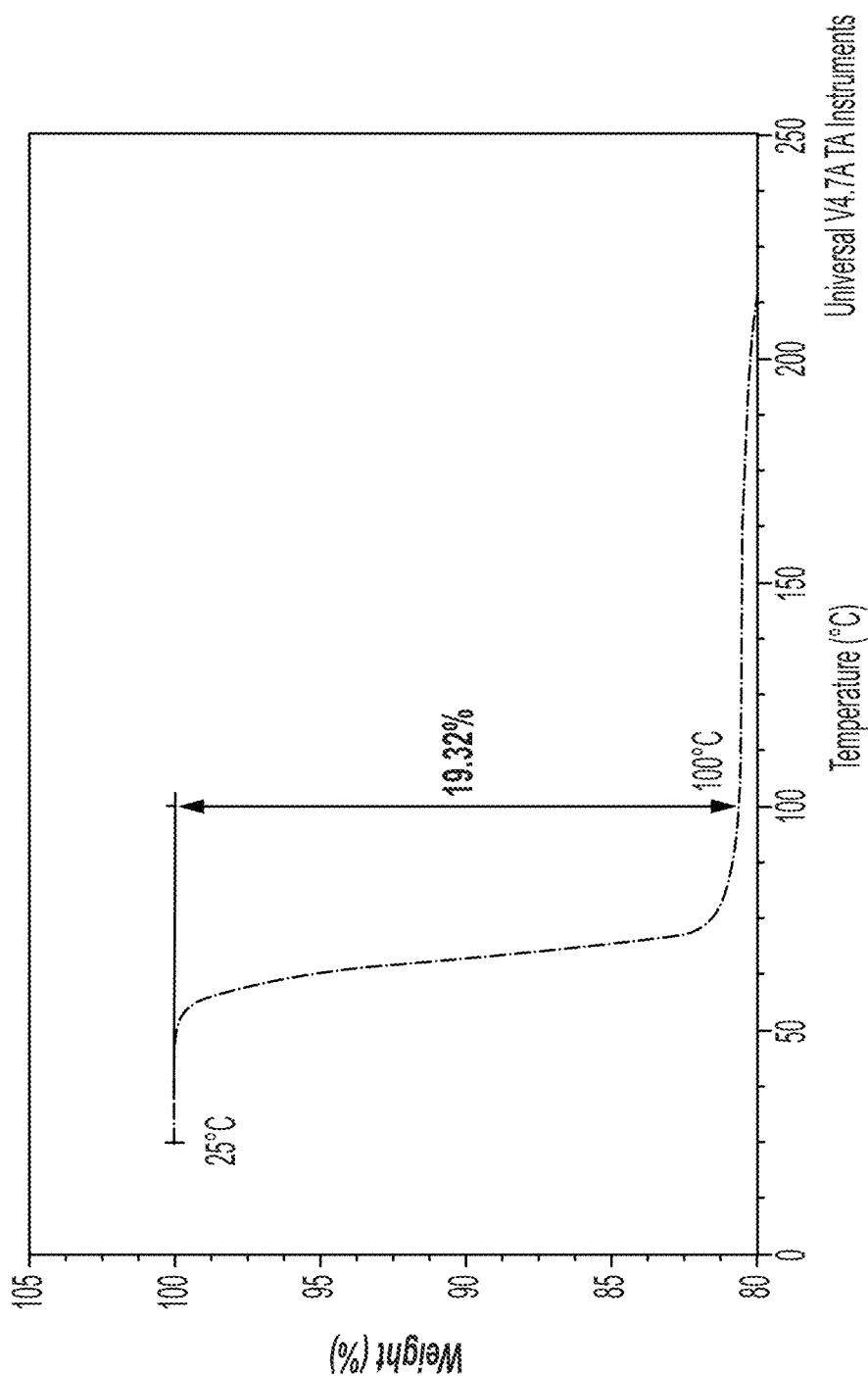
FIG. 18 shows a thermal gravimetric analysis (TGA) thermogram of Compound 1, Form $S_A$.

In embodiments, a representative TGA thermogram of the solid Form $S_A$ of Compound 1 is shown in FIG. 18. In some embodiments, the solid Form $S_A$ of Compound 1 exhibits 19.3% weight loss.

In embodiments, the solid Form $S_A$ of Compound 1 is substantially pure of impurities (e.g., other chemical compounds (i.e., not Compound 1)). In certain embodiments the solid Form $S_A$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $S_A$ of Compound 1 is substantially free of any other solid form of Compound 1. For example, in embodiments, the solid Form $S_A$ of Compound 1 is substantially free of Form A, Form B, Form C, Form D, Form E, Form F, Form $H_A$, Form $H_B$, Form $S_B$, Form $S_C$, Form $S_D$, Form $S_E$, and Form $S_F$. In certain embodiments, the solid Form $S_A$ of Compound 1 comprises less than 15%, less than 10%, or less than 5% by weight of each of Form A, Form B, Form C, Form D, Form E, Form F, Form $H_A$, Form $H_B$, Form $S_B$, Form $S_C$, Form $S_D$, Form $S_E$, and Form $S_F$.

Form $S_B$

In certain embodiments, the invention provides a solid Form $S_B$ of Compound 1. In embodiments, the solid Form $S_B$ of Compound 1 is a non-stoichiometric 1,4-dioxane solvate, with a molar ratio of Compound 1 to 1,4-dioxane of about 1:1.4.

In embodiments, the solid Form $S_B$ of Compound 1 is characterized by high crystallinity.

Figure 19:
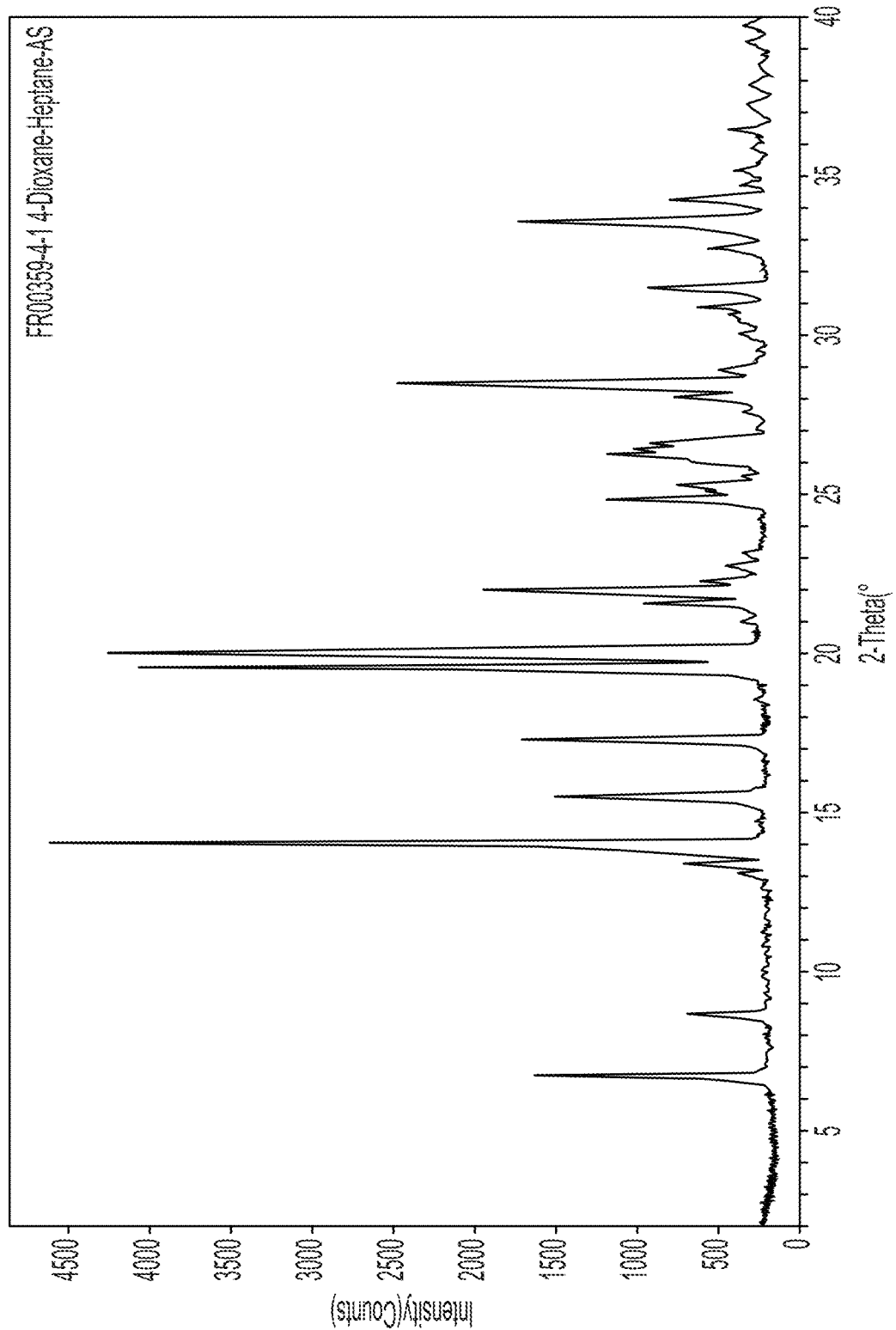
FIG. 19 shows an X-ray powder diffraction (XRPD) analysis of Compound 1, Form $S_B$.

In embodiments, the solid Form $S_B$ of Compound 1 is characterized by an X-ray powder diffraction pattern substantially in accordance with FIG. 19.

In embodiments, the solid Form $S_B$ of Compound 1 is characterized by an X-ray powder diffraction pattern comprising peaks at 14.0, 19.6, 20.0, 22.0, and 28.5±0.2° 2θ.

In embodiments, solid Form $S_B$ of Compound 1 has an X-ray powder diffraction pattern comprising peaks at 14.0, 19.6, 20.0, 31.5, and 33.6±0.2° 2θ.

In embodiments, solid Form $S_B$ of Compound 1 has an X-ray powder diffraction pattern comprising peaks at 6.8, 14.0, 17.3, 19.6, 20.0, and 28.5±0.2° 2θ.

In embodiments, solid Form $S_B$ of Compound 1 has an X-ray powder diffraction pattern which comprises at least one peak selected from the group consisting of 6.8, 14.0, 17.3, 19.6, 20.0, 22.0, 28.5, 31.5, and 33.6±0.2° 2θ.

In embodiments, solid Form $S_B$ of Compound 1 has an X-ray powder diffraction pattern which comprises one, two, three, four, five, and/or six peaks selected from the group consisting of 6.8, 14.0, 17.3, 19.6, 20.0, 22.0, 28.5, 31.5, and 33.6±0.2° 2θ.

In embodiments, the solid Form $S_B$ of Compound 1 is characterized by an X-ray powder diffraction pattern comprising one or more peaks expressed in degrees 2θ (±0.2) as listed in Table 7.

TABLE 7

XRPD Data of Solid Form $S_B$ of Compound 1

| Angle 2θ (±0.2) | Relative Intensity (%) |
| --- | --- |
| 6.753 | 33.3 |
| 8.704 | 11.5 |
| 13.399 | 11.1 |
| 13.797 | 20.1 |
| 14.029 | 100 |
| 15.509 | 29.3 |
| 17.286 | 34.2 |
| 18.569 | 1.8 |
| 19.574 | 87.4 |
| 20.028 | 91.6 |
| 20.992 | 2.3 |
| 21.584 | 15.6 |
| 21.961 | 38.6 |
| 22.26 | 7.8 |
| 22.731 | 3.7 |
| 24.858 | 21.5 |
| 25.255 | 11.2 |
| 25.526 | 1.8 |
| 26.008 | 9.1 |
| 26.24 | 20.9 |
| 26.616 | 15.5 |
| 27.578 | 1.9 |
| 28.055 | 12.1 |
| 28.469 | 51.1 |
| 28.867 | 5.2 |
| 30.009 | 2.8 |
| 30.441 | 3.4 |
| 30.858 | 8.9 |
| 31.505 | 16 |
| 32.73 | 7.2 |

TABLE 7-continued

XRPD Data of Solid Form $S_B$ of Compound 1

| Angle 2θ (±0.2) | Relative Intensity (%) |
|---|---|
| 33.282 | 10 |
| 33.56 | 33.5 |
| 34.248 | 12.3 |
| 34.725 | 2.9 |
| 35.119 | 4.1 |
| 35.868 | 1.9 |
| 36.439 | 5.6 |
| 37.248 | 3.2 |
| 37.838 | 2.8 |
| 38.486 | 1.4 |
| 39.18 | 2.8 |
| 39.639 | 2.9 |

In embodiments, the solid Form $S_B$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, and/or forty-two peaks expressed in degrees 2θ (±0.2) as listed in Table 7.

In embodiments, the solid Form $S_B$ of Compound 1 is characterized by an X-ray powder diffraction pattern comprising five peaks expressed in degrees 2θ (±0.2) as listed in Table 7.

In embodiments, the solid Form $S_B$ of Compound 1 is characterized by an X-ray powder diffraction pattern comprising ten peaks expressed in degrees 2θ (±0.2) as listed in Table 7.

In embodiments, the solid Form $S_B$ of Compound 1 is characterized by an X-ray powder diffraction pattern comprising fifteen peaks expressed in degrees 2θ (±0.2) as listed in Table 7.

In embodiments, the solid Form $S_B$ of Compound 1 is characterized by an X-ray powder diffraction pattern comprising twenty peaks expressed in degrees 2θ (±0.2) as listed in Table 7.

In embodiments, the solid Form $S_B$ of Compound 1 is characterized by an X-ray powder diffraction pattern comprising twenty-five peaks expressed in degrees 2θ (±0.2) as listed in Table 7.

In embodiments, the solid Form $S_B$ of Compound 1 is characterized by an X-ray powder diffraction pattern comprising thirty peaks expressed in degrees 2θ (±0.2) as listed in Table 7.

In embodiments, the solid Form $S_B$ of Compound 1 is characterized by an X-ray powder diffraction pattern comprising thirty-five peaks expressed in degrees 2θ (±0.2) as listed in Table 7.

In embodiments, the solid Form $S_B$ of Compound 1 is characterized by an X-ray powder diffraction pattern comprising forty peaks expressed in degrees 2θ (±0.2) as listed in Table 7.

In embodiments, the solid Form $S_B$ of Compound 1 is characterized by an X-ray powder diffraction pattern comprising forty-five peaks expressed in degrees 2θ (±0.2) as listed in Table 7.

Figure 20:
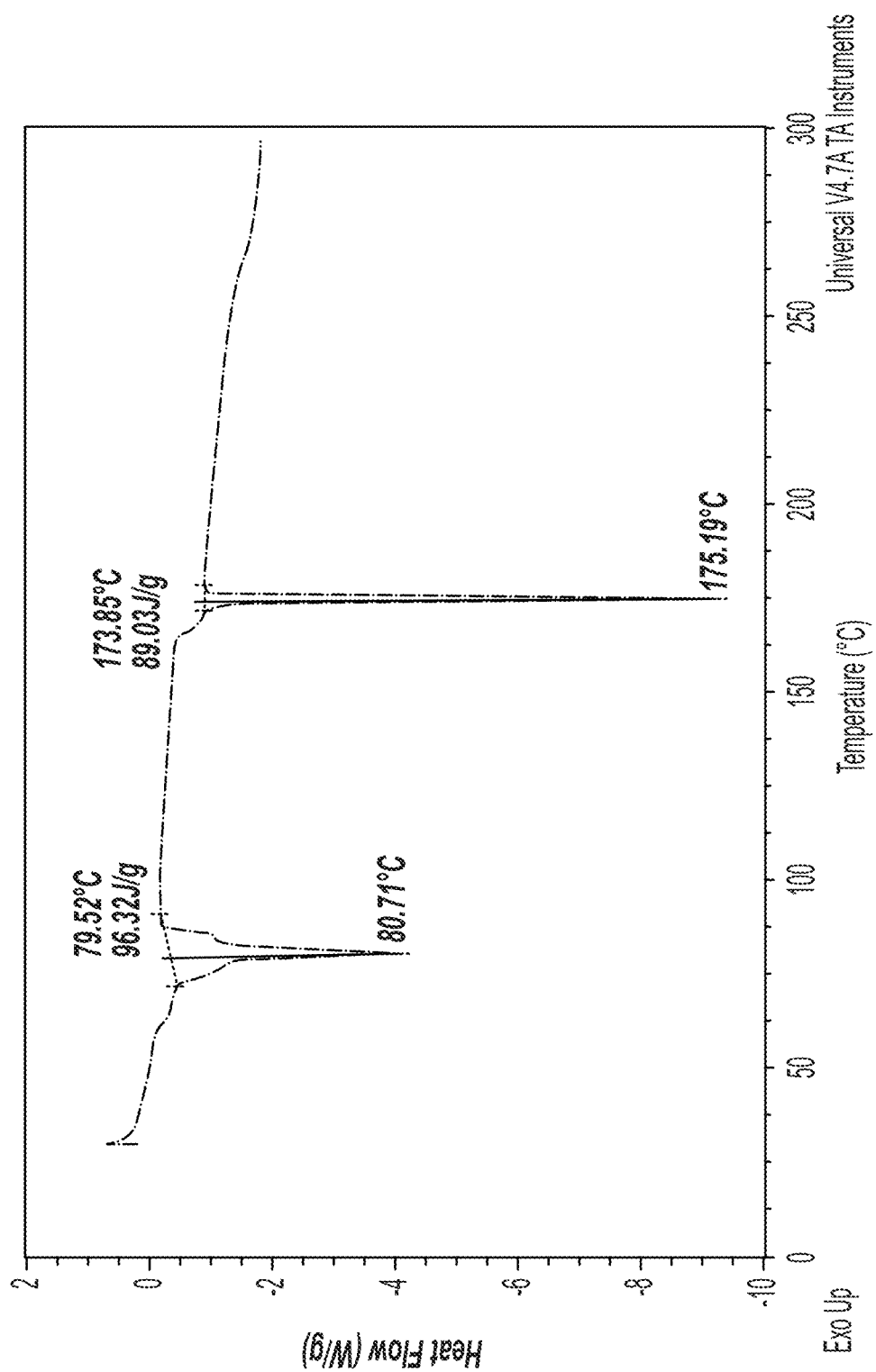
FIG. 20 shows a differential scanning calorimetry (DSC) thermogram of Compound 1, Form $S_B$.

In embodiments, the solid Form $S_B$ of Compound 1 is characterized by a differential scanning calorimetry thermogram having endotherm peaks at 80.7° C. and 175.2° C. (FIG. 20).

In embodiments, the solid Form $S_B$ of Compound 1 is characterized by a differential scanning calorimetry thermogram having characteristic endotherm onset temperatures at 79.5° C. and 173.9° C. (FIG. 20).

Figure 21:
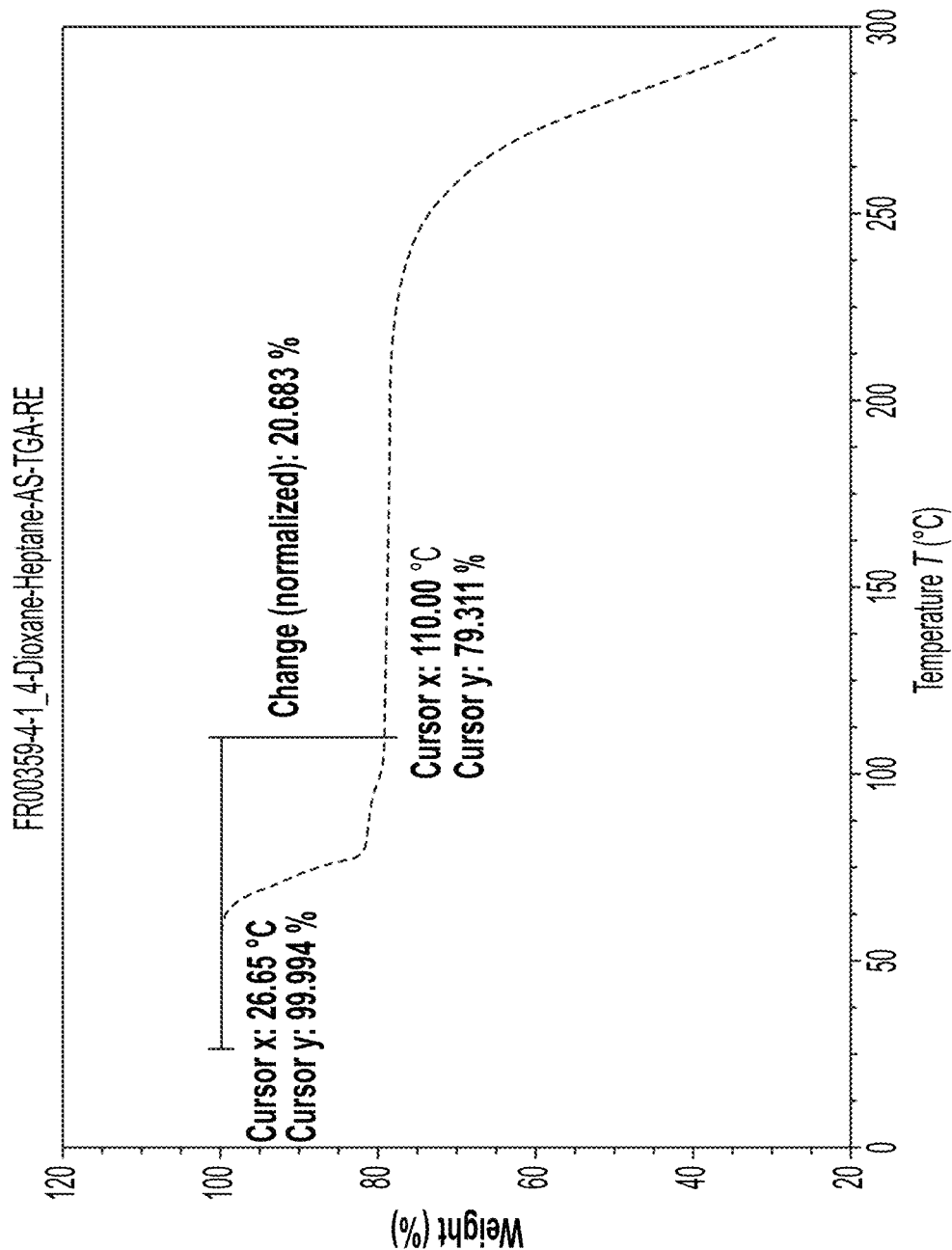
FIG. 21 shows a thermal gravimetric analysis (TGA) thermogram of Compound 1, Form $S_B$.

In embodiments, a representative TGA thermogram of the solid Form $S_B$ of Compound 1 is shown in FIG. 21. In some embodiments, the solid Form $S_B$ of Compound 1 exhibits 20.7% weight loss.

In embodiments, the solid Form $S_B$ of Compound 1 is substantially pure of impurities (e.g., other chemical compounds (i.e., not Compound 1)). In certain embodiments the solid Form $S_B$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $S_B$ of Compound 1 is substantially free of any other solid form of Compound 1. For example, in embodiments, the solid Form $S_B$ of Compound 1 is substantially free of Form A, Form B, Form C, Form D, Form E, Form F, Form $H_A$, Form $H_B$, Form $S_A$, Form $S_C$, Form $S_D$, Form $S_E$, and Form $S_F$. In certain embodiments, the solid Form $S_B$ of Compound 1 comprises less than 15%, less than 10%, or less than 5% by weight of each of Form A, Form B, Form C, Form D, Form E, Form F, Form $H_A$, Form $H_B$, Form $S_A$, Form $S_C$, Form $S_D$, Form $S_E$, and Form $S_F$.

Form $S_C$

In certain embodiments, the invention provides a solid Form $S_C$ of Compound 1. In embodiments, the solid Form $S_C$ of Compound 1 is a non-stoichiometric 1,4-dioxane solvate, with a molar ratio of Compound 1 to 1,4-dioxane of about 1:0.6.

In embodiments, the solid Form $S_C$ of Compound 1 is characterized by high crystallinity.

Figure 22:
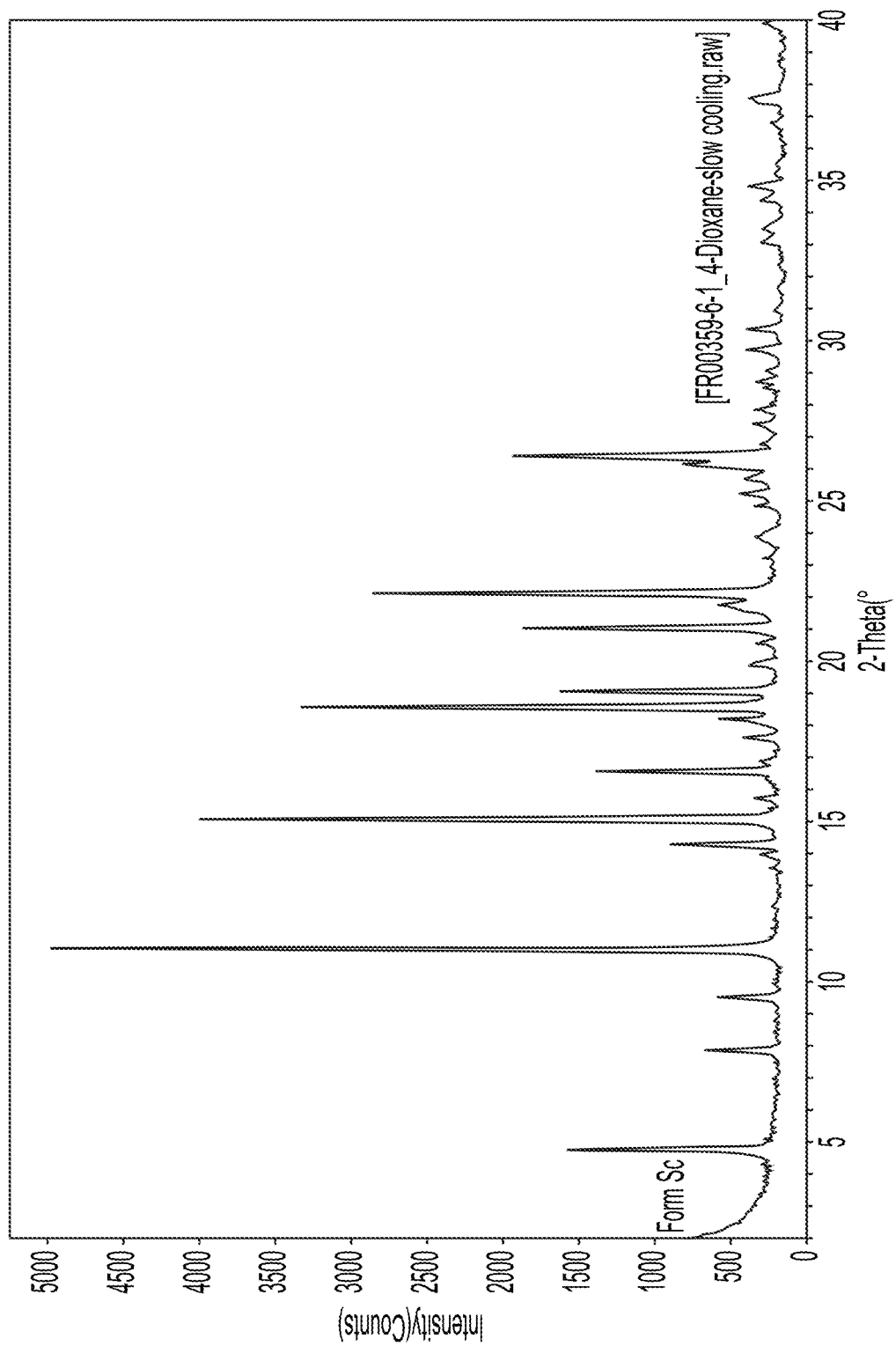
FIG. 22 shows an X-ray powder diffraction (XRPD) analysis of Compound 1, Form $S_C$.

In embodiments, the solid Form $S_C$ of Compound 1 is characterized by an X-ray powder diffraction pattern substantially in accordance with FIG. 22.

In embodiments, the solid Form $S_C$ of Compound 1 is characterized by an X-ray powder diffraction pattern comprising peaks at 11.0, 15.1, 18.6, 22.1, and 26.4±0.2° 2θ.

In embodiments, the solid Form $S_C$ of Compound 1 is characterized by an X-ray powder diffraction pattern comprising peaks at 4.8, 9.5, 11.0, 21.8, and 34.8±0.2° 2θ.

In embodiments, the solid Form $S_C$ of Compound 1 is characterized by an X-ray powder diffraction pattern comprising peaks at 4.8, 7.9, 14.3, 18.6, 21.1, and 22.1±0.2° 2θ.

In embodiments, the solid Form $S_C$ of Compound 1 is characterized by an X-ray powder diffraction pattern which comprises at least one peak selected from the group consisting of 4.8, 7.9, 9.5, 11.0, 14.3, 15.1, 18.6, 21.1, 21.8, 22.1, 26.4, and 34.8±0.2° 2θ.

In embodiments, the solid Form $S_C$ of Compound 1 is characterized by an X-ray powder diffraction pattern which comprises one, two, three, four, and/or five peaks selected from the group consisting of 4.8, 7.9, 9.5, 11.0, 14.3, 15.1, 18.6, 21.1, 21.8, 22.1, 26.4, and 34.8±0.2° 2θ.

In embodiments, the solid Form $S_C$ of Compound 1 is characterized by an X-ray powder diffraction pattern comprising one or more peaks expressed in degrees 2θ (±0.2) as listed in Table 8.

TABLE 8

XRPD Data of Solid Form $S_C$ of Compound 1

| Angle 2θ (±0.2) | Relative Intensity (%) |
| --- | --- |
| 4.766 | 28.1 |
| 7.877 | 10 |
| 9.549 | 8.7 |
| 11.054 | 100 |
| 13.976 | 2.6 |
| 14.29 | 14.6 |
| 15.098 | 79.4 |
| 15.746 | 3.1 |
| 16.594 | 24.9 |
| 16.874 | 2.5 |
| 17.638 | 4.9 |
| 18.606 | 65.3 |
| 19.081 | 28.9 |
| 19.945 | 3.2 |
| 21.053 | 33.9 |
| 21.764 | 7.8 |
| 22.141 | 54.8 |
| 23.227 | 1.7 |
| 23.911 | 3 |
| 24.863 | 3.1 |
| 25.237 | 4.5 |
| 25.671 | 3.7 |
| 26.179 | 12.3 |
| 26.419 | 35.8 |
| 27.419 | 3.2 |
| 27.84 | 2.9 |
| 28.726 | 2.8 |
| 29.084 | 1.8 |
| 29.731 | 4.7 |
| 30.385 | 4.8 |
| 30.97 | 1.4 |
| 33.089 | 3 |
| 33.5 | 2.7 |
| 34.422 | 2.8 |
| 34.839 | 4.9 |
| 35.178 | 1.2 |
| 35.533 | 1.2 |
| 36.827 | 1.7 |
| 37.601 | 4.7 |
| 38.96 | 1 |

In embodiments, the solid Form $S_C$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, and/or forty peaks expressed in degrees 2θ (±0.2) as listed in Table 8.

In embodiments, the solid Form $S_C$ of Compound 1 is characterized by an X-ray powder diffraction pattern comprising five peaks expressed in degrees 2θ (±0.2) as listed in Table 8.

In embodiments, the solid Form $S_C$ of Compound 1 is characterized by an X-ray powder diffraction pattern comprising ten peaks expressed in degrees 2θ (±0.2) as listed in Table 8.

In embodiments, the solid Form $S_C$ of Compound 1 is characterized by an X-ray powder diffraction pattern comprising fifteen peaks expressed in degrees 2θ (±0.2) as listed in Table 8.

In embodiments, the solid Form $S_C$ of Compound 1 is characterized by an X-ray powder diffraction pattern comprising twenty peaks expressed in degrees 2θ (±0.2) as listed in Table 8.

In embodiments, the solid Form $S_C$ of Compound 1 is characterized by an X-ray powder diffraction pattern comprising twenty-five peaks expressed in degrees 2θ (±0.2) as listed in Table 8.

In embodiments, the solid Form $S_C$ of Compound 1 is characterized by an X-ray powder diffraction pattern comprising thirty peaks expressed in degrees 2θ (±0.2) as listed in Table 8.

In embodiments, the solid Form $S_C$ of Compound 1 is characterized by an X-ray powder diffraction pattern comprising thirty-five peaks expressed in degrees 2θ (±0.2) as listed in Table 8.

In embodiments, the solid Form $S_C$ of Compound 1 is characterized by an X-ray powder diffraction pattern comprising forty peaks expressed in degrees 2θ (±0.2) as listed in Table 8.

Figure 23:
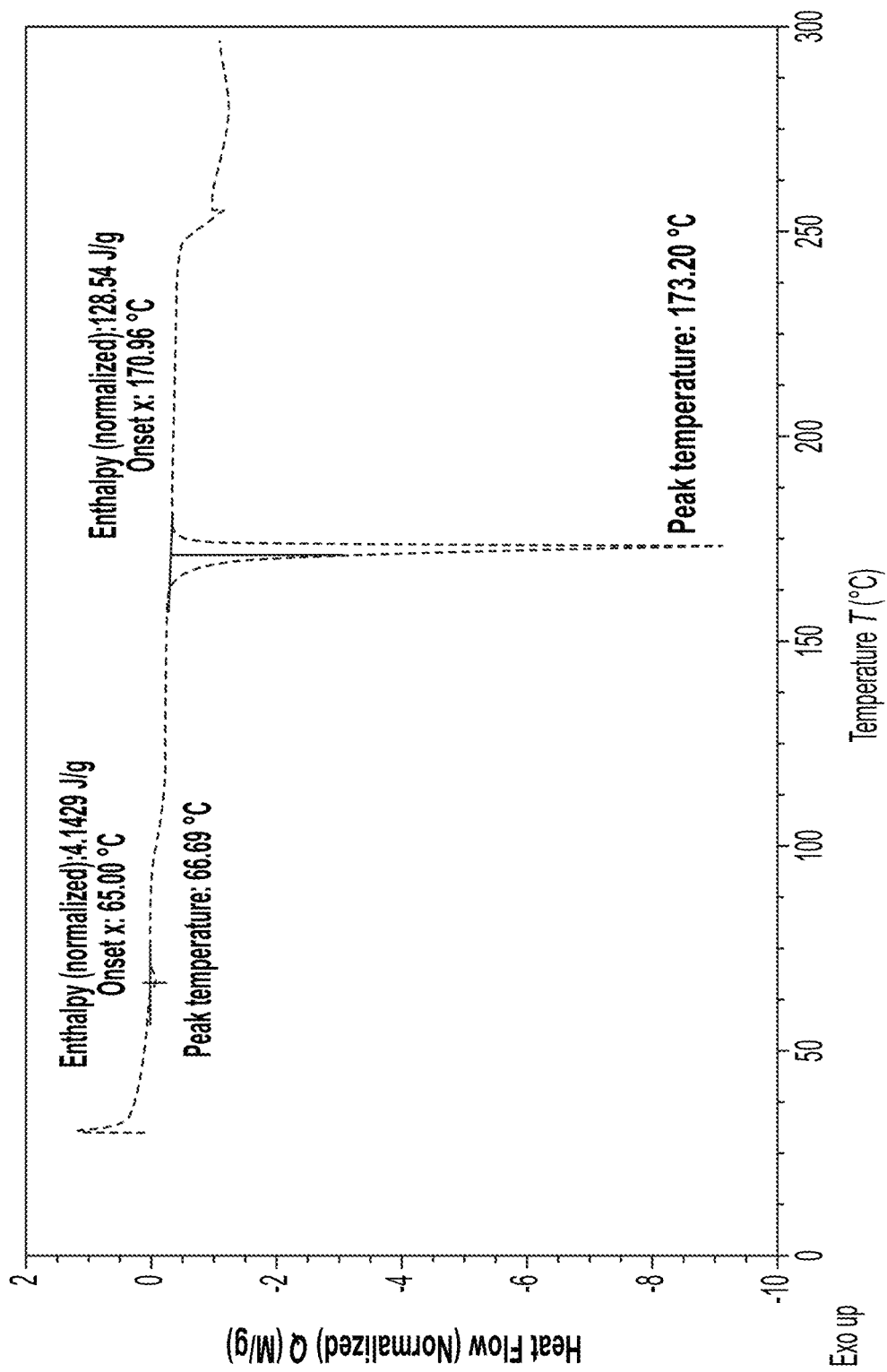
FIG. 23 shows a differential scanning calorimetry (DSC) thermogram of Compound 1, Form $S_C$.

In embodiments, the solid Form $S_C$ of Compound 1 is characterized by a differential scanning calorimetry thermogram having characteristic endotherm peaks at 66.7° C. and 173.3° C. (FIG. 23).

In embodiments, the solid Form $S_C$ of Compound 1 is characterized by a differential scanning calorimetry thermogram having characteristic endotherm onset temperatures at 65.0° C. and 171.0° C. (FIG. 23).

Figure 24:
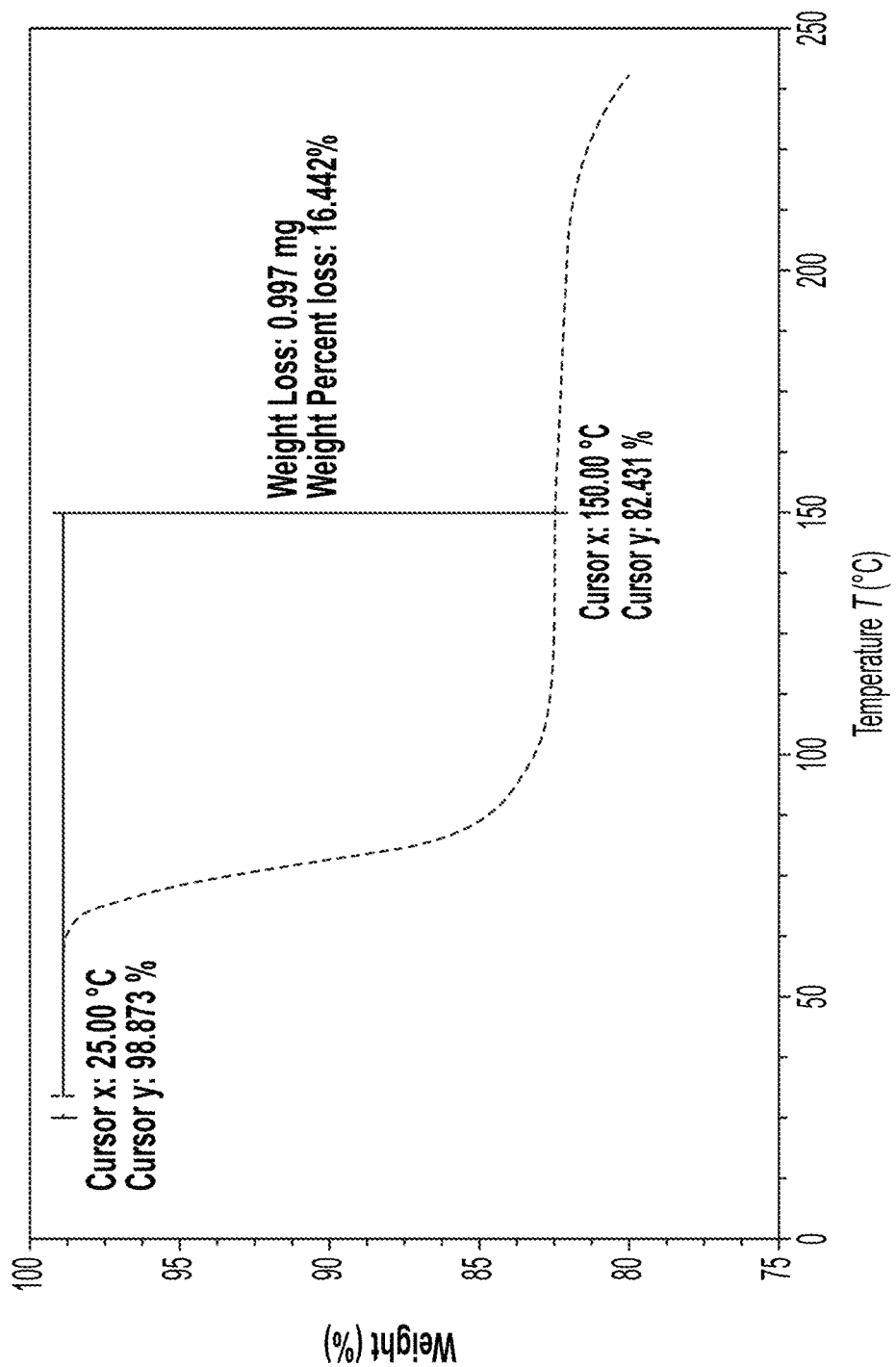
FIG. 24 shows a thermal gravimetric analysis (TGA) thermogram of Compound 1, Form $S_C$.

In embodiments, a representative TGA thermogram of the solid Form $S_C$ of Compound 1 is shown in FIG. 24. In some embodiments, the solid Form $S_C$ of Compound 1 exhibits 16.4% weight loss.

In embodiments, the solid Form $S_C$ of Compound 1 is substantially pure of impurities (e.g., other chemical compounds (i.e., not Compound 1)). In certain embodiments the solid Form $S_C$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $S_C$ of Compound 1 is substantially free of any other solid form of Compound 1. For example, in embodiments, the solid Form $S_C$ of Compound 1 is substantially free of Form A, Form B, Form C, Form D, Form E, Form F, Form $H_A$, Form $H_B$, Form $S_A$, Form $S_B$, Form $S_D$, Form $S_E$, and Form $S_F$. In certain embodiments, the solid Form $S_C$ of Compound 1 comprises less than 15%, less than 10%, or less than 5% by weight of each of Form A, Form B, Form C, Form D, Form E, Form F, Form $H_A$, Form $H_B$, Form $S_A$, Form $S_B$, Form $S_D$, Form $S_E$, and Form $S_F$.

Form $S_D$

In certain embodiments, the invention provides a solid Form $S_D$ of Compound 1. In embodiments, the solid Form $S_D$ of Compound 1 is a non-stoichiometric anisole solvate, with a molar ratio of Compound 1 to 1,4-dioxane of about 1:0.7.

In embodiments, the solid Form $S_D$ of Compound 1 is characterized by high crystallinity.

Figure 25:
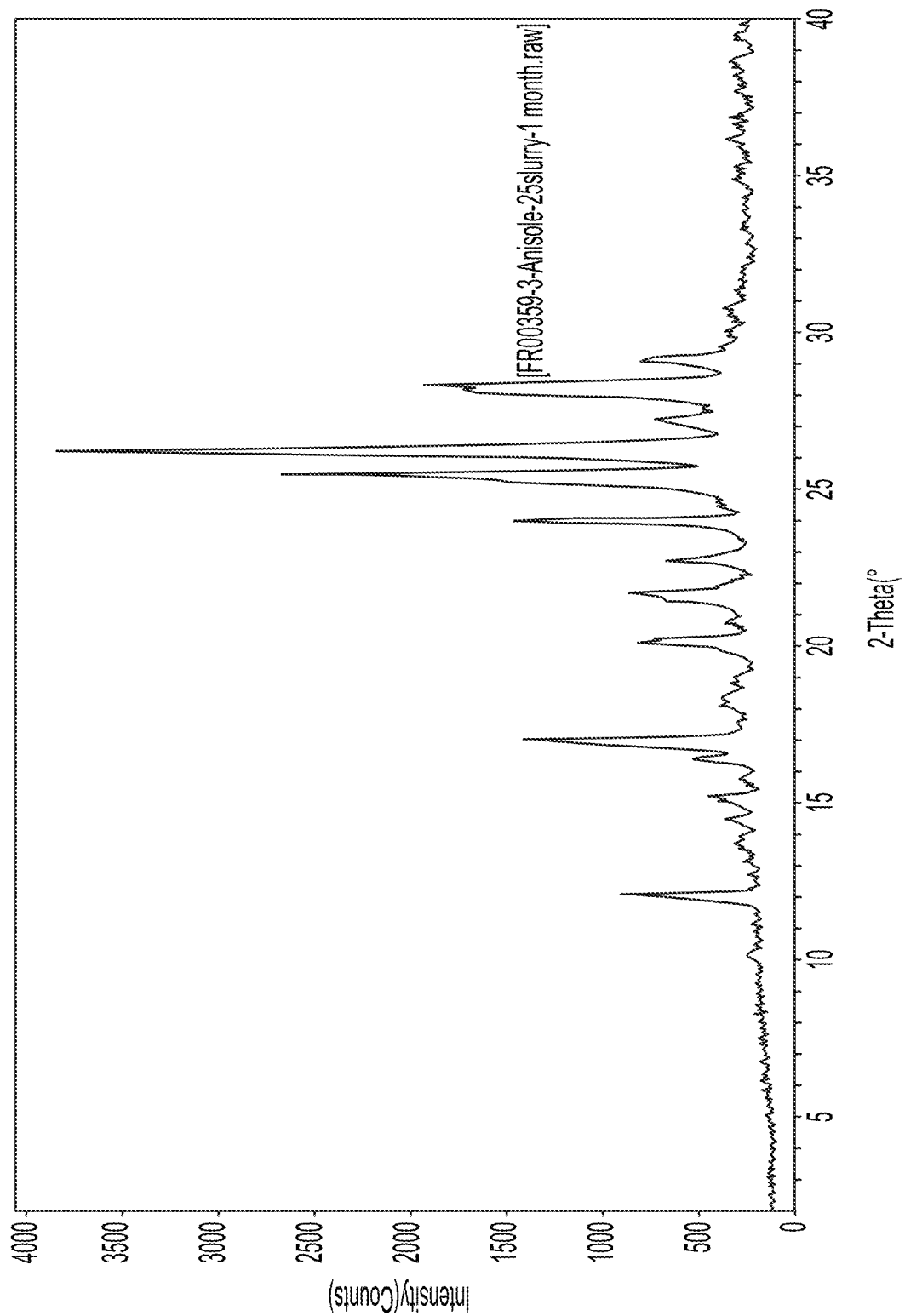
FIG. 25 shows an X-ray powder diffraction (XRPD) analysis of Compound 1, Form $S_D$.

In embodiments, the solid Form $S_D$ of Compound 1 is characterized by an X-ray powder diffraction pattern substantially in accordance with FIG. 25.

In embodiments, the solid Form $S_D$ of Compound 1 is characterized by an X-ray powder diffraction pattern comprising peaks at 17.0, 24.0, 25.5, 26.2 and 28.4±0.2° 2θ.

In embodiments, the solid Form $S_D$ of Compound 1 is characterized by an X-ray powder diffraction pattern comprising peaks at 12.1, 14.5, 25.5, 29.2, and 36.2±0.2° 2θ.

In embodiments, the solid Form $S_D$ of Compound 1 is characterized by an X-ray powder diffraction pattern comprising peaks at 12.1, 17.0, 24.0, 25.5, and 26.2±0.2° 2θ.

In embodiments, the solid Form $S_D$ of Compound 1 is characterized by an X-ray powder diffraction pattern which comprises at least one peak selected from the group consisting of 12.1, 17.0, 12.1, 14.5, 24.0, 25.5, 26.2, 28.4, 29.2, and 36.2±0.2° 2θ.

In embodiments, the solid Form $S_D$ of Compound 1 is characterized by an X-ray powder diffraction pattern which comprises one, two, three, four, and/or five peaks selected from the group consisting of 12.1, 17.0, 12.1, 14.5, 24.0, 25.5, 26.2, 28.4, 29.2, and 36.2±0.2° 2θ.

In embodiments, the solid Form $S_D$ of Compound 1 is characterized by an X-ray powder diffraction pattern comprising one or more peaks expressed in degrees 2θ (±0.2) as listed in Table 9.

TABLE 9

XRPD Data of Solid Form $S_D$ of Compound 1

| Angle 2θ (±0.2) | Relative Intensity (%) |
| --- | --- |
| 10.223 | 2.5 |
| 12.096 | 21.3 |
| 13.138 | 1.9 |
| 13.716 | 3.1 |
| 13.987 | 2.2 |
| 14.466 | 4.5 |
| 15.235 | 7.1 |
| 15.754 | 2.4 |
| 16.4 | 8.7 |
| 17.029 | 34.8 |
| 18.094 | 4 |
| 18.372 | 3.9 |
| 19.04 | 1.8 |
| 20.127 | 16.5 |
| 20.768 | 2.4 |
| 21.704 | 17.5 |
| 21.997 | 3.5 |
| 22.749 | 12.2 |
| 23.994 | 34.5 |
| 25.275 | 33.8 |
| 25.474 | 65.1 |
| 26.223 | 100 |
| 27.247 | 8.4 |
| 28.352 | 44.8 |
| 29.18 | 12.1 |
| 30.809 | 1.9 |
| 33.401 | 1.7 |
| 34.899 | 2.7 |
| 35.276 | 1.9 |
| 36.181 | 3.4 |
| 36.538 | 2.1 |
| 36.87 | 2.4 |
| 37.681 | 2 |
| 38.199 | 2.7 |
| 38.664 | 2.8 |
| 39.495 | 2.4 |

In embodiments, the solid Form $S_D$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, and/or thirty-six peaks expressed in degrees 2θ (±0.2) as listed in Table 9.

In embodiments, the solid Form $S_D$ of Compound 1 is characterized by an X-ray powder diffraction pattern comprising five peaks expressed in degrees 2θ (±0.2) as listed in Table 9.

In embodiments, the solid Form $S_D$ of Compound 1 is characterized by an X-ray powder diffraction pattern comprising ten peaks expressed in degrees 2θ (±0.2) as listed in Table 9.

In embodiments, the solid Form $S_D$ of Compound 1 is characterized by an X-ray powder diffraction pattern comprising fifteen peaks expressed in degrees 2θ (±0.2) as listed in Table 9.

In embodiments, the solid Form $S_D$ of Compound 1 is characterized by an X-ray powder diffraction pattern comprising twenty peaks expressed in degrees 2θ (±0.2) as listed in Table 9.

In embodiments, the solid Form $S_D$ of Compound 1 is characterized by an X-ray powder diffraction pattern comprising twenty-five peaks expressed in degrees 2θ (±0.2) as listed in Table 9.

In embodiments, the solid Form $S_D$ of Compound 1 is characterized by an X-ray powder diffraction pattern comprising thirty peaks expressed in degrees 2θ (±0.2) as listed in Table 9.

In embodiments, the solid Form $S_D$ of Compound 1 is characterized by an X-ray powder diffraction pattern comprising thirty-five peaks expressed in degrees 2θ (±0.2) as listed in Table 9.

In embodiments, the solid Form $S_D$ of Compound 1 is characterized by an X-ray powder diffraction pattern comprising thirty-six peaks expressed in degrees 2θ (±0.2) as listed in Table 9.

Figure 26:
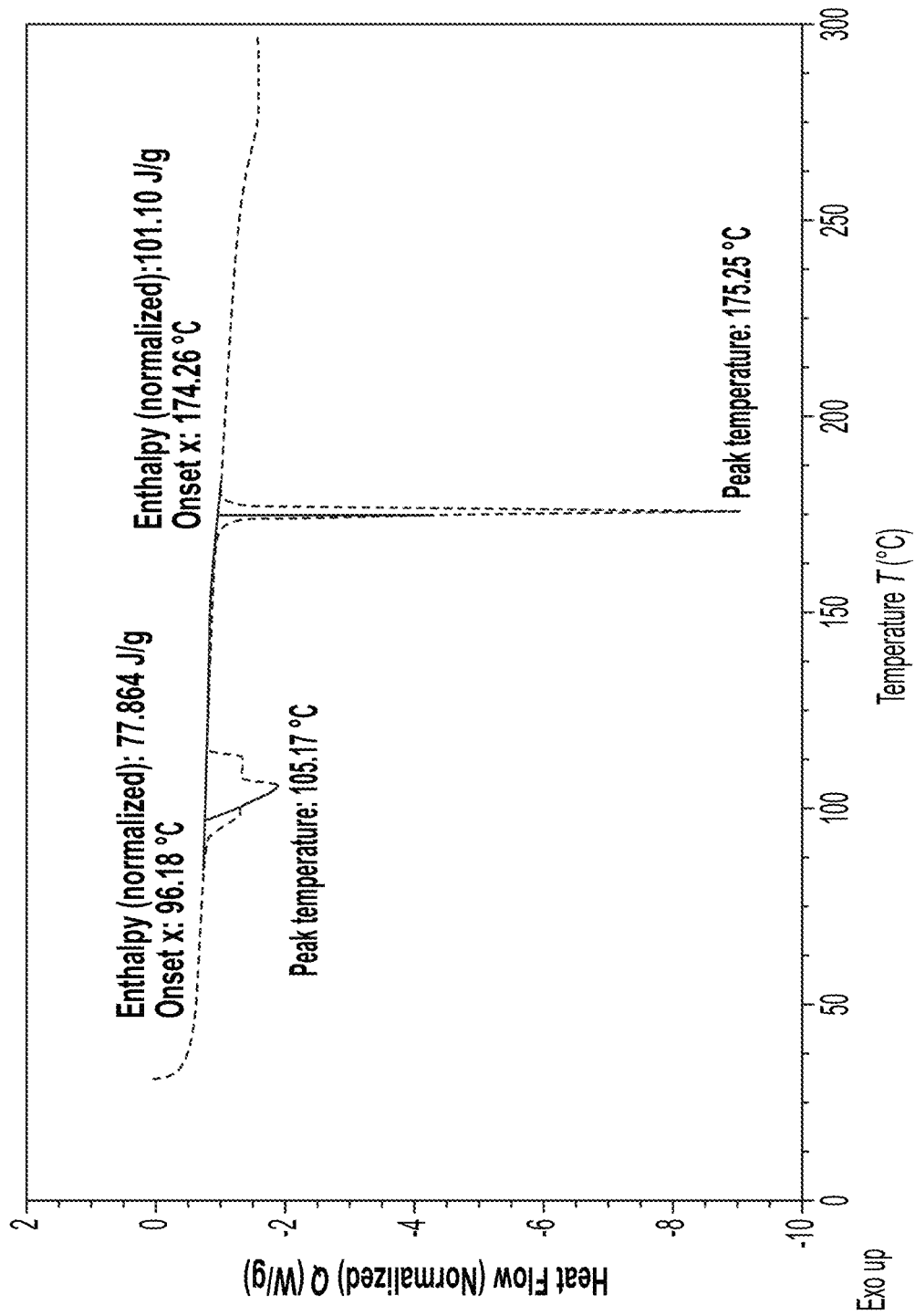
FIG. 26 shows a differential scanning calorimetry (DSC) thermogram of Compound 1, Form $S_D$.

In embodiments, the solid Form $S_D$ of Compound 1 is characterized by a differential scanning calorimetry thermogram having characteristic endotherm peaks at 105.2° C. and 175.3° C. (FIG. 26).

In embodiments, the solid Form $S_D$ of Compound 1 is characterized by a differential scanning calorimetry thermogram having characteristic endotherm onset temperatures at 96.2° C. and 174.3° C. (FIG. 26).

Figure 27:
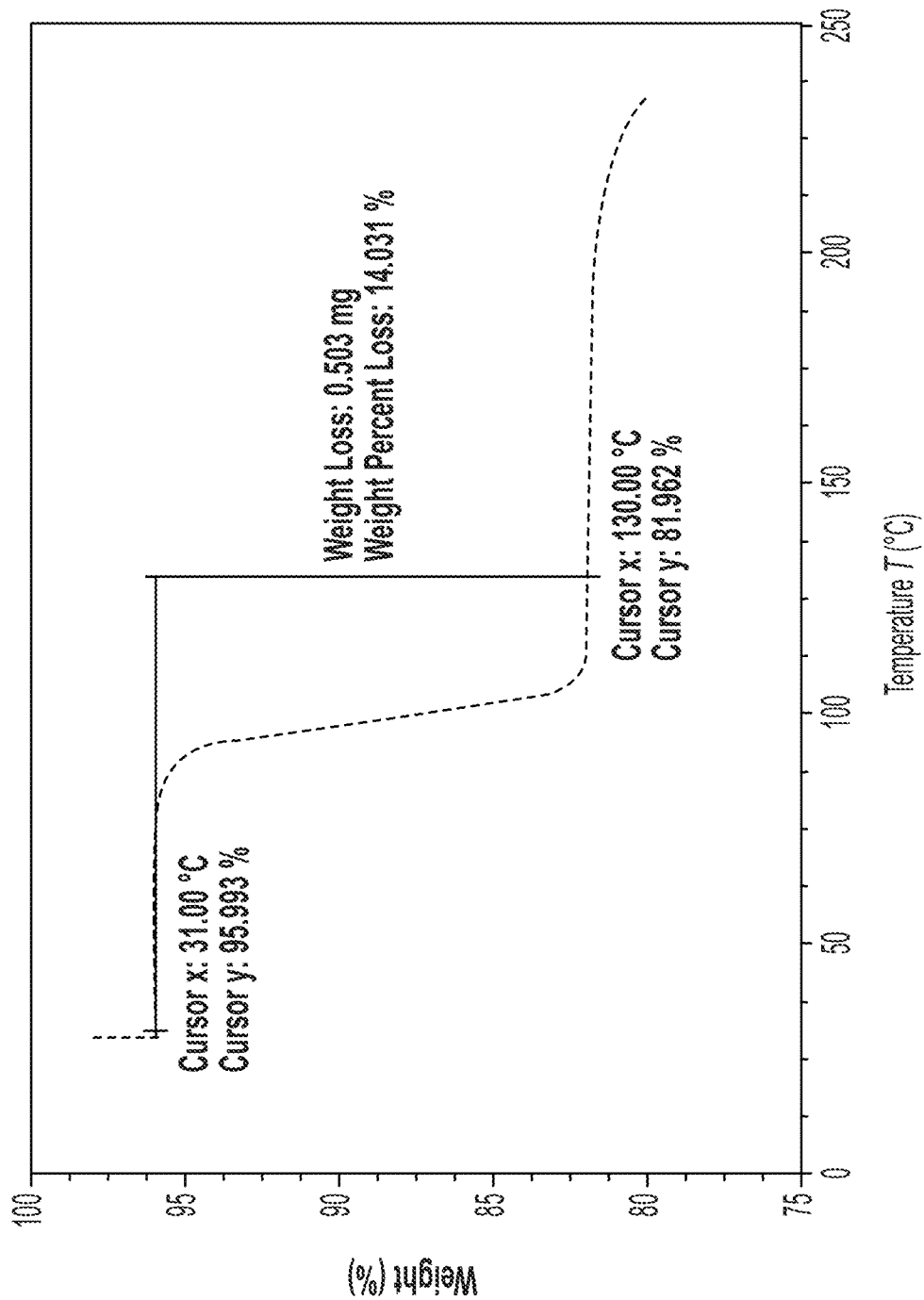
FIG. 27 shows a thermal gravimetric analysis (TGA) thermogram of Compound 1, Form $S_D$.

In embodiments, a representative TGA thermogram of the solid Form $S_D$ of Compound 1 is shown in FIG. 27. In some embodiments, the solid Form $S_D$ of Compound 1 exhibits 14.0% weight loss up to 130° C.

In embodiments, the solid Form $S_D$ of Compound 1 is substantially pure of impurities (e.g., other chemical compounds (i.e., not Compound 1)). In certain embodiments the solid Form $S_D$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $S_D$ of Compound 1 is substantially free of any other solid form of Compound 1. For example, in embodiments, the solid Form $S_D$ of Compound 1 is substantially free of Form A, Form B, Form C, Form D, Form E, Form F, Form $H_A$, Form $H_B$, Form $S_A$, Form $S_B$, Form $S_C$, Form $S_E$, and Form $S_F$. In certain embodiments, the solid Form $S_D$ of Compound 1 comprises less than 15%, less than 10%, or less than 5% by weight of each of Form A, Form B, Form C, Form D, Form E, Form F, Form $H_A$, Form $H_B$, Form $S_A$, Form $S_B$, Form $S_C$, Form $S_E$, and Form $S_F$.

Form $S_E$

In certain embodiments, the invention provides a solid Form $S_E$ of Compound 1. In embodiments, the solid Form $S_E$ of Compound 1 is a non-stoichiometric dimethylacetamide solvate, with a molar ratio of Compound 1 to dimethylacetamide of about 1:2.5.

In embodiments, the solid Form $S_E$ of Compound 1 is characterized by high crystallinity.

Figure 28:
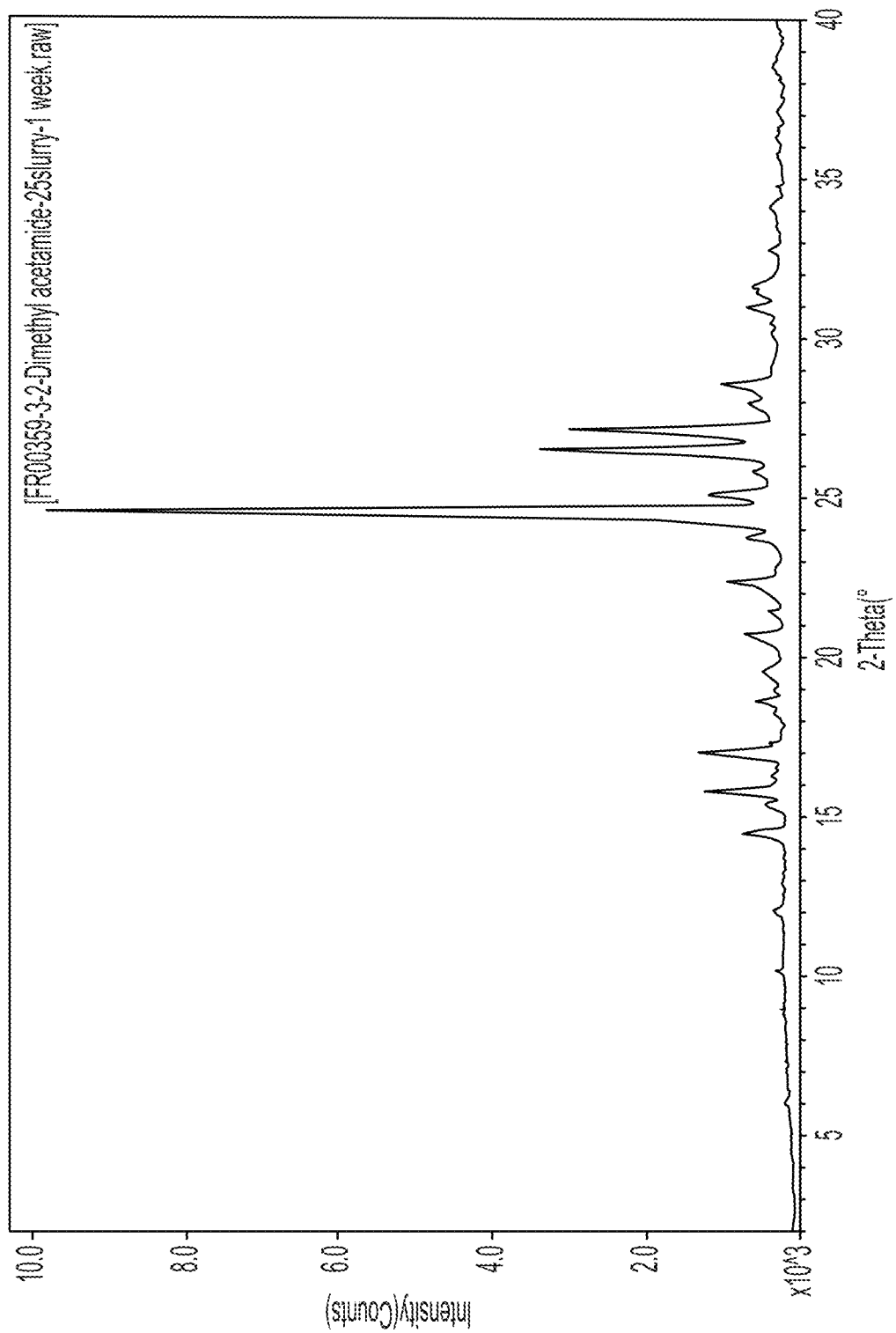
FIG. 28 shows an X-ray powder diffraction (XRPD) analysis of Compound 1, Form $S_E$.

In embodiments, the solid Form $S_E$ of Compound 1 is characterized by an X-ray powder diffraction pattern substantially in accordance with FIG. 28.

In embodiments, the solid Form $S_E$ of Compound 1 is characterized by an X-ray powder diffraction pattern comprising peaks at 15.8, 17.0, 24.6, 26.5, and 27.2±0.2° 2θ.

In embodiments, the solid Form $S_E$ of Compound 1 is characterized by an X-ray powder diffraction pattern comprising peaks at 14.5, 17.0, 25.1, 26.5, and 27.2±0.2° 2θ.

In embodiments, the solid Form $S_E$ of Compound 1 is characterized by an X-ray powder diffraction pattern comprising peaks at 14.5, 15.8, 22.4, 24.6, 26.5, and 27.2±0.2° 2θ.

In embodiments, the solid Form $S_E$ of Compound 1 is characterized by an X-ray powder diffraction pattern which comprises at least one peak selected from the group consisting of 14.5, 15.8, 17.0, 22.4, 24.6, 25.1, 26.5, and 27.2±0.2° 2θ.

In embodiments, the solid Form $S_E$ of Compound 1 is characterized by an X-ray powder diffraction pattern which comprises one, two, three, four, and/or five peaks selected from the group consisting of 14.5, 15.8, 17.0, 22.4, 24.6, 25.1, 26.5, and 27.2±0.2° 2θ.

In embodiments, the solid Form $S_E$ of Compound 1 is characterized by an X-ray powder diffraction pattern comprising one or more peaks expressed in degrees 2θ (±0.2) as listed in Table 10.

TABLE 10

XRPD Data of Solid Form $S_E$ of Compound 1

| Angle 2θ (±0.2) | Relative Intensity (%) |
|---|---|
| 6.046 | 0.6 |
| 10.203 | 1.2 |
| 12.112 | 1.7 |
| 14.486 | 5.9 |
| 15.451 | 2.3 |
| 15.828 | 10.7 |
| 16.332 | 0.9 |
| 17.048 | 11.6 |
| 17.363 | 1.9 |
| 18.232 | 1.2 |
| 18.611 | 3.4 |
| 18.983 | 1.1 |
| 19.572 | 2.9 |
| 20.72 | 5.2 |
| 21.481 | 2 |
| 22.414 | 7.3 |
| 22.808 | 0.6 |
| 23.811 | 2.9 |
| 24.623 | 100 |
| 25.138 | 6.4 |
| 25.828 | 1.9 |
| 26.517 | 31.7 |
| 27.187 | 27 |
| 27.978 | 3.2 |
| 28.57 | 7.3 |
| 30.204 | 0.8 |
| 30.517 | 0.8 |
| 31.03 | 4 |
| 31.43 | 2.7 |
| 31.704 | 3.1 |
| 32.775 | 1.9 |
| 33.457 | 0.6 |
| 34.094 | 1.7 |
| 35.787 | 1 |
| 36.258 | 1 |
| 36.592 | 0.8 |
| 37.166 | 1.1 |
| 38.529 | 1.7 |
| 38.927 | 0.8 |

In embodiments, the solid Form $S_E$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, and/or thirty-nine peaks expressed in degrees 2θ (±0.2) as listed in Table 10.

In embodiments, the solid Form $S_E$ of Compound 1 is characterized by an X-ray powder diffraction pattern comprising five peaks expressed in degrees 2θ (±0.2) as listed in Table 10.

In embodiments, the solid Form $S_E$ of Compound 1 is characterized by an X-ray powder diffraction pattern comprising ten peaks expressed in degrees 2θ (±0.2) as listed in Table 10.

In embodiments, the solid Form $S_E$ of Compound 1 is characterized by an X-ray powder diffraction pattern comprising fifteen peaks expressed in degrees 2θ (±0.2) as listed in Table 10.

In embodiments, the solid Form $S_E$ of Compound 1 is characterized by an X-ray powder diffraction pattern comprising twenty peaks expressed in degrees 2θ (±0.2) as listed in Table 10.

In embodiments, the solid Form $S_E$ of Compound 1 is characterized by an X-ray powder diffraction pattern comprising twenty-five peaks expressed in degrees 2θ (±0.2) as listed in Table 10.

In embodiments, the solid Form $S_E$ of Compound 1 is characterized by an X-ray powder diffraction pattern comprising thirty peaks expressed in degrees 2θ (±0.2) as listed in Table 10.

In embodiments, the solid Form $S_E$ of Compound 1 is characterized by an X-ray powder diffraction pattern comprising thirty-five peaks expressed in degrees 2θ (±0.2) as listed in Table 10.

In embodiments, the solid Form $S_E$ of Compound 1 is characterized by an X-ray powder diffraction pattern comprising thirty-nine peaks expressed in degrees 2θ (±0.2) as listed in Table 10.

Figure 29:
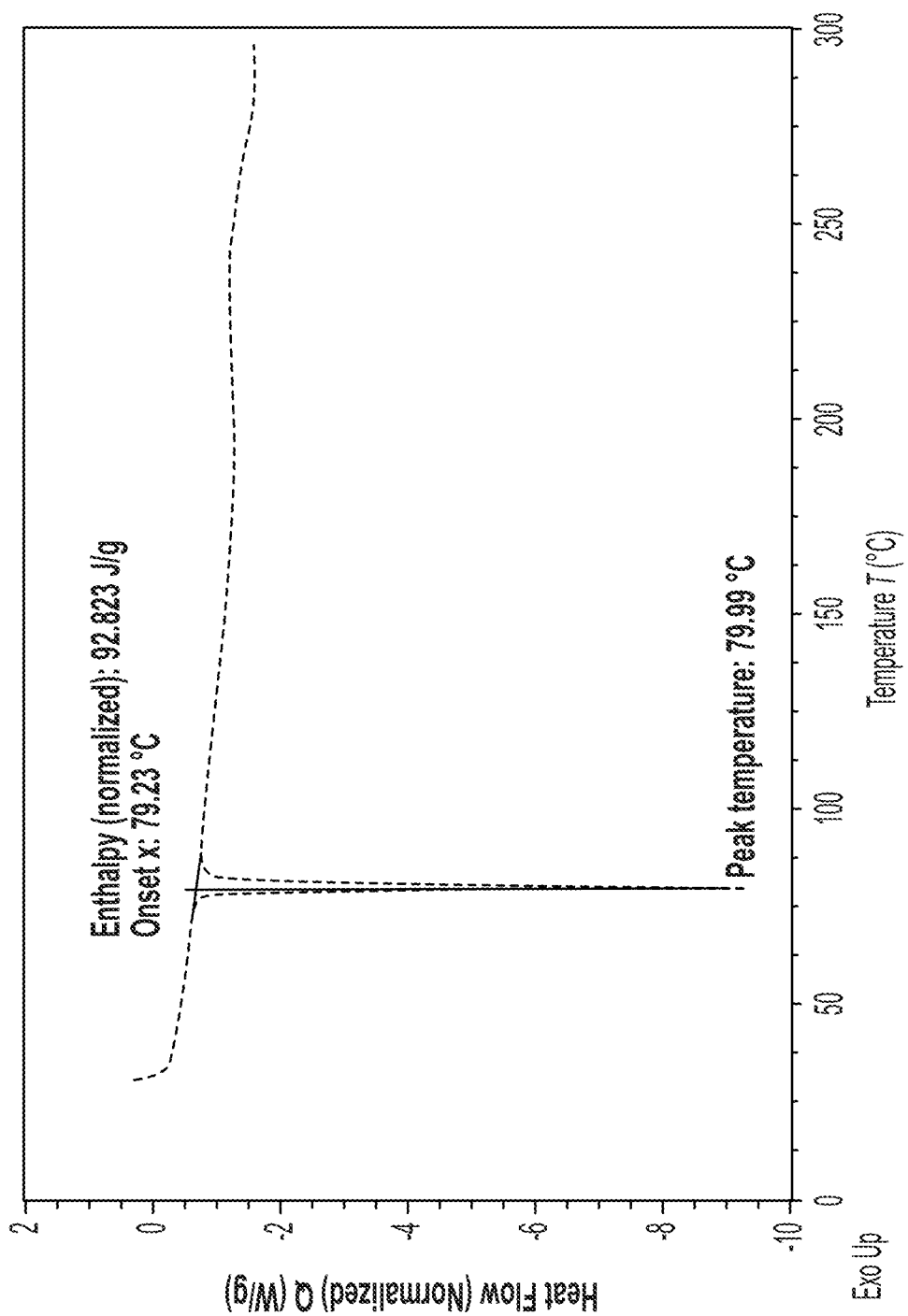
FIG. 29 shows a differential scanning calorimetry (DSC) thermogram of Compound 1, Form $S_E$.

In embodiments, the solid Form $S_E$ of Compound 1 is characterized by a differential scanning calorimetry thermogram having a characteristic endotherm peak at 80.0° C. (FIG. 29).

In embodiments, the solid Form $S_E$ of Compound 1 is characterized by a differential scanning calorimetry thermogram having a characteristic endotherm onset temperature at 79.2° C. (FIG. 29).

Figure 30:
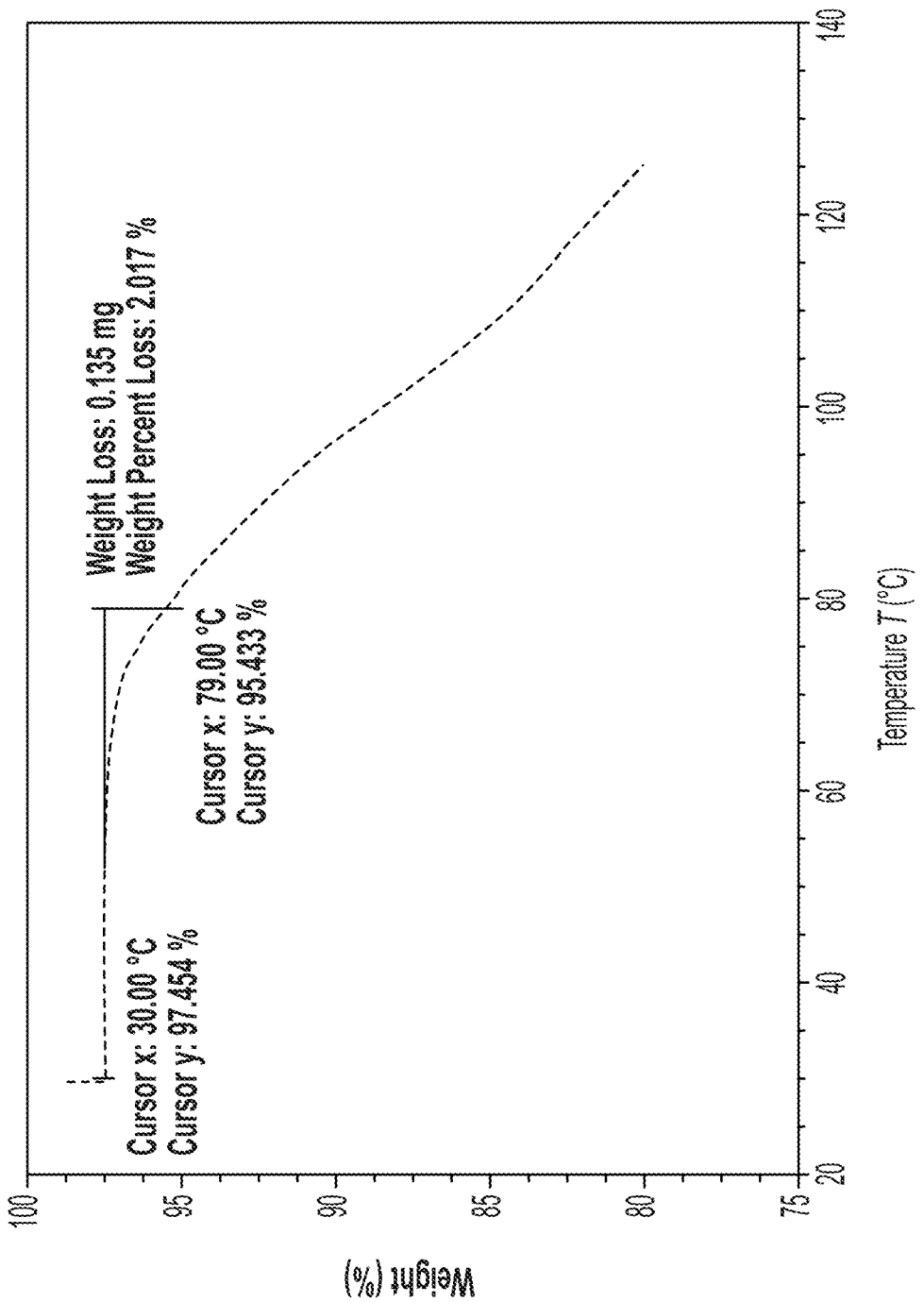
FIG. 30 shows a thermal gravimetric analysis (TGA) thermogram of Compound 1, Form $S_E$.

In embodiments, a representative TGA thermogram of the solid Form $S_E$ of Compound 1 is shown in FIG. 30. In some embodiments, the solid Form $S_E$ of Compound 1 exhibits 2.0% weight loss up to 170° C.

In embodiments, the solid Form $S_E$ of Compound 1 is substantially pure of impurities (e.g., other chemical compounds (i.e., not Compound 1)). In certain embodiments the solid Form $S_E$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $S_E$ of Compound 1 is substantially free of any other solid form of Compound 1. For example, in embodiments, the solid Form $S_E$ of Compound 1 is substantially free of Form A, Form B, Form C, Form D, Form E, Form F, Form $H_A$, Form $H_B$, Form $S_A$, Form $S_B$, Form $S_C$, Form $S_D$, and Form $S_F$. In certain embodiments, the solid Form $S_E$ of Compound 1 comprises less than 15%, less than 10%, or less than 5% by weight of each of Form A, Form B, Form C, Form D, Form E, Form F, Form $H_A$, Form $H_B$, Form $S_A$, Form $S_B$, Form $S_C$, Form $S_D$, and Form $S_F$.

Form $S_F$

In certain embodiments, the invention provides a solid Form $S_F$ of Compound 1. In embodiments, the solid Form $S_F$ of Compound 1 is a non-stoichiometric dimethylacetamide solvate, with a molar ratio of Compound 1 to dimethylacetamide of about 1:1.5.

In embodiments, the solid Form $S_F$ of Compound 1 is characterized by high crystallinity.

Figure 31:
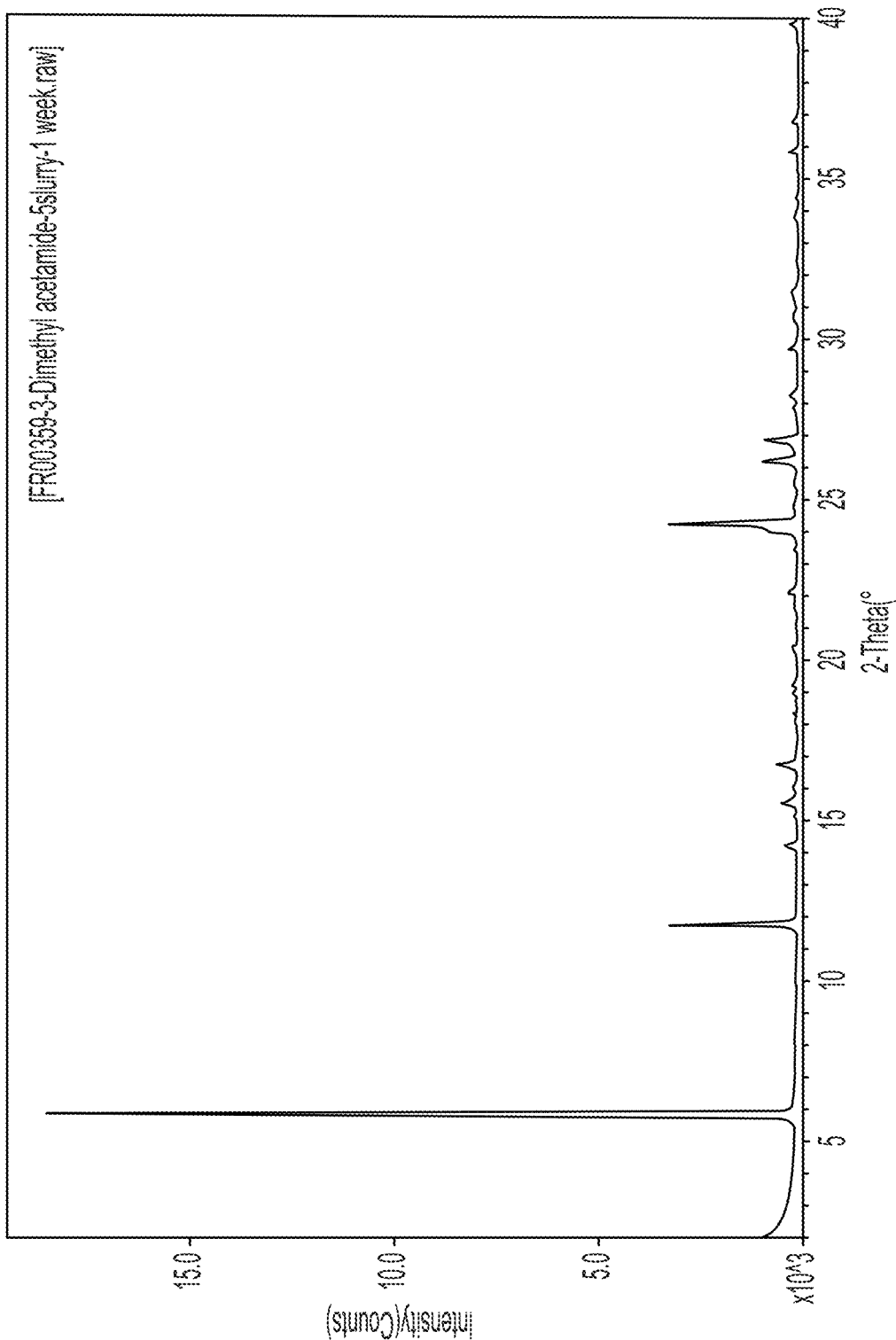
FIG. 31 shows an X-ray powder diffraction (XRPD) analysis of Compound 1, Form $S_F$.

In embodiments, the solid Form $S_F$ of Compound 1 is characterized by an X-ray powder diffraction pattern substantially in accordance with FIG. 31.

In embodiments, the solid Form $S_F$ of Compound 1 is characterized by an X-ray powder diffraction pattern comprising peaks at 5.9, 11.8, 24.1, 24.3, and 26.2±0.2° 2θ.

In embodiments, the solid Form $S_F$ of Compound 1 is characterized by an X-ray powder diffraction pattern comprising peaks at 5.9, 11.8, 16.8, 24.1, and 26.9±0.2° 2θ.

In embodiments, the solid Form $S_F$ of Compound 1 is characterized by an X-ray powder diffraction pattern comprising peaks at 5.9, 11.8, 16.8, 24.3, 26.2, and 26.9±0.2° 2θ.

In embodiments, the solid Form $S_F$ of Compound 1 is characterized by an X-ray powder diffraction pattern which comprises at least one peak selected from the group consisting of 5.9, 11.8, 16.8, 24.1, 24.3, 26.2, and 26.9±0.2° 2θ.

In embodiments, the solid Form $S_F$ of Compound 1 is characterized by an X-ray powder diffraction pattern which comprises one, two, three, four, and/or five peaks selected from the group consisting of 5.9, 11.8, 16.8, 24.1, 24.3, 26.2, and 26.9±0.2° 2θ.

In embodiments, the solid Form $S_F$ of Compound 1 is characterized by an X-ray powder diffraction pattern comprising one or more peaks expressed in degrees 2θ (±0.2) as listed in Table 11.

TABLE 11

XRPD Data of Solid Form $S_F$ of Compound 1

| Angle 2θ (±0.2) | Relative Intensity (%) |
| --- | --- |
| 5.901 | 100 |
| 11.793 | 17.4 |
| 14.25 | 1.8 |
| 15.552 | 2.1 |
| 16.79 | 2.9 |
| 19.257 | 0.8 |
| 20.426 | 0.8 |
| 22.153 | 1.3 |
| 24.091 | 4.4 |
| 24.285 | 17.1 |
| 26.184 | 4.9 |
| 26.89 | 4.4 |
| 28.254 | 1.1 |
| 29.716 | 1.5 |
| 30.625 | 0.6 |
| 31.488 | 1 |
| 33.794 | 0.7 |
| 35.83 | 1.5 |
| 36.791 | 0.9 |

In embodiments, the solid Form $S_F$ of Compound 1 is characterized by an X-ray powder diffraction pattern comprising one, two, three, four, five, six, seven, eight, nine, ten, eleven, twelve, thirteen, fourteen, fifteen, sixteen, seventeen, eighteen, and/or nineteen peaks expressed in degrees 2θ (±0.2) as listed in Table 11.

In embodiments, the solid Form $S_F$ of Compound 1 is characterized by an X-ray powder diffraction pattern comprising five peaks expressed in degrees 2θ (±0.2) as listed in Table 11.

In embodiments, the solid Form $S_F$ of Compound 1 is characterized by an X-ray powder diffraction pattern comprising ten peaks expressed in degrees 2θ (±0.2) as listed in Table 11.

In embodiments, the solid Form $S_F$ of Compound 1 is characterized by an X-ray powder diffraction pattern comprising fifteen peaks expressed in degrees 2θ (±0.2) as listed in Table 11.

In embodiments, the solid Form $S_F$ of Compound 1 is characterized by an X-ray powder diffraction pattern comprising nineteen peaks expressed in degrees 2θ (±0.2) as listed in Table 11.

Figure 32:
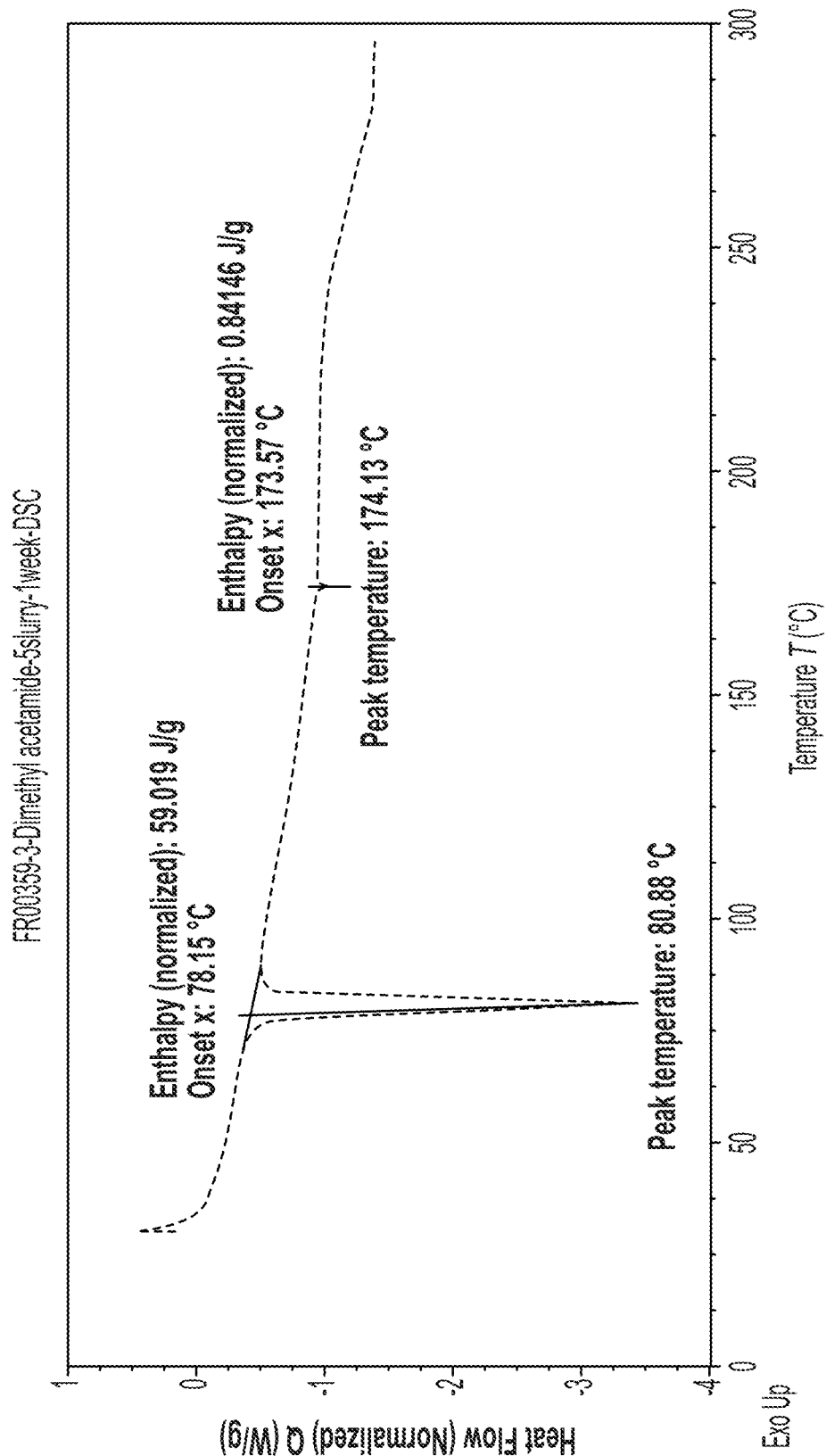
FIG. 32 shows a differential scanning calorimetry (DSC) thermogram of Compound 1, Form $S_F$.

In embodiments, the solid Form $S_F$ of Compound 1 is characterized by a differential scanning calorimetry thermogram having characteristic endotherm peaks at 80.9° C. and 174.1° C. (FIG. 32).

In embodiments, the solid Form $S_F$ of Compound 1 is characterized by a differential scanning calorimetry thermogram having characteristic endotherm onset temperatures at 78.2° C. and 173.6° C. (FIG. 32).

Figure 33:
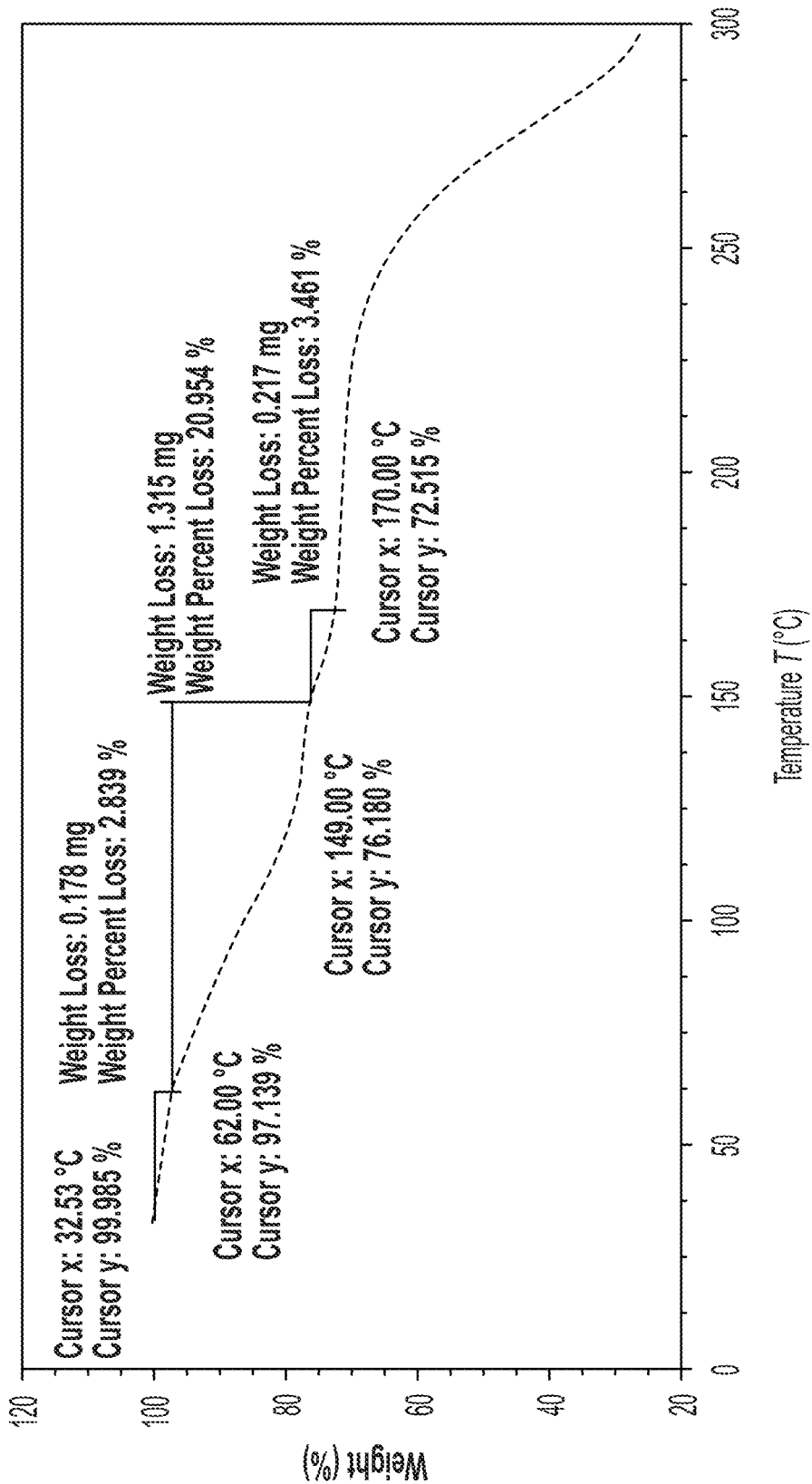
FIG. 33 shows a thermal gravimetric analysis (TGA) thermogram of Compound 1, Form $S_F$.

In embodiments, a representative TGA thermogram of the solid Form $S_F$ of Compound 1 is shown in FIG. 33. In some embodiments, the solid Form $S_F$ of Compound 1 exhibits 27.3% weight loss up to 170° C.

In embodiments, the solid Form $S_F$ of Compound 1 is substantially pure of impurities (e.g., other chemical compounds (i.e., not Compound 1)). In certain embodiments the solid Form $S_F$ of Compound 1 is at least about 99.6% pure, at least about 99.7% pure, at least about 99.8% pure, or at least about 99.9% pure. In certain embodiments, the purity may be determined, e.g., by HPLC.

In embodiments, the solid Form $S_F$ of Compound 1 is substantially free of any other solid form of Compound 1. For example, in embodiments, the solid Form $S_F$ of Compound 1 is substantially free of Form A, Form B, Form C, Form D, Form E, Form F, Form $H_A$, Form $H_B$, Form $S_A$, Form $S_B$, Form $S_C$, Form $S_D$, and Form $S_E$. In certain embodiments, the solid Form $S_F$ of Compound 1 comprises less than 15%, less than 10%, or less than 5% by weight of each of Form A, Form B, Form C, Form D, Form E, Form F, Form $H_A$, Form $H_B$, Form $S_A$, Form $S_B$, Form $S_C$, Form $S_D$, and Form $S_E$.

Methods of Preparing Solid Forms of Compound 1

In embodiments, the solid form of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) may be obtained by subjecting Compound 1

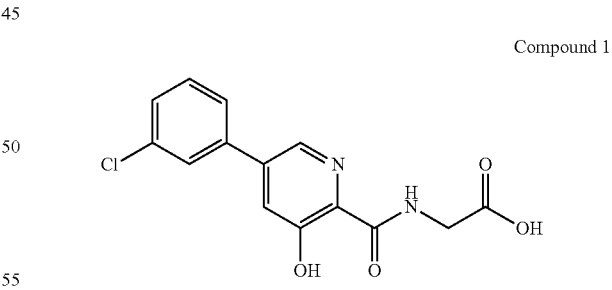

Compound 1 to a procedure comprising
a) preparing a solution of Compound 1 in a proper solvent;
b) bringing the solution to super-saturation to cause formation of solid forms; and
c) isolating the solids.

In embodiments, the solution of Compound 1 is prepared at ambient temperature.

In embodiments, the solution of Compound 1 is prepared at an elevated temperature. In certain embodiments, the solvent is selected from acetone, methyl ethyl ketone, methyl isobutyl ketone, acetonitrile, ethyl acetate, methanol, ethanol, propanol (e.g., isopropanol), n-heptane, n-hexane, petroleum ether, tetrahydrofuran, methyl tethydrofuran (e.g., 2-methyl tetrahydrofuran), dioxane (e.g., 1,4-dioxane), anisole, dimethylformamide (DMF), dimethylacetamide (DMAC), and water, or any combination thereof.

In embodiments, bringing the solution to super-saturation comprises addition of an anti-solvent, allowing the solution to cool, reducing the volume of the solution, solvent exchange, equilibration, or any combination thereof. In certain such embodiments where bringing the solution to super-saturation comprises the addition of anti-solvent, the anti-solvent is water or n-heptane. In certain embodiments where bringing the solution to super-saturation comprises allowing the solution to cool, the solution is allowed to cool to between about 19° C. and about 25° C., or even to between about 0° C. and about 5° C. In certain such embodiments where bringing the solution to super-saturation comprises reducing the volume of the solution, the volume reduction is performed by evaporation.

In embodiments, the process further comprises filtering the solution through a charcoal filter. In certain embodiments, such filtering may be performed after preparing the solution of Compound 1 in a proper solvent. In embodiments, such filtering may be performed prior to bringing the solution to super-saturation.

In embodiments, the solids may be isolated by filtration. In certain such embodiments, the filtration is centrifugal filtration.

In embodiments, the method further comprises drying the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$). In certain such embodiments, the drying is performed at ambient environment. In certain embodiments, the drying is performed at a reduced pressure. In certain embodiments, the drying is performed at an elevated temperature.

In some embodiments, the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) are prepared by slow evaporation.

In some embodiments, the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) are prepared by fast evaporation.

In some embodiments, the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) are prepared by slow cooling.

In some embodiments, the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) are prepared by fast cooling.

In some embodiments, the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) are prepared by equilibration.

In some embodiments, the isolated solid forms of Compound 1 (i.e., Form A, Form B, Form C, Form D, Form E, Form F, Form $H_A$, Form $H_B$, Form $S_A$, Form $S_B$, Form $S_C$, Form $S_D$, Form $S_E$, Form $S_F$) are prepared using an anti-solvent.

Alternative methods for the preparation of any of these solid forms would be apparent to the skilled person on the basis of their common general knowledge and the teaching of the present application.

Formulations (Pharmaceutical Compositions) of Compound 1

In certain embodiments, the solid forms of Compound 1 provided herein (i.e., Form D, Form E, Form F, Form $H_A$, Form $H_B$, Form $S_A$, Form $S_B$, Form $S_C$, Form $S_D$, Form $S_E$, Form $S_F$) may be provided as a formulation (pharmaceutical composition). In embodiments, a formulation is an oral dosage form (e.g., a tablet or capsule).

Exemplary formulations of Compound 1 are described in WO 2014/200773 and WO/2016/161094, which are incorporated by reference in their entirety. Still further exemplary formulations are described herein.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

Excipients

A formulation comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) may comprise one or more excipients.

In certain embodiments, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25 NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Examples of excipients that can be used in formulations described herein include, but are not limited to, insoluble diluents, binders, fillers, disintegrants, glidants, carriers, and lubricants.

In embodiments, formulations comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprise: one or more diluents and/or filler; one or more distintegrants; one or more lubricants; and/or one or more glidants.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methylcellulose, (e.g., Nos. 2208, 2906, 2910), microcrystalline cellulose, and mixtures thereof.

Examples of insoluble diluents and carriers suitable for use in the pharmaceutical compositions and dosage forms provided herein include, but are not limited to, dibasic calcium phosphate and microcrystalline cellulose. Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of diluents/fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, hydroxypropyl methylcellulose (HPMC or hypromellose) (e.g., Methocel E5 Premium LV) and mixtures thereof. In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof. In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate (e.g., Explotab), potato or tapioca starch, other starches, pre-gelatinized starch, other starches, clays, other algins, other celluloses, gums, and mixtures thereof.

Glidants that can be used in pharmaceutical compositions and dosage forms include, but are not limited to fumed silica, magnesium carbonate, magnesium stearate, colloidal silicon dioxide (e.g., Aerosil, Cab-O-Sil), starch and talc.

Lubricants that can be used in pharmaceutical compositions and dosage forms include, but are not limited to, calcium stearate, magnesium stearate (e.g. Hyqual® 5712), mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic colloidal silicon dioxide product sold by Cabot Co. of Boston, Mass.), and mixtures thereof.

In embodiments, formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) can comprise intra-granular components, extra-granular components, and film coating components, wherein the intra-granular components comprise Compound 1, an insoluble diluent or carrier, a disintegrant, and a diluent or filler; wherein the extra-granular components comprise a disintegrant, a glidant, and/or a lubricant; and wherein the film coating components comprise a tablet coating.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) that comprise about 10%, about 15%, about 20%, about 25%, about 30%, about 35%, about 40%, about 45%, about 50%, about 55%, about 60%, about 65%, about 70%, about 75%, about 80%, about 85%, or about 90% by weight of the solid form of Compound 1, wherein the weight is the total weight of all intra-granular and extra-granular components of a tablet.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) that comprise about 5%, about 10%, about 15%, about 20%, about 25%, about 30%, about 35%, about 40%, about 45%, or about 50%, by weight of an insoluble diluent or carrier, wherein the weight is the total weight of all intra-granular and extra-granular components of a tablet.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) that comprise about 1%, about 1.5%, about 2.0%, about 2.5%, about 3%, about 3.5%, about 4%, about 4.5%, about 5.0%, about 5.5%, about 6.0%, about 6.5%, about 7%, about 7.5%, about 8%, about 8.5%, about 9.0%, about 9.5%, or about 10%, by weight of a disintegrant, wherein the weight is the total weight of all intra-granular and extra-granular components of a tablet.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) that comprise about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, by weight of a glidant, wherein the weight is the total weight of all intra-granular and extra-granular components of a tablet.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) that comprise about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, about 0.85%, about 0.9%, about 0.95%, about 1.0%, about 1.05%, about 1.1%, about 1.15%, about 1.2%, about 1.2%, about 1.25%, about 1.3%, about 1.35%, about 1.4%, about 1.45%, or about 1.5%, by weight of a lubricant, wherein the weight is the total weight of all intra-granular and extra-granular components of a tablet.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 50% to about 80% by weight of Compound 1, about 10% to about 40% by weight of an insoluble diluent or carrier, about 1.5% to about 4.5% by weight of a disintegrant, and about 1% to about 5% by weight of a diluent or filler; wherein the extra-granular component comprises about 1.5% to about 4.5% by weight of a disintegrant, about 0.1% to about 0.4% by weight of a glidant, and about 0.15% to about 1.35% by weight of a lubricant; and wherein the film coating component comprises about 1.0% to about 8% by weight of a tablet coating; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 55% to about 75% by weight of Compound 1, about 15% to about 35% by weight of an insoluble diluent or carrier, about 2.0% to about 4.0% by weight of a disintegrant, and about 1.8% to about 3.8% by weight of a diluent or filler; wherein the extra-granular component comprises about 2.0% to about 4.0% by weight of a disintegrant, about 0.15% to about 0.35% by weight of a glidant, and about 0.35% to about 1.15% by weight of a lubricant; and wherein the film coating component comprises about 1.0% to about 8% by weight of a tablet coating; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 60% to about 70% by weight of the solid form of Compound 1, about 20% to about 30% by weight of an insoluble diluent or carrier, about 2.5% to about 3.5% by weight of a disintegrant, and about 2.3% to about 3.3% by weight of a diluent or filler; wherein the extra-granular component comprises about 2.5% to about 3.5% by weight of a disintegrant, about 0.2% to about 0.3% by weight of a glidant, about 0.55% to about 0.95% by weight of a lubricant; and wherein the film coating component comprises about 1.0% to about 8% by weight of a tablet coating; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 65% by weight of the solid form of Compound 1, about 25% by weight of an insoluble diluent or carrier, about 3% by weight of a disintegrant, and about 2.8% by weight of a diluent or filler; wherein the extra-granular component comprises about 3% by weight of a disintegrant, about 0.25% by weight of a glidant, about 0.75% by weight of a lubricant; and wherein the film coating component comprises about 2.0% to about 6.0% by weight of a tablet coating; and wherein the weight is the total weight of all intra-granular and extra-granular components.

In embodiments, formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprise one or more diluents/fillers (e.g., microcrystalline cellulose and/or HPMC (hypromellose)) and a disintegrant (e.g., sodium starch glycolate). In embodiments, a formulation further comprises one or more glidants (e.g., colloidal silicon dioxide and/or magnesium stearate).

In embodiments, formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprise one or more diluents/fillers (e.g., microcrystalline cellulose and/or isomalt), one or more disintegrants (e.g., sodium starch glycolate and/or povidone), and one or more lubricants (e.g., sodium lauryl sulfate). In embodiments, a formulation further comprises one or more glidants (e.g., colloidal silicon dioxide and/or magnesium stearate). In embodiments, a formulation comprises one or more excipients selected from the group consisting of microcrystalline cellulose, sodium starch glycolate, and HPMC (hypromellose). In embodiments, a formulation comprises microcrystalline cellulose, sodium starch glycolate, and HPMC (hypromellose).

In embodiments, the formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprise a film-coating components comprising Opadry®. Opadry® is a commercial film-coating that is a formulated powder blend provided by Colorcon. Opadry® combines polymer, plasticizer and pigment in a dry concentrate. Embodiments of Opadry® useful in the present invention include, but are not limited to, Opadry® I (HPC/HPMC), Opadry® 20A18334, Opadry® II, Opadry® II HP (PVA-PEG), or another suitable Opadry® suspension (such as polyvinyl alcohol, polyethylene glycol, titanium dioxide, and talc, with or without colorants).

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular components comprise a solid form of Compound 1, microcrystalline cellulose, sodium starch glycolate, and hydroxypropyl methylcellulose, wherein the extra-granular components comprise sodium starch glycolate, colloidal silicon dioxide, and magnesium stearate; and wherein the film-coating components comprise Opadry®.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 50% to about 80% by weight of the solid form of Compound 1, about 10% to about 40% by weight of microcrystalline cellulose, about 1.5% to about 4.5% by weight of sodium starch glycolate, and about 1% to about 5% by weight of a hydroxypropyl methylcellulose; wherein the extra-granular component comprises about 1.5% to about 4.5% by weight of a sodium starch glycolate, about 0.1% to about 0.4% by weight of colloidal silicon dioxide, and about 0.15% to about 1.35% by weight of magnesium stearate; wherein the film coating component comprises about 1.0% to about 8% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 55% to about 75% by weight of the solid form of Compound 1, about 15% to about 35% by weight of microcrystalline cellulose, about 2.0% to about 4.0% by weight of sodium starch glycolate, and about 1.8% to about 3.8% by weight of a hydroxypropyl methylcellulose; wherein the extra-granular component comprises about 2.0% to about 4.0% by weight of a sodium starch glycolate, about 0.15% to about 0.35% by weight of colloidal silicon dioxide, and about 0.35% to about 1.15% by weight of magnesium stearate; wherein the film coating component comprises about 1.0% to about 8% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 60% to about 70% by weight of the solid form of Compound 1, about 20% to about 30% by weight of microcrystalline cellulose, about 2.5% to about 3.5% by weight of sodium starch glycolate, and about 2.3% to about 3.3% by weight of a hydroxypropyl methylcellulose; wherein the extra-granular component comprises about 2.5% to about 3.5% by weight of a sodium starch glycolate, about 0.2% to about 0.3% by weight of colloidal silicon dioxide, and about 0.55% to about 0.95% by weight of magnesium stearate; wherein the film coating component comprises about 1.0% to about 8% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 60% by weight of the solid form of Compound 1, about 30% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 65% by weight of the solid form of Compound 1, about 25% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 70% by weight of the solid form of Compound 1, about 20% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 75% by weight of the solid form of Compound 1, about 15% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) comprising intra-granular components, extra-granular components, and film coating components, wherein the intra-granular component comprises about 80% by weight of the solid form of Compound 1, about 10% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Liquid Dosage Forms

Liquid dosage forms of Compound 1, prepared from a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$), for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Amounts of the Solid Form of Compound 1

In certain other embodiments, provided herein are unit dosage forms of Compound 1 that comprise between about 150 mg and about 600 mg of a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$).

In certain other embodiments, provided herein are unit dosage forms of Compound 1 that comprise about 150 mg, 200 mg, 250 mg, 300 mg, 350 mg, 400 mg, 450 mg, 500 mg, 550 mg, or even 600 mg of a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$). In certain embodiments, the unit dosage form comprises about 150 mg, about 185 mg, about 200 mg, about 250 mg, about 300 mg, or even about 315 mg of a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$). In certain such embodiments, the unit dosage form is a capsule comprising about 185 mg, about 200 mg, about 200, about 250 mg, or even about 300 mg of the solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$).

In embodiments, a unit dosage form comprises about 150 mg of a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$). In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate.

In embodiments, a unit dosage form comprises about 300 mg of a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$). In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate.

Diseases Associated with HIF

The solid forms of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$), and pharmaceutical compositions thereof, described herein are useful in therapy, in particular in the therapeutic treatment of disease associated with HIF prolyl hydroxylase modulation.

Diseases associated with HIF prolyl hydroxylase modulation include Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Buerger's disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-vasculitis disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes.

The present disclosure provides herein methods for treating or preventing a disease or disorder ameliorated by modulation of HIF prolyl hydroxylase comprising administering to a subject having a disease ameliorated by modulation of HIF prolyl hydroxylase an effective amount of Compound 1, namely a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$), or a pharmaceutical composition thereof.

Specifically, the methods provided herein include administering a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$), or a pharmaceutical composition thereof, to a subject having, inter alia, Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Buerger's disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-vasculitis disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes.

In certain embodiments, the methods provided herein include administering a solid form of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$), or a pharmaceutical composition thereof, to a subject having anemia, as such anemia secondary to non-dialysis dependent chronic kidney disease.

In embodiments, a subject has anemia secondary to or associated with chronic kidney disease (renal anemia).

In certain embodiments, the chronic kidney disease is stage 3, 4, or 5 chronic kidney disease. In certain embodiments, the chronic kidney disease is pre-dialysis chronic kidney disease. In other embodiments, the chronic kidney disease is non-dialysis dependent chronic kidney disease. In still other embodiments, the subject has not been previously treated for anemia, such as anemia secondary to chronic kidney disease. In alternative embodiments, the subject has been previously treated for anemia, such as anemia secondary to chronic kidney disease. In some embodiments, the patient is refractory to treatment with recombinant erythropoietin.

Doses and Dosing Regimens of Compound 1

The specific doses of a solid forms of Compound 1 (i.e., one of Form D, Form E, Form F, Form $H_A$, Form $H_B$, Form $S_A$, Form $S_B$, Form $S_C$, Form $S_D$, Form $S_E$, or Form $S_F$) can be administered in any manner known to the skilled artisan. Exemplary doses are provided herein.

Such doses may be taken orally, topically, or intravenously. Doses may be taken while fasting, together with fluids, or together with food of any kind. In embodiments, doses may be taken or 1, 2, 3, 4, 5, 6, 7, 8, 9, 10, 11, or 12 hours after a meal, or 1, 2, 3, 4, 5, 6, 7, 8, 9, 10, 11, or 12 hours before a meal. Doses may be taken at any time of day. In certain embodiments, repeat doses are administered at the same time during the day. In certain embodiments, the dose doses are administered in the morning, around mid-day, or in the evening. In certain embodiments, the doses are administered between 4.00 am and 2.00 pm. In certain embodiments, the doses are administered between 5.00 am and 1.00 pm. In certain embodiments, the doses are administered between 6.00 am and 12.00 noon. In certain embodiments, the doses are administered between 7.00 am and 11.00 am. In certain embodiments, the doses are administered between 8.00 am and 10.00 am. In certain embodiments, the doses are administered before, during, or after breakfast. Administration and dosing regimens may be adjusted as described herein.

In a specific embodiment, a subject is initially treated with 3 tablets of 150 mg of Compound 1 daily (450 mg/day). Dose levels of the compound include 150, 300, 450, and 600 mg. Thereafter, the medication is taken once daily during the course of treatment. The subject should take the study medication with 4 ounces of water or other oral beverage, regardless of food intake. The dose is taken at approximately the same time each day, preferably between 7 AM and 2 PM.

This section provides several exemplary doses for Compound 1. In certain embodiments, such a dose is the initial dose at the beginning of a treatment. In other embodiments, such a dose is the adjusted dose at a later time during the course of treatment.

In certain embodiments, the daily dose of Compound 1 is between about 150 mg and about 600 mg. In certain embodiments, the daily dose of the compound is between about 150 mg and about 300 mg or about 300 and about 600 mg, or between about 600 mg and about 750 mg. In certain embodiments, the daily dose is about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, or even about 1200 mg of Compound 1, or a pharmaceutically acceptable salt thereof. In certain embodiments, the daily dose of Compound 1, or a pharmaceutically acceptable salt thereof, is at least about 150 mg, at least about 300 mg, at least about 450 mg, or even at least about 600 mg.

In certain embodiments, the daily dose is about 150 mg, about 300 mg, about 450 mg, about 600 mg, or about 750 mg of Compound 1. In certain embodiments, the daily dose Compound 1, is about 150 mg, about 300 mg, about 450 mg, or about 600 mg. In certain embodiments, the daily dose is about 240 mg, about 370 mg, about 500 mg, or about 630 mg of Compound 1.

In certain embodiments, a daily dose of 450 mg of Compound 1 may be decreased by about 150 mg, such that the daily dose of the compound is about 300 mg. In certain embodiments, a daily dose of Compound 1 may be decreased by about 300 mg, such that the daily dose of the compound is about 150 mg. In certain embodiments, the daily dose Compound 1 may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose of Compound 1, or a pharmaceutically acceptable salt thereof, may be increased or decreased by an amount between about 75 mg and about 250 mg, about 100 mg and about 225 mg, or about 125 mg and about 200 mg. In certain such embodiments, the daily dose Compound 1 does not exceed about 600 mg.

EXEMPLIFICATION

Analytical Procedures

Step-by-step sample preparation and analysis protocols for XRPD, TGA, DSC, DVS, NMR, SEM, PLM, FT-IR, and HPLC analyses are provided in Table 12.

TABLE 12

Step Sample Preparation and Analysis Protocols for Analytical Methods

| Technique | Step-by-step sample preparation and analysis protocol | | | |
|---|---|---|---|---|
| XRPD | Sample preparation: About 10 mg powder was spread on the monocrystalline silicon board and detected by XRPD. Analysis protocol: | | | |
| | Instrument | Bruker D8 Advance X-Ray Diffractometer | | |
| | Tube | Cu/K-Alpha1 ($\lambda$ = 1.54060 Å) | Voltage(KV) | 40 |
| | Current(mA) | 40 | Divergence Slit(mm) | 0.6 |
| | Primary Soller Slit(deg) | 2.5 | Secondary Soller Slit(deg) | 2.5 |
| | Detector | PSD: LynxEye | PSD electronic window(deg) | 3.0 |
| | Scan Ttype | Locked Coupled | Scan Mode | Continuous |
| | Scan Axis | 2-Theta | Scan Scope (deg) | 2-40 |
| | Step Size | 0.02 | No. of Steps | 1824 |
| | Time/Step(s) | 0.45 | | |
| | Sample Rotation | On | Rotation Speed(rpm) | 15 |
| TGA | Sample preparation: Samples of about 1~10 mg were placed in an open 100 µL aluminium pan and characterized by TGA. Analysis protocol: | | | |
| | Instrument | TA Q5000 & Discovery TGA 5500 | | |
| | Material amount | 1-10 mg | | |
| | Reacting Gas | N2 25 mL/min | Protective Gas | N2 10 mL/min |
| | Data Sampling Interval | 0.50 s/pt | Pan Type | Platinum 100 µL, open |
| | Temperature Program | Abort next seg if weight % <80.00% (w/w) or ambient condition to 300° C.; Ramp 10° C./min | | |
| DSC | Sample preparation: Accurate amount (0.5~2 mg) sample was added into a curled aluminum sample pan. Close the sample pan with a holed cover. Analysis protocol: Instrument: TA DSC Q2000 & Discovery DSC-2500 Initial temperature: 30° C. or room temperature. Heating rate: 10° C./min; Final temperature: 300° C. Nitrogen flow: 50 mL/min. | | | |

TABLE 12-continued

Step Sample Preparation and Analysis Protocols for Analytical Methods

| Technique | Step-by-step sample preparation and analysis protocol | |
|---|---|---|
| DVS | Sample preparation: Around 5-20 mg of sample was weighed to test its moisture sorption/desorption profiles. Analysis protocol: | |
| | Instrument | SMS Advantage-1 Dynamic Vapour Sorption Advantage System & SMS Advantage-1 Dynamic Vapour Sorption Advantage System |
| | Total gas flow | 200 sccm |
| | Oven temperature | 25° C. |
| | Solvent | Water |
| | Control Mode | Open loop |
| | Method Preheat | N/A |
| | Stage method | Stage type: dm/dt = 0.002 Cycle: 40-0-95-0-40 RH Stage Step: 10% Equilibrium: 0.01 dm/dt (%/min) Minimum DMDT stability duration: 1 h. Maximum DMDT stage time: 360 min. Sampling rate: 1 min. Save data rate: 1 min. |
| NMR | Sample preparation: Transfer about 5 mg compound into NMR tube and dissolved the sample with deuterated DMSO. Analysis protocol: | |
| | Instrument | Bruker Advance II 400 MHZ |
| | Probe | 5 mm PABBO BB-1H/D Z-GRD Z108618/0226 |
| | Temperature | 297.6K |
| | Relaxation delay | 1 second |
| SEM | Sample preparation: Attach a copper conductive adhesive to a bare sample stub. Transfer sample firmly against the conductive adhesive. And then tie the sample on aluminum stand. Tap the stub and spray the surface of sample on the aluminum stand to remove loose particles with a can of comprised air. Put samples in sample holder and insert sample holder into SEM and observe the vertical section. For SEM test, capture clear images by adjusting focus, brightness, contrast and magnification. Analysis protocol: | |
| | Instrument | Phenom Prox SEM-EDS |
| | Parameters | SEM |
| | Detector | BSD Full |
| | Magnification | 300x-10000x |
| | Voltage | 5 kV |
| | Current | Point |
| PLM | Sample preparation: Approximate 1 mg samples were dispersed in silicon oil on a glass slide without cover slip and observed. Analysis protocol: Instrument: Nikon LV100POL Polarized Light Microscope Sample was dispersed in silicon oil on a glass slide without cover slip and observed. The polarized light microscopy image was captured using ocular lens (10X) and physical lens (5X/10X/20X/50X) under crossed polarizers. | |
| FT-IR | Sample preparation: About 1 mg sample was spread in the groove, and rotate the pressure control ring until the sample was pressed firmly. Analysis protocol: | |
| | Instrument | Fourier Transform Infrared Spectroscopy (Nicolet 6700, Thermo Scientific) |
| | No. of sample scans | 32 |
| | No. of background | 32 |
| | Resolution | 4 |
| | Wavelength range | 4000 to 525 cm−1 |
| | Baseline correction | Yes |
| | Optical velocity | 0.4747 |
| | Aperture | 150 |
| | Window | Diamond |
| HPLC | Sample preparation: Accurate amount (~1 mg) sample was weighed into 8 mL or 40 mL vials. Then 4 mL dilution solvent was added into the vial and under ultrasonic for about 5 minutes to obtain clear solution. 1 mL clear solution was pipetted into 2 mL glass vials and tested by HPLC. Analysis protocol: | |
| | Instrument | High performance liquid chromatography (Shimadzu, Model: LC-20ADXR) |
| | Column | Zorbax SB-C18 150 × 4.6 mm 3.5 μm |
| | Column | 30° C. |
| | Buffer | 0.1% TFA, 0.1% TEA in water pH adjusted with phosphoric acid |

TABLE 12-continued

Step Sample Preparation and Analysis Protocols for Analytical Methods

| Technique | Step-by-step sample preparation and analysis protocol | | |
|---|---|---|---|
| Mobile Phase A | 650 mL Buffer, 350 mL Acetonitrile | | |
| Mobile Phase B | 50 mL Buffer, 950 mL Acetonitrile | | |
| Gradient | Time [min] | % A | % B |
|  | 0 | 100 | 0 |
|  | 9 | 0 | 100 |
|  | 12 | 0 | 100 |
|  | 12.1 | 100 | 0 |
|  | 18 | 100 | 0 |
| Flow rate | 1 mL/min | | |
| Injection Volume | 5 μL | | |
| Detector | UV 263 nm | | |
| Dilution Solvent | Acetonitrile | | |
| Dilution | 0.25 mg/mL | | |

Example 1: Preparation of Compound 1

Compound 1 may be synthesized or obtained according to any method apparent to those of skill in the art. Compound 1 may also be prepared according to the methods described in U.S. Pat. No. 7,811,595, filed Jun. 26, 2007 and U.S. Pat. No. 9,145,366, filed in Jun. 5, 2012, which are incorporated herein by reference in their entireties.

Example 2: Preparation of Solid Forms A-C

Exemplary methods of preparing solid Forms A, B, and C have been disclosed in International Publication No. WO 2015/073779. Alternative methods for preparing solid Forms A, B, and C are disclosed in Examples 3-5 herein.

Example 3: Alternative Preparation of Solid Form A

Ultra-pure form of Compound 1 was re-crystallized in a 2-MeTHF/n-heptane solvent system.

Example 4: Alternative Preparation of Solid Form B

Slow Evaporation Method

About 10 mg of Compound 1 was weighed into a 2 mL vial, followed by addition of 1 mL acetonitrile. The resulting suspension was equilibrated at room temperature for about 1 hour. The liquid phase was isolated by centrifugal filtration at 14000 rpm for 5 minutes. The liquid phase was then transferred into a 2 mL glass vial wrapped with an aluminum foil with pin holes on top. The solution was allowed to evaporate slowly at room temperature. After 6 days, a white solid was obtained.

Fast Cooling Method

About 100 mg of Compound 1 was weighed into a 2 mL vial, followed by addition of 0.7 mL acetonitrile. The resulting suspension was equilibrated at 60° C. for about 1 hour. The liquid phase was isolated by centrifugal filtration at 14000 rpm for 30 seconds. The liquid phase was transferred into a 2 mL glass vial and immediately placed into a 0° C. ice bath. After agitation by magnetic stirring for about 1 hour, the clear solution turned into a suspension. The solid phase was isolated by centrifugal filtration at 14000 rpm for 5 minutes as a white solid.

Example 5: Alternative Preparation of Solid Form C

Fast Evaporation Method

From Tetrahydrofuran

To 3.0 g of Compound 1 in a 40 mL glass vial was added 10 mL THF at room temperature. After magnetic stirring for 10 min, a clear solution was obtained. The solution was filtered by syringe membrane and transferred into a 40 mL glass vial. The solution was then blown by nitrogen gas from top for about 1 hour without stirring. An off-white solid was obtained.

From Ethyl Acetate

To 3.0 g of Compound 1 in a 40 mL glass vial was added 10 mL ethyl acetate at room temperature. After magnetic stirring for 10 min, a clear solution was obtained. The solution was filtered by syringe membrane and transferred into a 40 mL glass vial. The solution was then blown by nitrogen gas from top for about 1 hour without stirring. An off-white solid was obtained.

From 2-Methyl Tetrahydrofuran

To 3.0 g of Compound 1 in a 40 mL glass vial was added 10 mL 2-MeTHF at room temperature. After magnetic stirring for 10 min, a clear solution was obtained. The solution was filtered by syringe membrane and transferred into a 40 mL glass vial. The solution was then blown by nitrogen gas from top for about 1 hour without stirring. An off-white solid was obtained.

From 2-Methyl Tetrahydrofuran/Heptane

To 3.0 g of Compound 1 in a 40 mL glass vial was added 10 mL 2-MeTHF/heptane (50:50 v/v) at room temperature. After magnetic stirring for 10 min, a clear solution was obtained. The solution was filtered by syringe membrane and transferred into a 40 mL glass vial. The solution was then blown by nitrogen gas from top for about 1 hour without stirring. An off-white solid was obtained.

From Tetrahydrofuran/Water

To 3.0 g of Compound 1 in a 40 mL glass vial was added 10 mL THF/$H_2O$ (50:50 v/v) at room temperature. After magnetic stirring for 10 min, a clear solution was obtained. The solution was filtered by syringe membrane and transferred into a 40 mL glass vial. The solution was then blown by nitrogen gas from top for about 1 hour without stirring. An off-white solid was obtained.

Example 6: Preparation of Solid Form D

Fast Cooling Method

To about 100 mg Compound 1 in a 2 mL glass vial was added 0.7 mL MeOH/$H_2O$ (80:20 v/v). Resulting suspension was equilibrated at 60° C. for about 1 hour. The liquid phase was isolated by centrifugal filtration at 14000 rpm for 30 seconds. The liquid phase was transferred into a 2 mL glass vial and immediately placed into a 0° C. ice bath. After agitation by magnetic stirring for about 1 hour, the clear solution turned into a suspension. The solid phase was isolated by centrifugal filtration at 14000 rpm for 5 minutes as a white solid.

Slow Cooling Method

To about 100 mg Compound 1 in a 2 mL glass vial was added 0.7 mL MeOH. The resulting suspension was equilibrated at 60° C. for about 1 hour. The liquid phase was isolated by centrifugal filtration at 14000 rpm for 30 seconds. The liquid phase was transferred into a 2 mL glass vial and slowly cooled from 60° C. to 0° C. at 0.1° C./min. A white solid precipitated out during the cooling. The white solid was isolated by centrifugal filtration at 14000 rpm for 5 minutes.

Example 7: Preparation of Solid Form E

Slow Evaporation Method

To 500 mg of Compound 1 in a 2 mL glass vial was added 1.5 mL TH F. After stirring for about 1 hour at room temperature, a clear solution was obtained and subjected to centrifugal filtration at 14000 rpm for 5 minutes. The clear solution was then transferred in to a 2 mL glass vial wrapped with an aluminum foil with pin holes on top. The solution was then allowed to evaporate slowly at room temperature. After 4 days, a white solid was obtained.

Fast Evaporation Method

To 90 mg of Compound 1 in a 2 mL glass vial was added 0.7 mL MEK at room temperature. After magnetic stirring for 10 min, suspension was obtained. The suspension was filtered by syringe membrane and transferred into a 2 mL glass vial. Then solution was blown by nitrogen gas from top for about 30 minutes without stirring. A white solid was obtained.

Example 8: Preparation of Solid Form F

Fast Cooling Method

To about 100 mg of Compound 1 in a 2 mL glass vial was added 0.7 mL EtOH/$H_2O$ (95:5 v/v). The resulting suspension was stirred at 60° C. for about 1 hour. The liquid phase was isolated by centrifugal filtration at 14000 rpm for 30 seconds. The liquid phase was then transferred into a 2 mL glass vial and immediately placed into a 0° C. ice bath. After agitation by magnetic stirring for about 1 hour, the clear solution turned into a suspension. The solid phase was isolated by centrifugal filtration at 14000 rpm for 5 minutes as a white solid.

Example 9: Preparation of Solid Form $H_A$

Equilibrium Method

To 2.0 g of Compound 1 in a 40 mL glass vial was added 6 mL THF/$H_2O$ (50:50 v/v). The resulting suspension was stirred at 5° C. for 7 days. The solid phase was isolated by centrifugal filtration at 14000 rpm for 5 minutes as a white solid.

Anti-Solvent Method

To 300 mg of Compound 1 in a 2 mL glass vial was added 0.5 mL 2-MeTHF. The resulting suspension was equilibrated at room temperature for 10 min and filtered by a syringe membrane to isolate liquid phase. To the clear solution was added slowly about 2 mL of n-heptane under stirring and then stirred for 7 days. The clear solution so obtained was placed in the fume hood for 35 days. Solid phase was isolated by centrifugal filtration at 14000 rpm for 5 minutes as a white solid.

Example 10: Preparation of Solid Form $H_B$

Equilibrium Method

To about 100 mg of Compound 1 in a 2 mL glass vial was added 0.3 mL of 1,4-dioxane at 25° C. The resulting suspension was stirred at 25° C. for 7 days. The solid phase was isolated by centrifugal filtration at 14000 rpm for 5 minutes as a white solid.

Example 11: Preparation of Solid Form $S_A$

Equilibrium Method

To about 100 mg of Compound 1 in a 2 mL glass vial was added 0.3 mL of 1,4-dioxane at 25° C. The resulting suspension was stirred at 25° C. for 7 days. The solid phase was isolated by centrifugal filtration at 14000 rpm for 5 minutes as a white solid.

Example 12: Preparation of Solid Form $S_B$

Anti-Solvent Method

To 500 mg of Compound 1 in a 4 mL glass vial was added 1.8 mL of 1,4-dioxane. The resulting suspension was equilibrated at room temperature for 10 min and filtered by a syringe membrane to isolate liquid phase. To the clear solution was slowly added 4 mL heptane under vigorous stirring and the solution became into a suspension. After centrifugal filtration at 14000 rpm for 5 minutes, a white solid was obtained.

Example 13: Preparation of Solid Form $S_C$

Slow Cooling Method

To about 400 mg of Compound 1 in 2 mL glass vial was added 0.2 mL of 1,4-dioxane. The resulting suspension was equilibrated at 60° C. for about 1 hour. The liquid phase was isolated by centrifugal filtration at 14000 rpm for 30 seconds. The liquid phase was transferred into a 2 mL glass vial and slowly cooled from 60° C. to 0° C. at 0.1° C./min. A white solid precipitated out during the cooling. The white solid was isolated by centrifugal filtration at 14000 rpm for 5 minutes.

Example 14: Preparation of Solid Form $S_D$

Slow Equilibration Method

To 100 mg of Compound 1 in a 2 mL glass vial was added 1.0 mL of anisole. The resulting suspension was stirred at 25° C. for 1 month, followed by centrifugal filtration at 14000 rpm for 5 minutes. A white solid was obtained.

Fast Equilibration Method

To 100 mg of Compound 1 in a 2 mL glass vial was added 1.0 mL of anisole. The resulting suspension was stirred at 5° C. for 7 days, followed by centrifugal filtration at 14000 rpm for 5 minutes. A white solid was obtained.

Example 15: Preparation of Solid Form $S_E$

Equilibration Method

To about 400 mg of Compound 1 in a 2 mL glass vial was added 0.4 mL of dimethyl acetamide. The resulting suspension was stirred at 25° C. for 1 month, followed by centrifugal filtration at 14000 rpm for 5 minutes. A white solid was obtained.

Example 16: Preparation of Solid Form $S_F$

Equilibration Method

To about 200 mg of Compound 1 in a 2 mL glass vial was added 0.3 mL of dimethyl acetamide. The resulting suspension was stirred at 5° C. for 7 days, followed by centrifugal filtration at 14000 rpm for 5 minutes. A white solid was obtained.

While a number of embodiments of this invention have been described, it is apparent that the basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

What is claimed is:

1. A solid form of Compound 1:

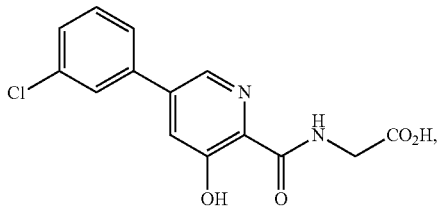

(Compound 1)

wherein said solid form is selected from the group consisting of:
(1) Solid Form D of Compound 1, wherein said Solid Form D has: an X-ray powder diffraction pattern comprising peaks at 7.9, 14.4, 14.8, 15.9, and 23.9±0.2° 2θ; an X-ray powder diffraction pattern comprising peaks at 5.9, 11.8, 16.8, 24.1, and 26.9±0.2° 2θ; an X-ray powder diffraction pattern comprising peaks at 6.6, 7.9, 13.4, 15.9, 20.1, and 24.5±0.2° 2θ; or an X-ray powder diffraction pattern substantially in accordance with FIG. 1;
(2) Solid Form E of Compound 1, wherein said Solid Form E has: an X-ray powder diffraction pattern comprising peaks at 21.3, 22.8, 23.7, 27.0, and 27.7±0.2° 2θ; an X-ray powder diffraction pattern comprising peaks at 16.4, 22.8, 23.6, 27.0, and 27.7±0.2° 2θ; or an X-ray powder diffraction pattern substantially in accordance with FIG. 4;
(3) Solid Form F of Compound 1, wherein said Solid Form F has: an X-ray powder diffraction pattern comprising peaks at 8.5, 15.3, 18.5, 21.3, and 22.5±0.2° 2θ; an X-ray powder diffraction pattern comprising peaks at 4.2, 12.7, 19.5, 25.9, and 29.9±0.2° 2θ; an X-ray powder diffraction pattern comprising peaks at 4.2, 8.5, 15.3, 18.5, 21.3, and 22.5±0.2° 2θ; or an X-ray powder diffraction pattern substantially in accordance with FIG. 7;
(4) Solid Form $H_B$ of Compound 1, wherein said Solid Form $H_B$ has: an X-ray powder diffraction pattern comprising peaks at 14.6, 15.3, 18.5, 20.4, and 28.1±0.2° 2θ; an X-ray powder diffraction pattern comprising peaks at 16.0, 20.4, 26.8, 28.1, and 29.6±0.2° 2θ; an X-ray powder diffraction pattern comprising peaks at 7.9, 14.6, 16.0, 17.6, and 28.1±0.2° 2θ; or an X-ray powder diffraction pattern substantially in accordance with FIG. 13;
(5) Solid Form $S_A$ of Compound 1, wherein said Solid Form $S_A$ has: an X-ray powder diffraction pattern comprising peaks at 13.1, 17.5, 19.1, 22.7, and 24.6±0.2° 2θ; an X-ray powder diffraction pattern comprising peaks at 13.1, 17.5, 19.1, 32.0, and 35.3±0.2° 2θ; an X-ray powder diffraction pattern comprising peaks at 13.1, 17.5, 19.1, 24.6, and 32.0±0.2° 2θ; or an X-ray powder diffraction pattern substantially in accordance with FIG. 16;
(6) Solid Form $S_B$ of Compound 1, wherein said Solid Form $S_B$ has: an X-ray powder diffraction pattern comprising peaks at 14.0, 19.6, 20.0, 22.0, and 28.5±0.2° 2θ; an X-ray powder diffraction pattern comprising peaks at 14.0, 19.6, 20.0, 31.5, and 33.6±0.2° 2θ; an X-ray powder diffraction pattern comprising peaks at 6.8, 14.0, 17.3, 19.6, 20.0, and 28.5±0.2° 2θ; or an X-ray powder diffraction pattern substantially in accordance with FIG. 19;
(7) Solid Form $S_C$ of Compound 1, wherein said Solid Form $S_C$ has: an X-ray powder diffraction pattern comprising peaks at 11.0, 15.1, 18.6, 22.1, and 26.4±0.2° 2θ; an X-ray powder diffraction pattern comprising peaks at 4.8, 9.5, 11.0, 21.8, and 34.8±0.2° 2θ; an X-ray powder diffraction pattern comprising peaks at 4.8, 7.9, 14.3, 18.6, 21.1, and 22.1±0.2° 2θ; or an X-ray powder diffraction pattern substantially in accordance with FIG. 24;
(8) Solid Form $S_D$ of Compound 1, wherein said Solid Form $S_D$ has: an X-ray powder diffraction pattern comprising peaks at 17.0, 24.0, 25.5, 26.2 and 28.4±0.2° 2θ; an X-ray powder diffraction pattern comprising peaks at 12.1, 14.5, 25.5, 29.2, and 36.2±0.2° 2θ; an X-ray powder diffraction pattern comprising peaks at 12.1, 17.0, 24.0, 25.5, and 26.2±0.2° 2θ; or an X-ray powder diffraction pattern substantially in accordance with FIG. 25;
(9) Solid Form $S_E$ of Compound 1, wherein said Solid Form $S_E$ has: an X-ray powder diffraction pattern comprising peaks at 15.8, 17.0, 24.6, 26.5, and 27.2±0.2° 2θ; an X-ray powder diffraction pattern comprising peaks at 14.5, 17.0, 25.1, 26.5, and 27.2±0.2° 2θ; an X-ray powder diffraction pattern comprising peaks at 14.5, 15.8, 22.4, 24.6, 26.5, and 27.2±0.2° 2θ; or an X-ray powder diffraction pattern substantially in accordance with FIG. 28; and
(10) Solid Form $S_F$ of Compound 1, wherein said Solid Form $S_F$ has: an X-ray powder diffraction pattern comprising peaks at 5.9, 11.8, 24.1, 24.3, and 26.2±0.2° 2θ; an X-ray powder diffraction pattern comprising peaks at 5.9, 11.8, 16.8, 24.1, and 26.9±0.2° 2θ; an X-ray powder diffraction pattern comprising peaks at 5.9, 11.8, 16.8, 24.3, 26.2, and 26.9±0.2° 2θ; or an X-ray powder diffraction pattern substantially in accordance with FIG. 31.

2. The solid form of claim 1, wherein said solid form is Solid Form D of Compound 1,
wherein said Solid Form D has: an X-ray powder diffraction pattern comprising peaks at 7.9, 14.4, 14.8, 15.9, and 23.9±0.2° 2θ; an X-ray powder diffraction pattern comprising peaks at 5.9, 11.8, 16.8, 24.1, and 26.9±0.2° 2θ; an X-ray powder diffraction pattern comprising peaks at 6.6, 7.9, 13.4, 15.9, 20.1, and 24.5±0.2° 2θ; or an X-ray powder diffraction pattern substantially in accordance with FIG. 1.

3. A pharmaceutical composition comprising the solid form of claim 1.

4. An oral dosage form comprising the solid form of claim 1.

5. A method of preparing the solid form of claim 1, wherein said solid form is solid Form D of Compound 1, comprising:
   a) preparing a solution of Compound 1 in methanol or methanol/water;
   b) bringing the solution to super-saturation to cause formation of solid Form D of Compound 1; and
   c) isolating solid Form D of Compound 1.

6. The solid form of claim 1, wherein said solid form is Solid Form E of Compound 1,
   wherein said Solid Form E has: an X-ray powder diffraction pattern comprising peaks at 21.3, 22.8, 23.7, 27.0, and 27.7±0.2° 2θ; an X-ray powder diffraction pattern comprising peaks at 16.4, 22.8, 23.6, 27.0, and 27.7±0.2° 2θ; or an X-ray powder diffraction pattern substantially in accordance with FIG. 4.

7. A method of preparing the solid form of claim 1, wherein said solid form is solid Form E of Compound 1, comprising:
   a) preparing a solution of Compound 1 in tetrahydrofuran or methyl ethyl ketone;
   b) bringing the solution to super-saturation to cause formation of solid Form E of Compound 1; and
   c) isolating solid Form E of Compound 1.

8. The solid form of claim 1, wherein said solid form is Solid Form F of Compound 1,
   wherein said Solid Form F has: an X-ray powder diffraction pattern comprising peaks at 8.5, 15.3, 18.5, 21.3, and 22.5±0.2° 2θ; an X-ray powder diffraction pattern comprising peaks at 4.2, 12.7, 19.5, 25.9, and 29.9±0.2° 2θ or at 4.2, 8.5, 15.3, 18.5, 21.3, and 22.5±0.2° 2θ; or an X-ray powder diffraction pattern substantially in accordance with FIG. 7.

9. A method of preparing the solid form of claim 1, wherein said solid form is solid Form F of Compound 1, comprising:
   a) preparing a solution of Compound 1 in ethanol/water;
   b) bringing the solution to super-saturation to cause formation of solid Form F of Compound 1; and
   c) isolating solid Form F of Compound 1.

10. The solid form of claim 1, wherein said solid form is Solid Form $H_B$ of Compound 1,
   wherein said Solid Form $H_B$ has: an X-ray powder diffraction pattern comprising peaks at 14.6, 15.3, 18.5, 20.4, and 28.1±0.2° 2θ; an X-ray powder diffraction pattern comprising peaks at 16.0, 20.4, 26.8, 28.1, and 29.6±0.2° 2θ an X-ray powder diffraction pattern comprising peaks at 7.9, 14.6, 16.0, 17.6, and 28.1±0.2° 2θ; or an X-ray powder diffraction pattern substantially in accordance with FIG. 13.

11. A method of preparing the solid form of claim 1, wherein said solid form is Solid Form $H_B$ of Compound 1, comprising:
   a) preparing a solution of Compound 1 in methanol;
   b) bringing the solution to super-saturation to cause formation of solid Form $H_B$ of Compound 1; and
   c) isolating solid Form $H_B$ of Compound 1.

12. The solid form of claim 1, wherein said solid form is Solid Form $S_A$ of Compound 1,
   wherein said Solid Form $S_A$ has: an X-ray powder diffraction pattern comprising peaks at 13.1, 17.5, 19.1, 22.7, and 24.6±0.2° 2θ; an X-ray powder diffraction pattern comprising peaks at 13.1, 17.5, 19.1, 32.0, and 35.3±0.2° 2θ; an X-ray powder diffraction pattern comprising peaks at 13.1, 17.5, 19.1, 24.6, and 32.0±0.2° 2θ; or an X-ray powder diffraction pattern substantially in accordance with FIG. 16.

13. A method of preparing the solid form of claim 1, wherein said solid form is solid Form $S_A$, $S_b$, or $S_c$ of Compound 1, comprising:
   a) preparing a solution of Compound 1 in 1,4-dioxane;
   b) bringing the solution to super-saturation to cause formation of solid Form $S_A$, $S_b$, or $S_c$ of Compound 1; and
   c) isolating solid Form $S_A$, $S_b$, or $S_c$ of Compound 1.

14. The solid form of claim 1, wherein said solid form is Solid Form $S_B$ of Compound 1,
   wherein said Solid Form $S_B$ has: an X-ray powder diffraction pattern comprising peaks at 14.0, 19.6, 20.0, 22.0, and 28.5±0.2° 2θ; an X-ray powder diffraction pattern comprising peaks at 14.0, 19.6, 20.0, 31.5, and 33.6±0.2° 2θ; an X-ray powder diffraction pattern comprising peaks at 6.8, 14.0, 17.3, 19.6, 20.0, and 28.5±0.2° 2θ; or an X-ray powder diffraction pattern substantially in accordance with FIG. 19.

15. The solid form of claim 1, wherein said solid form is Solid Form $S_C$ of Compound 1,
   wherein said Solid Form $S_C$ has: an X-ray powder diffraction pattern comprising peaks at 11.0, 15.1, 18.6, 22.1, and 26.4±0.2° 2θ; an X-ray powder diffraction pattern comprising peaks at 4.8, 9.5, 11.0, 21.8, and 34.8±0.2° 2θ; an X-ray powder diffraction pattern comprising peaks at 4.8, 7.9, 14.3, 18.6, 21.1, and 22.1±0.2° 2θ; or an X-ray powder diffraction pattern substantially in accordance with FIG. 24.

16. The solid form of claim 1, wherein said solid form is Solid Form $S_D$ of Compound 1,
   wherein said Solid Form $S_D$ has: an X-ray powder diffraction pattern comprising peaks at 17.0, 24.0, 25.5, 26.2 and 28.4±0.2° 2θ; an X-ray powder diffraction pattern comprising peaks at 12.1, 14.5, 25.5, 29.2, and 36.2±0.2° 2θ; an X-ray powder diffraction pattern comprising peaks at 12.1, 17.0, 24.0, 25.5, and 26.2±0.2° 2θ; or an X-ray powder diffraction pattern substantially in accordance with FIG. 25.

17. A method of preparing the solid form of claim 1, wherein said solid form is solid Form $S_D$ of Compound 1, comprising:
   a) preparing a solution of Compound 1 in anisole;
   b) bringing the solution to super-saturation to cause formation of solid Form $S_D$ of Compound 1; and
   c) isolating solid Form $S_D$ of Compound 1.

18. The solid form of claim 1, wherein said solid form is Solid Form $S_E$ of Compound 1,
   wherein said Solid Form $S_E$ has: an X-ray powder diffraction pattern comprising peaks at 15.8, 17.0, 24.6, 26.5, and 27.2±0.2° 2θ; an X-ray powder diffraction pattern comprising peaks at 14.5, 17.0, 25.1, 26.5, and 27.2±0.2° 2θ; an X-ray powder diffraction pattern comprising peaks at 14.5, 15.8, 22.4, 24.6, 26.5, and 27.2±0.2° 2θ; or an X-ray powder diffraction pattern substantially in accordance with FIG. 28.

19. A method of preparing the solid form of claim 1, wherein said solid form is solid Form $S_E$ or $S_F$ of Compound 1, comprising:
a) preparing a solution of Compound 1 in dimethylacetamide;
b) bringing the solution to super-saturation to cause formation of solid Form $S_E$ or $S_F$ of Compound 1; and
c) isolating solid Form $S_E$ or $S_F$ of Compound 1.

20. The solid form of claim 1, wherein said solid form is Solid Form $S_F$ of Compound 1, wherein said Solid Form $S_F$ has: an X-ray powder diffraction pattern comprising peaks at 5.9, 11.8, 24.1, 24.3, and 26.2±0.2° 2θ; an X-ray powder diffraction pattern comprising peaks at 5.9, 11.8, 16.8, 24.1, and 26.9±0.2° 2θ; an X-ray powder diffraction pattern comprising peaks at 5.9, 11.8, 16.8, 24.3, 26.2, and 26.9±0.2° 2θ; or an X-ray powder diffraction pattern substantially in accordance with FIG. 31.

\* \* \* \* \*